US012398188B2

(12) United States Patent
Zhong et al.

(10) Patent No.: US 12,398,188 B2
(45) Date of Patent: Aug. 26, 2025

(54) CYTOKINE FUSION PROTEINS, AND THEIR PHARMACEUTICAL COMPOSITIONS AND THERAPEUTIC APPLICATIONS

(71) Applicant: Anwita Biosciences, Inc., San Carlos, CA (US)

(72) Inventors: Ziyang Zhong, Belmont, CA (US); Fan Ye, Mountain View, CA (US); Matthew Siegel, Menlo Park, CA (US); Jianing Huang, San Mateo, CA (US)

(73) Assignee: Anwita Biosciences, Inc., San Carlos, CA (US)

( * ) Notice: Subject to any disclaimer, the term of this patent is extended or adjusted under 35 U.S.C. 154(b) by 161 days.

(21) Appl. No.: 18/346,250

(22) Filed: Jul. 2, 2023

(65) Prior Publication Data

US 2023/0348549 A1 Nov. 2, 2023

Related U.S. Application Data

(62) Division of application No. 16/952,079, filed on Nov. 19, 2020, now Pat. No. 11,692,020.

(60) Provisional application No. 62/938,275, filed on Nov. 20, 2019.

(51) Int. Cl.
*A61K 38/00* (2006.01)
*C07K 14/55* (2006.01)
*C07K 16/00* (2006.01)

(52) U.S. Cl.
CPC .............. *C07K 14/55* (2013.01); *C07K 16/00* (2013.01); *A61K 38/00* (2013.01); *C07K 2317/565* (2013.01); *C07K 2317/569* (2013.01); *C07K 2319/31* (2013.01); *C07K 2319/33* (2013.01)

(58) Field of Classification Search
CPC .................................................. A61K 38/2013
See application file for complete search history.

(56) References Cited

U.S. PATENT DOCUMENTS

| | | |
|---|---|---|
| 7,569,215 B2 | 8/2009 | Wittrup et al. |
| 7,951,360 B2 | 5/2011 | Wittrup et al. |
| 8,349,311 B2 | 1/2013 | Wittrup et al. |
| 8,945,897 B2 | 2/2015 | Siekmann et al. |
| 9,732,134 B2 | 8/2017 | Gavin et al. |
| 9,957,323 B2 | 5/2018 | Sainson et al. |
| 10,035,836 B1 | 7/2018 | Greve |
| 10,143,726 B2 | 12/2018 | Oft |
| 10,604,576 B2 | 3/2020 | Campbell et al. |
| 10,851,144 B2 | 12/2020 | Butz et al. |
| 2010/0150939 A1 | 6/2010 | Blanchetot et al. |
| 2015/0093336 A1 | 4/2015 | Ginderachter et al. |
| 2015/0158929 A1 | 6/2015 | Schellenberger et al. |
| 2016/0207991 A1 | 7/2016 | Bloom et al. |
| 2017/0107302 A1 | 4/2017 | Silence et al. |
| 2017/0362339 A1 | 12/2017 | Liu et al. |
| 2018/0326010 A1 | 11/2018 | Deak et al. |
| 2018/0326060 A1 | 11/2018 | Wesche et al. |
| 2019/0016793 A1 | 1/2019 | Cini et al. |
| 2019/0031749 A1 | 1/2019 | Dubridge et al. |
| 2019/0046611 A1 | 2/2019 | Ali et al. |
| 2019/0202917 A1 | 7/2019 | Campbell et al. |
| 2019/0338032 A1 | 11/2019 | Campbell et al. |
| 2019/0352363 A1 | 11/2019 | Seidel, III et al. |
| 2020/0199181 A1 | 6/2020 | Seidel, III et al. |
| 2020/0207824 A1 | 7/2020 | Seidel, III et al. |

FOREIGN PATENT DOCUMENTS

| | | |
|---|---|---|
| CA | 3098765 A1 | 3/2020 |
| CA | 3098930 A1 | 3/2020 |
| CN | 110325205 A | 10/2019 |
| CN | 111647068 A | 9/2020 |
| WO | 2005005638 A2 | 1/2005 |
| WO | 2005007121 A2 | 1/2005 |
| WO | 2010085495 A1 | 7/2010 |
| WO | 2016164937 A2 | 10/2016 |
| WO | 2016196211 A1 | 12/2016 |
| WO | 2017158436 A1 | 9/2017 |
| WO | 2018071918 A1 | 4/2018 |
| WO | 2018104444 A1 | 6/2018 |
| WO | 2018119114 A1 | 6/2018 |
| WO | 2018151868 A2 | 8/2018 |
| WO | 2018170168 A1 | 9/2018 |
| WO | 2018184964 A1 | 10/2018 |
| WO | 2019051091 A1 | 3/2019 |
| WO | 2019051094 A1 | 3/2019 |
| WO | 2019125732 A1 | 6/2019 |
| WO | 2019139896 A1 | 7/2019 |
| WO | 2019246003 A1 | 12/2019 |
| WO | 2019246004 A1 | 12/2019 |
| WO | 2020057645 A1 | 3/2020 |
| WO | 2020057646 A1 | 3/2020 |
| WO | 2020125743 A1 | 6/2020 |
| WO | 2020172528 A1 | 8/2020 |

OTHER PUBLICATIONS

Abbas et al., "Revisiting IL-2: Biology and therapeutic prospects," Sci. Immunol. 2018, 3, eaat1482.
Adams et al., "Extending the half-life of a fab fragment through generation of a humanized anti-human serum albumin Fv domain: An investigation into the correlation between affinity and serum half-life," MAbs 2016, 8, 1336-46.
Agrawalla et al., "Chemoselective dual labeling of native and recombinant proteins," Bioconjugate Chem. 2018, 29, 29-34.
Atkins et al., "High-dose recombinant interleukin 2 therapy for patients with metastatic melanoma: analysis of 270 patients treated between 1985 and 1993," J. Clin. Oncol. 1999, 17, 2105-16.

(Continued)

*Primary Examiner* — Prema M Mertz
(74) *Attorney, Agent, or Firm* — Lin Yu; Juniv LLP

(57) ABSTRACT

Provided herein are a fusion protein comprising first and second cytokine domains, and a half-life extension domain; and a pharmaceutical composition thereof. Also provided herein are methods of their use for treating, preventing, or ameliorating one or more symptoms of a proliferative disease.

29 Claims, 4 Drawing Sheets
Specification includes a Sequence Listing.

(56) References Cited

OTHER PUBLICATIONS

Bluestone, "The yin and yang of interleukin-2-mediated immunotherapy," N. Engl. J. Med. 2011, 365, 2129-31.
Boyman et al., "The role of interleukin-2 during homeostasis and activation of the immune system," Nat. Rev. Immunol. 2012, 12, 180-90.
Conlon et al., "Cytokines in the treatment of cancer," J. Interferon Cytokine Res. 2019, 39, 6-21.
Conlon et al., "Redistribution, hyperproliferation, activation of natural killer cells and CD8 T cells, and cytokine production during first-in-human clinical trial of recombinant human interleukin-15 in patients with cancer," J. Clin. Oncol. 2015, 33, 74-82.
Croce et al., "IL-21: a pleiotropic cytokine with potential applications in oncology," J. Immunol. Res. 2015, 696578.
Davis et al., "An open-label, two-arm, phase I trial of recombinant human interleukin-21 in patients with metastatic melanoma," Clin. Cancer Res. 2007, 13, 3630-36.
Dennis et al., "Albumin binding as a general strategy for improving the pharmacokinetics of proteins," J. Biol. Chem. 2002, 277, 35035-43.
Heaton et al., "Human interleukin 2 analogues that preferentially bind the intermediate-affinity interleukin 2 receptor lead to reduced secondary cytokine secretion: implications for the use of these interleukin 2 analogues in cancer immunotherapy," Cancer Res. 1993, 53, 2597-602.
Hondowicz et al., "Interleukin-2-dependent allergen-specific tissue-resident memory cells drive asthma," Immunity 2016, 44, 155-66.
Hu et al., "Generation of low-toxicity interleukin-2 fusion proteins devoid of vasopermeability activity," Blood 2002, 101, 4853-61.
Huang et al., "A novel strategy to produce high level and high purity of bioactive IL15 fusion proteins from mammalian cells," Protein Expr. Purifi. 2018, 148, 30-9.
Klapper et al., "High-dose interleukin-2 for the treatment of metastatic renal cell carcinoma : a retrospective analysis of response and survival in patients treated in the surgery branch at the National Cancer Institute between 1986 and 2006," Cancer 2008, 113, 293-301.
Leonard and Wan, "IL-21 signaling in immunity," F1000Res. 2016, 5(F1000 Faculty Rev), 224.
Liao et al., "IL-2 family cytokines: new insights into the complex roles of IL-2 as a broad regulator of T helper cell differentiation," Curr. Opin. Immunol. 2011, 23, 598-604.
Malek et al., "Interleukin-2 receptor signaling: at the interface between tolerance and immunity," Immunity 2010, 33, 153-65.
PROLEUKIN® Label (2012).
Rham et al., "The proinflammatory cytokines IL-2, IL-15 and IL-21 modulate the repertoire of mature human natural killer cell receptors," Arthritis Res. Ther. 2007, 9, R125.
Richert et al., "Compensatory energetic mechanisms mediating the assembly of signaling complexes between interleukin-2 and its alpha, beta, and gamma(c) receptors," J. Mol. Biol. 2004, 339, 1115-9.
Ridgway et al., "'Knobs-into-holes' engineering of antibody CH3 domains for heavy chain heterodimerization," Protein Eng. 1996, 9, 617-21.
Robb et al., "Low and high affinity cellular receptors for interleukin 2. Implications for the level of Tac antigen," J. Exp. Med. 1984, 160, 1126-46.
Robinson and Schluns, "The potential and promise of IL-15 in immuno-oncogenic therapies," Immunol. Lett. 2017, 159-68.
Rosenberg, "IL-2: the first effective immunotherapy for human cancer," J. Immunol. 2014, 192, 5451-8.
Rosenberg, "Raising the bar: the curative potential of human cancer immunotherapy," Sci. Transl. Med. 2012, 4, 127ps8.
Schmidt et al., "Safety and clinical effect of subcutaneous human interleukin-21 in patients with metastatic melanoma or renal cell carcinoma: a phase I trial," Clin. Cancer Res. 2010, 16, 5312-9.
Skrombolas et al., "Challenges and developing solutions for increasing the benefits of IL-2 treatment in tumor therapy," Expert Rev. Clin. Immunol. 2014, 10, 207-17.
Sola and Griebenow, "Effects of glycosylation on the stability of protein pharmaceuticals," J. Pharm. Sci. 2009, 98, 1223-45.
Sola et al., "Modulation of protein biophysical properties by chemical glycosylation: biochemical insights and biomedical implications," Cell. Mol. Life Sci. 2007, 64, 2133-52.
Spangler et al., "Insights into cytokine-receptor interactions from cytokine engineering," Annu. Rev. Immunol. 2015, 33, 139-67.
Stauber et al., "Crystal structure of the IL-2 signaling complex: Paradigm for a heterotrimeric cytokine receptor," Proc. Natl. Acad. Sci. U.S.A. 2006, 103, 2788-93.
Steel et al., "Interleukin-15 biology and its therapeutic implications in cancer," Trends Pharmacol. Sci 2012, 33, 35-41.
Szabo et al., "High Performance Anion Exchange and Hydrophilic Interaction Liquid Chromatography Approaches for Comprehensive Mass Spectrometry-Based Characterization of the N-Glycome of a Recombinant Human Erythropoietin," J. Proteome. Res. 2018, 17, 1559-74.
Tang and Harding, "The challenges and molecular approaches surrounding interleukin-2-based therapeutics in cancer," Cytokine: X 2019, 1, 100001.
Waldmann et al., "The biology of interleukin-2 and interleukin-15: implications for cancer therapy and vaccine design," Nat. Rev. Immunol. 2006, 6, 595-601.
Waldmann, "The shared and contrasting roles of IL2 and IL15 in the life and death of normal and neoplastic lymphocytes: implications for cancer therapy," Cancer Immunol. Res. 2015, 3, 219-27.
Wang et al., "Structure of the quaternary complex of interleukin-2 with its a, B, and yc receptors," Science 2005, 310, 1159-63.

CYTOKINE FUSION PROTEINS, AND THEIR PHARMACEUTICAL COMPOSITIONS AND THERAPEUTIC APPLICATIONS

CROSS REFERENCE TO RELATED APPLICATION

This application is a divisional of U.S. application Ser. No. 16/952,079, filed Nov. 19, 2020; which claims the benefit of U.S. Provisional Application No. 62/938,275, filed Nov. 20, 2019; the disclosure of each of which is incorporated herein by reference in its entirety.

FIELD

Provided herein are a fusion protein comprising first and second cytokine domains, and a half-life extension domain; and a pharmaceutical composition thereof. Also provided herein are methods of their use for treating, preventing, or ameliorating one or more symptoms of a proliferative disease.

REFERENCE TO A SEQUENCE LISTING

The present specification is being filed with a Sequence Listing in Computer Readable Form (CRF), which is entitled 216A005US02D_SEQ_LISTING_ST26.txt of 187,453 bytes in size and created Jul. 2, 2023; the content of which is incorporated herein by reference in its entirety.

BACKGROUND

Cytokines regulate the innate and adaptive immune system, and control proliferation, differentiation, effector functions, and survival of leukocytes. Conlon et al., *J. Interferon Cytokine Res.* 2019, 39, 6-21. Because of the ability of the immune system to recognize and destroy cancer cells, cytokines have been explored as therapeutic agents for cancer treatment. Id.

An interleukin-2 (IL-2) is a pleiotropic cytokine that orchestrates the proliferation, survival, and function of both immune effector (Teff) cells and regulatory T (Treg) cells to maintain immune homeostasis. Bluestone, *N. Engl. J. Med.* 2011, 365, 2129-31; Boyman et al., *Nat. Rev. Immunol.* 2012, 12, 180-90. The IL-2 drives T-cell growth, augments natural killer (NK) cytolytic activity, induces the differentiation of regulatory T (Treg) cells, and mediates activation-induced cell death. Liao et al., *Curr. Opin. Immunol.* 2011, 23, 598-604.

An interleukin-2 receptor (IL-2R) exists in three different forms generated from three different interleukin-2 receptor chains: α chain (IL-2Rα or CD25), β chain (IL-2Rβ or CD122), and γ chain (IL-2Rγ, $\gamma_c$, or CD132). Wang et al., *Science* 2005, 310, 1159-63. The IL-2 binds the IL-2Rα with a low affinity ($K_d$~10 nM). Id. From a crystal structure of a quaternary IL-2 signaling complex, fifteen amino acid residues (K35, T37, R38, T41, F42, K43, F44, Y45, E61, E62, K64, P65, E68, L72, and Y107) on the IL-2 are identified as interface residues between the IL-2 and IL-2Rα. Stauber et al., *Proc. Natl. Acad. Sci. U.S.A.* 2006, 103, 2788-93. The IL-2 binds a heterodimeric complex of the IL-2Rβ and IL-2Rγ, expressed on memory T cells and NK cells, with an intermediate affinity ($K_d$~1 nM). Wang et al., *Science* 2005, 310, 1159-63. The IL-2 binds a heterotrimeric complex of the IL-2Rα, IL-2Rβ, and IL-2Rγ, expressed on Treg cells, with a high affinity ($K_d$~10 pM). Id. The IL-2 binds the IL-2Rβ alone with a dissociation constant ($K_d$) of about 100 nM. Id. The IL-2Rα by itself has no signal-transducing activity. Id. The IL-2 signals through the intermediate-affinity heterodimeric IL-2Rβ/γ complex or the high-affinity heterotrimeric IL-2Rα/β/γ complex. Liao et al., *Curr. Opin. Immunol.* 2011, 23, 598-604. The binding of the IL-2 to the intermediate-affinity heterodimeric IL-2Rβ/γ complex leads to the activation and proliferation of immunostimulatory Teff cells, while the binding of the IL-2 to the high-affinity heterotrimeric IL-2Rα/β/γ complex results in the activation and proliferation of immunosuppressive Treg cells. Malek et al., *Immunity* 2010, 33, 153-65; Bluestone, *N. Engl. J. Med.* 2011, 365, 2129-2131; Boyman et al., *Nat. Rev. Immunol.* 2012, 12, 180-90; Spangler et al., *Annu. Rev. Immunol.* 2015, 33, 139-67. This dual opposing functions of immunostimulation and immunosuppression pose a major challenge in developing the IL-2 as a safe and effective therapeutic agent. Skrombolas et al., *Expert Rev. Clin. Immunol.* 2014, 10, 207-17; Abbas et al., *Sci. Immunol.* 2018, 3, eaat 1482.

Aldesleukin, a recombinant human IL-2, was approved by the FDA for metastatic renal cell carcinoma in 1992 and for metastatic melanoma in 1998. Rosenberg, *J. Immunol.* 2014, 192, 5451-8. Patients with metastatic melanoma or renal cancer experience a 5 to 10% rate of complete cancer regression, with an additional 10% experiencing a partial regression. Atkins et al., *J. Clin. Oncol.* 1999, 17, 2105-16; Klapper et al., *Cancer* 2008, 113, 293-301. Approximately 70% of complete responders to the IL-2 therapy do not recur. Rosenberg, *Sci. Transl. Med.* 2012, 4, 127ps8. However, the success of the IL-2 as an immunotherapy for cancer has been hampered by its severe toxicities and limited efficacy. One major limiting factor for its efficacy as an anticancer agent is immunosuppression resulting from the IL-2-driven preferential expansion of Treg cells. Abbas et al., *Sci. Immunol.* 2018, 3, eaat1482. Moreover, for the IL-2 to be effective in cancer treatment, a high dose therapeutic schedule is required. Bluestone, *N. Engl. J. Med.* 2011, 365, 2129-31; Abbas et al., *Sci. Immunol.* 2018, 3, eaat 1482. This dosing regimen, however, causes vascular leak syndrome and results in the limited application of IL-2 in cancer treatment. Abbas et al., *Sci. Immunol.* 2018, 3, eaat 1482. Moreover, aldesleukin has a half-life of only about 13 to 85 minutes in human following a 5-minute intravenous infusion. PROLEUKIN® Label (2012).

An interleukin-15 (IL-15) is a cytokine structurally similar to an IL-2. Waldmann, *Cancer Immunol. Res.* 2015, 3, 219-227. They also share two common receptor subunits: CD122 (IL-2Rβ/IL-15Rβ) and CD132 (IL-2Rγ). Waldmann et al., *Nat. Rev. Immunol.* 2006, 6, 595-601. An IL-15 plays pivotal roles in the control of the life and death of lymphocytes. Id. Like aldesleukin, however, the recombinant IL-2 used in a clinical trial for treating metastatic melanoma or metastatic renal cell cancer has a half-life of only about 2.5 hours in human following an intravenous infusion. Conlon et al., *J. Clin. Oncol.* 2015, 33, 74-82.

An interleukin-21 (IL-21) is a pleiotropic cytokine that regulates the activity of both innate and specific immunity. Croce et al., *J. Immunol. Res.* 2015, 696578. An IL-21 stimulates T and natural killer (NK) cell proliferation and function and regulates B cell survival and differentiation and the function of dendritic cells. Id. An interleukin-21 receptor (IL-21R) has been shown to be expressed in diverse hematopoietic malignancies, including chronic lymphocytic leukemia (CLL), follicular lymphoma, diffuse large B-cell lymphoma (DLBCL), and mantle cell lymphoma. Conlon et al., *J. Interferon Cytokine Res.* 2019, 39, 6-21. Several preclinical studies showed that IL-21 has antitumor activity in different tumor models, through mechanism involving the activation of NK and T or B cell responses. Croce et al., *J. Immunol. Res.* 2015, 696578. However, just like aldesleukin, the recombinant IL-2 used in a clinical trial for treating metastatic melanoma has a half-life of only about 1 to 4 hours in human following an intravenous infusion. Davis et al., *Clin. Cancer Res.* 2007, 13, 3630-36.

Therefore, there is a need for an effective immunotherapy with an improved half-life for cancer treatment.

SUMMARY OF THE DISCLOSURE

Provided herein is a fusion protein comprising first and second cytokine domains, and a half-life extension domain; wherein the first and second cytokine domains are different. In one embodiment, the half-life extension domain is an albumin binding domain, a fragment crystallizable (Fc) domain, a serum albumin, a polyethylene glycol, or a fatty acyl group.

Also provided herein is a fusion protein comprising an interleukin domain that causes the fusion protein to signal through a receptor comprising CD122 (IL-2Rβ/IL-15Rβ) and CD132 (IL-2Rγ) subunits, an interleukin-21 domain, and a half-life extension domain.

Additionally, provided herein is a fusion protein comprising an interleukin-2 domain, an interleukin-21 domain, and a half-life extension domain.

Furthermore, provided herein is a fusion protein comprising an interleukin-2 domain, an interleukin-21 domain, and an albumin binding domain.

Provided herein is a fusion protein comprising an interleukin-2 domain, an interleukin-21 domain, an albumin binding domain, and optionally first and second peptide linkers; wherein the carboxy-terminus (C-terminus) of the interleukin-2 domain is connected to the amino-terminus (N-terminus) of the interleukin-21 domain directly or via the first peptide linker; and the C-terminus of the interleukin-21 domain is connected to the N-terminus of the albumin binding domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

Provided herein is a fusion protein comprising an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker.

Provided herein is a fusion protein comprising an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker.

Provided herein is a fusion protein comprising an interleukin-2 domain, an interleukin-21 domain, and a fragment crystallizable (Fc) domain.

Provided herein is a fusion protein comprising an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the C-terminus of the interleukin-21 domain is connected to the N-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the N-terminus of the interleukin-21 domain is connected to the C-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the N-terminus of the interleukin-21 domain is connected to the C-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the C-terminus of the interleukin-21 domain is connected to the N-terminus of the second peptide chain of the Fc domain directly or via the second peptide linker.

Provided herein is a fusion protein comprising first and second interleukin-2 domains, an interleukin-21 domain, an Fc domain having first and second peptide chains, and optionally a first, second, and third peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; and the N-terminus of the interleukin-21 domain is connected to the C-terminus of the first peptide chain of the Fc domain directly or via the third peptide linker.

Provided herein is a fusion protein comprising first and second interleukin-2 domains, an interleukin-21 domain, an Fc domain having first and second peptide chains, and optionally a first, second, and third peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; and the C-terminus of the interleukin-21 domain is connected to the N-terminus of the first peptide chain of the Fc domain directly or via the third peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; the N-terminus of the first interleukin-21 domain is connected to the C-terminus of the first peptide chain of the Fc domain directly or via the third peptide linker; and the N-terminus of the second interleukin-21 domain is connected to the C-terminus of the second peptide chain of the Fc domain directly or via the fourth peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; the C-terminus of the first interleukin-21 domain is connected to the N-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the N-terminus of the second interleukin-2 domain is connected to the C-terminus of the second peptide chain of the Fc domain directly or via the second peptide linker; the N-terminus of the first interleukin-21 domain is connected to the C-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

Provided herein is a pharmaceutical composition comprising a fusion protein provided herein and a pharmaceutically acceptable excipient.

Provided herein is a method of treating, preventing, or ameliorating one or more symptoms of a proliferative disease in a subject, comprising administering to the subject in need thereof a therapeutically effective amount of a fusion protein provided herein.

Provided herein is a method of activating an immune effector cell, comprising contacting the cell with an effective amount of a fusion protein provided herein.

DETAILED DESCRIPTION

Figure 1:
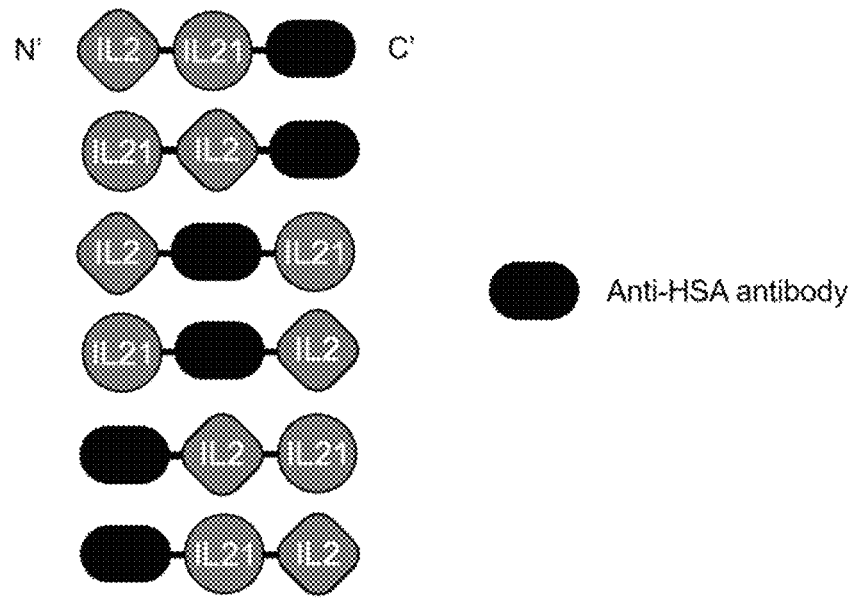
FIG. 1 shows the configurations of exemplary fusion proteins comprising an interleukin-2 (IL-2) domain, an interleukin-21 (IL-21) domain, and an anti-HSA antibody as an example of a half-life extension domain.
Figure 2:
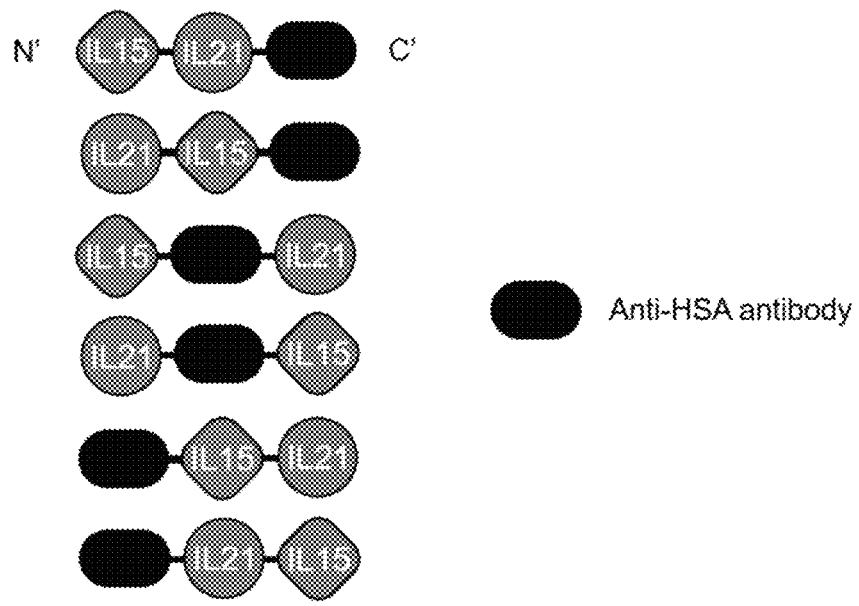
FIG. 2 shows the configurations of exemplary fusion proteins comprising an interleukin-15 (IL-15) domain, an IL-21 domain, and an anti-HSA antibody as an example of a half-life extension domain.
Figure 3:
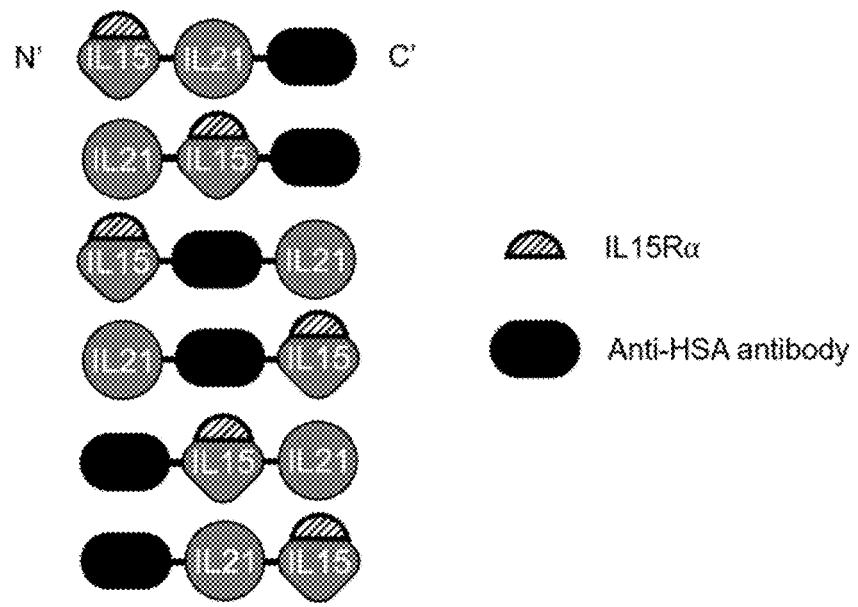
FIG. 3 shows the configurations of exemplary fusion proteins comprising an IL-15 variant domain, an IL-21 domain, and an anti-HSA antibody as an example of a half-life extension domain.

To facilitate understanding of the disclosure set forth herein, a number of terms are defined below.

Generally, the nomenclature used herein and the laboratory procedures in biochemistry, biology, cell biology, molecular biology, immunology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.; The Pharmaceutical Press: 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Synapse Information Resources, Inc.: 2007; *Pharmaceutical Preformulation and Formulation,* 2nd ed.; Gibson Ed.; CRC Press: 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "substantially pure" and "substantially homogeneous" mean sufficiently homogeneous to appear free of readily detectable impurities as determined by standard analytical methods used by one of ordinary skill in the art, including, but not limited to, gel electrophoresis, high performance liquid chromatography (HPLC), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound as determined by standard analytical methods.

Cytokine Fusion Proteins

In one embodiment, provided herein is a fusion protein comprising first and second cytokine domains, and a half-life extension domain; wherein the first and second cytokine domains are different.

In one embodiment, the first cytokine domain is an interleukin domain. In another embodiment, the second cytokine domain is an interleukin domain. In yet another embodiment, the first and second cytokine domains are each an interleukin domain.

In certain embodiments, the half-life extension domain extends the half-life of the first and/or second cytokine domains in vivo as compared to the corresponding free wild-type cytokines. In certain embodiments, the half-life extension domain extends the half-life of the first cytokine domain in vivo as compared to the corresponding free wild-type cytokine. In certain embodiments, the half-life extension domain extends the half-life of the second cytokine domain in vivo as compared to the corresponding free wild-type cytokine.

In certain embodiments, the half-life extension domain comprises an albumin binding domain, a fragment crystallizable (Fc) domain, a serum albumin, a polyethylene glycol (PEG), or a fatty acyl group. In one embodiment, the half-life extension domain is an albumin binding domain. In another embodiment, the half-life extension domain is an Fc domain. In yet another embodiment, the half-life extension domain is an Fc domain having first and second peptide chains. In yet another embodiment, the half-life extension domain is a serum albumin. In yet another embodiment, the half-life extension domain comprises a PEG. In still another embodiment, the half-life extension domain comprises a fatty acyl group.

In certain embodiments, the fusion protein provided herein has an affinity to the receptor of the first cytokine domain that is lower than that to the receptor of the second cytokine domain. In certain embodiments, the fusion protein provided herein has an affinity to the receptor of the first cytokine domain that is no less than about 2-fold, no less than about 5-fold, no less than about 10-fold, no less than about 20-fold, or no less than about 50-fold lower than that to the receptor of the second cytokine domain. In certain embodiments, the fusion protein provided herein has an affinity to the receptor of the first cytokine domain that is no less than about 2-fold lower than that to the receptor of the second cytokine domain. In certain embodiments, the fusion protein provided herein has an affinity to the receptor of the first cytokine domain that is no less than about 5-fold lower than that to the receptor of the second cytokine domain. In certain embodiments, the fusion protein provided herein has an affinity to the receptor of the first cytokine domain that is no less than about 10-fold lower than that to the receptor of the second cytokine domain. In certain embodiments, the fusion protein provided herein has an affinity to the receptor of the first cytokine domain that is no less than about 20-fold lower than that to the receptor of the second cytokine domain. In certain embodiments, the fusion protein provided herein has an affinity to the receptor of the first cytokine domain that is no less than about 50-fold lower than that to the receptor of the second cytokine domain.

In certain embodiments, the first cytokine domain comprises an amino acid sequence of an interleukin-2, or a variant or mutein thereof; or interleukin-15, or a variant or mutein thereof. In certain embodiments, the first cytokine domain comprises an amino acid sequence of an interleukin-2, or a variant or mutein thereof. In certain embodiments, the first cytokine domain comprises an amino acid sequence of an interleukin-15, or a variant or mutein thereof. In certain embodiments, the second cytokine domain comprises an amino acid sequence of an interleukin-21, or a variant or mutein thereof.

In one embodiment, the fusion protein provided herein has a biological activity of the corresponding cytokine of the first cytokine domain that is no less than about 2-fold, no less than about 5-fold, no less than about 10-fold, no less than about 20-fold, or no less than about 50-fold higher than that of the corresponding free cytokine. In another embodiment, the fusion protein provided herein has a biological activity of the corresponding cytokine of the first cytokine domain that is no less than about 2-fold higher than that of the corresponding free cytokine. In yet another embodiment, the fusion protein provided herein has a biological activity of the corresponding cytokine of the first cytokine domain that is no less than about 5-fold higher than that of the corresponding free cytokine. In yet another embodiment, the fusion protein provided herein has a biological activity of the corresponding cytokine of the first cytokine domain that is no less than about 10-fold higher than that of the corresponding free cytokine. In yet another embodiment, the fusion protein provided herein has a biological activity of the corresponding cytokine of the first cytokine domain that is no less than about 20-fold higher than that of the corresponding free cytokine. In still another embodiment, the fusion protein provided herein has a biological activity of the corresponding cytokine of the first cytokine domain that is no less than about 50-fold higher than that of the corresponding free cytokine.

In certain embodiments, the biological activity is STAT5 phosphorylation in a human T cell. In certain embodiments, the biological activity is proliferation of an activated human T cell. In certain embodiments, the biological activity is secretion of pro-inflammatory cytokines from a human T cell.

In another embodiment, provided herein is a fusion protein comprising a first interleukin domain that causes the fusion protein to signal through a receptor comprising an CD122 (IL-2Rβ/IL-15Rβ) and CD132 (IL-2Rγ) subunits, an interleukin-21 domain, and a half-life extension domain.

In one embodiment, the first interleukin domain comprises an amino acid sequence of an interleukin-2, or a variant or mutein thereof; or interleukin-15, or a variant or mutein thereof. In another embodiment, the first interleukin domain comprises an amino acid sequence of an interleukin-2, or a variant or mutein thereof. In yet another embodiment, the first interleukin domain comprises an amino acid sequence of an interleukin-15, or a variant or mutein thereof.

In one embodiment, the interleukin-15 domain in the fusion protein provided herein is a wide-type interleukin-15 domain. In another embodiment, the interleukin-15 domain in the fusion protein provided herein is a wild-type human interleukin-15 domain. In yet another embodiment, the interleukin-15 domain in the fusion protein provided herein is an interleukin-15 variant. In still another embodiment, the interleukin-15 domain in the fusion protein provided herein is an interleukin-15 mutein.

In certain embodiments, the interleukin-15 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 172.

In certain embodiments, the interleukin-15 domain in the fusion protein provided herein comprises an amino acid sequence that is no less than about 70% identical to an amino acid sequence of SEQ ID NO: 172. In certain embodiments, the interleukin-15 domain in the fusion protein provided herein comprises an amino acid sequence that is no less than about 75% identical to an amino acid sequence of SEQ ID NO: 172. In certain embodiments, the interleukin-15 domain in the fusion protein provided herein comprises an amino acid sequence that is no less than about 80% identical to an amino acid sequence of SEQ ID NO: 172. In certain embodiments, the interleukin-15 domain in the fusion protein provided herein comprises an amino acid sequence that is no less than about 85% identical to an amino acid sequence of SEQ ID NO: 172. In certain embodiments, the interleukin-15 domain in the fusion protein provided herein comprises an amino acid sequence that is no less than about 90% identical to an amino acid sequence of SEQ ID NO: 172. In certain embodiments, the interleukin-15 domain in the fusion protein provided herein comprises an amino acid sequence that is no less than about 91% identical to an amino acid sequence of SEQ ID NO: 172. In certain embodiments, the interleukin-15 domain in the fusion protein provided herein comprises an amino acid sequence that is no less than about 92% identical to an amino acid sequence of SEQ ID NO: 172. In certain embodiments, the interleukin-15 domain in the fusion protein provided herein comprises an amino acid sequence that is no less than about 93% identical to an amino acid sequence of SEQ ID NO: 172. In certain embodiments, the interleukin-15 domain in the fusion protein provided herein comprises an amino acid sequence that is no less than about 94% identical to an amino acid sequence of SEQ ID NO: 172. In certain embodiments, the interleukin-15 domain in the fusion protein provided herein comprises an amino acid sequence that is no less than about 95% identical to an amino acid sequence of SEQ ID NO: 172. In certain embodiments, the interleukin-15 domain in the fusion protein provided herein comprises an amino acid sequence that is no less than about 96% identical to an amino acid sequence of SEQ ID NO: 172. In certain embodiments, the interleukin-15 domain in the fusion protein provided herein comprises an amino acid sequence that is no less than about 97% identical to an amino acid sequence of SEQ ID NO: 172. In certain embodiments, the interleukin-15 domain in the fusion protein provided herein comprises an amino acid sequence that is no less than about 98% identical to an amino acid sequence of SEQ ID NO: 172. In certain embodiments, the interleukin-15 domain in the fusion protein provided herein comprises an amino acid sequence that is no less than about 99% identical to an amino acid sequence of SEQ ID NO: 172.

In certain embodiments, the interleukin-15 domain in the fusion protein provided herein is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 172.

In certain embodiments, the interleukin-15 domain in the fusion protein provided herein is no less than about 70% identical to an amino acid sequence of SEQ ID NO: 172. In certain embodiments, the interleukin-15 domain in the fusion protein provided herein is no less than about 75% identical to an amino acid sequence of SEQ ID NO: 172. In certain embodiments, the interleukin-15 domain in the fusion protein provided herein is no less than about 80% identical to an amino acid sequence of SEQ ID NO: 172. In certain embodiments, the interleukin-15 domain in the fusion protein provided herein is no less than about 85% identical to an amino acid sequence of SEQ ID NO: 172. In certain embodiments, the interleukin-15 domain in the fusion protein provided herein is no less than about 90% identical to an amino acid sequence of SEQ ID NO: 172. In certain embodiments, the interleukin-15 domain in the fusion protein provided herein is no less than about 91% identical to an amino acid sequence of SEQ ID NO: 172. In certain embodiments, the interleukin-15 domain in the fusion protein provided herein is no less than about 92% identical to an amino acid sequence of SEQ ID NO: 172. In certain embodiments, the interleukin-15 domain in the fusion protein provided herein is no less than about 93% identical to an amino acid sequence of SEQ ID NO: 172. In certain embodiments, the interleukin-15 domain in the fusion protein provided herein is no less than about 94% identical to an amino acid sequence of SEQ ID NO: 172. In certain embodiments, the interleukin-15 domain in the fusion protein provided herein is no less than about 95% identical to an amino acid sequence of SEQ ID NO: 172. In certain embodiments, the interleukin-15 domain in the fusion protein provided herein is no less than about 96% identical to an amino acid sequence of SEQ ID NO: 172. In certain embodiments, the interleukin-15 domain in the fusion protein provided herein is no less than about 97% identical to an amino acid sequence of SEQ ID NO: 172. In certain embodiments, the interleukin-15 domain in the fusion protein provided herein is no less than about 98% identical to an amino acid sequence of SEQ ID NO: 172. In certain embodiments, the interleukin-15 domain in the fusion protein provided herein is no less than about 99% identical to an amino acid sequence of SEQ ID NO: 172.

In yet another embodiment, provided herein is a fusion protein comprising an interleukin-2 domain, an interleukin-21 domain, and a half-life extension domain.

In certain embodiments, the half-life extension domain extends the half-life of the interleukin-2 domain and/or the interleukin-21 domain in vivo as compared to a wild-type interleukin-2 of SEQ ID NO: 1 or a wide-type interleukin-21 of SEQ ID NO: 156, respectively. In certain embodiments, the half-life extension domain extends the half-life of the interleukin-2 domain in vivo as compared to a wild-type interleukin-2 of SEQ ID NO: 1. In certain embodiments, the half-life extension domain extends the half-life of the interleukin-21 domain in vivo as compared to a wild-type interleukin-21 of SEQ ID NO: 156. In certain embodiments, the half-life extension domain extends the half-life of the interleukin-2 domain and the interleukin-21 domain in vivo as compared to a wild-type interleukin-2 of SEQ ID NO: 1 or a wide-type interleukin-21 of SEQ ID NO: 156, respectively.

In yet another embodiment, provided herein is a fusion protein comprising an interleukin-2 domain, an interleukin-21 domain, and an albumin binding domain.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker.

In one embodiment, the fusion protein provided herein consists of one interleukin-2 domain, one interleukin-21 domain, and one albumin binding domain.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly.

In one embodiment, the fusion protein provided herein consists of one interleukin-2 domain, one interleukin-21 domain, one albumin binding domain, and one peptide linker.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker.

In one embodiment, the albumin binding domain is an antibody or a fragment thereof that binds to an albumin. In another embodiment, the albumin binding domain is an antibody or a fragment thereof that binds to a human serum albumin (HSA).

In certain embodiments, the albumin binding domain binds to an HSA with a $K_d$ ranging from about 10 pM to about 1,000 nM. In certain embodiments, the albumin binding domain binds to an HSA with a $K_d$ ranging from about 1 nM to about 500 nM. In certain embodiments, the albumin binding domain binds to an HSA with a $K_d$ ranging from about 1 nM to about 200 nM. In certain embodiments, the albumin binding domain binds to an HSA with a $K_d$ ranging from about 1 nM to about 100 nM.

In one embodiment, the albumin binding domain is an antibody or a fragment thereof, comprising: (i) complementarity determining region 1 (CDR1) of SEQ ID NO: 101, complementarity determining region 2 (CDR2) of SEQ ID NO: 102, and complementarity determining region 3 (CDR3) of SEQ ID NO: 103; or (ii) CDR1 of SEQ ID NO: 109, CDR2 of SEQ ID NO: 110, and CDR3 of SEQ ID NO: 111. In another embodiment, the albumin binding domain comprises CDR1 of SEQ ID NO: 101, CDR2 of SEQ ID NO: 102, and CDR3 of SEQ ID NO: 103. In yet another embodiment, the albumin binding domain comprises CDR1 of SEQ ID NO: 109, CDR2 of SEQ ID NO: 110, and CDR3 of SEQ ID NO: 111. In certain embodiments, the CDRs provided herein are numbered using the IMGT numbering system. In yet another embodiment, the albumin binding domain has an amino acid sequence of SEQ ID NO: 108 or 115. In yet another embodiment, the albumin binding domain has an amino acid sequence of SEQ ID NO: 108. In still another embodiment, the albumin binding domain has an amino acid sequence of SEQ ID NO: 115.

In certain embodiments, the albumin binding domain has an amino acid sequence of one of anti-HSA antibodies disclosed in WO 2019/246003 A1 or WO 2019/246004 A1, the disclosure of each of which is incorporated herein by reference in its entirety.

In certain embodiments, the antibody or a fragment thereof is a human antibody. In certain embodiments, the antibody or a fragment thereof is a humanized antibody.

In another embodiment, the albumin binding domain is a single domain antibody (sdAb) that binds to an albumin. In certain embodiments, the albumin binding domain is an sdAb that binds to an HSA.

In certain embodiments, the sdAb binds to an HSA with a $K_d$ ranging from about 10 pM to about 1,000 nM. In certain embodiments, the sdAb binds to an HSA with a $K_d$ ranging from about 1 nM to about 500 nM. In certain embodiments, the sdAb binds to an HSA with a $K_d$ ranging from about 1 nM to about 200 nM. In certain embodiments, the sdAb binds to an HSA with a $K_d$ ranging from about 1 nM to about 100 nM.

In one embodiment, the sdAb comprises: (i) CDR1 of SEQ ID NO: 101, CDR2 of SEQ ID NO: 102, and CDR3 of SEQ ID NO: 103; or (ii) CDR1 of SEQ ID NO: 109, CDR2 of SEQ ID NO: 110, and CDR3 of SEQ ID NO: 111. In certain embodiments, the CDRs provided herein are numbered using the IMGT numbering system. In another embodiment, the sdAb comprises CDR1 of SEQ ID NO: 101, CDR2 of SEQ ID NO: 102, and CDR3 of SEQ ID NO: 103. In yet another embodiment, the sdAb comprises CDR1 of SEQ ID NO: 109, CDR2 of SEQ ID NO: 110, and CDR3 of SEQ ID NO: 111.

In one embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 104 or 112;
FR2 is an amino acid sequence of SEQ ID NO: 105 or 113;
FR3 is an amino acid sequence of SEQ ID NO: 106; and
FR4 is an amino acid sequence of SEQ ID NO: 107 or 114.

In another embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 104;
FR2 is an amino acid sequence of SEQ ID NO: 105;
FR3 is an amino acid sequence of SEQ ID NO: 106; and
FR3 is an amino acid sequence of SEQ ID NO: 107.

In yet another embodiment, the sdAb has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 112;
FR2 is an amino acid sequence of SEQ ID NO: 113;
FR3 is an amino acid sequence of SEQ ID NO: 106; and
FR3 is an amino acid sequence of SEQ ID NO: 114.

In one embodiment, the sdAb has an amino acid sequence of SEQ ID NO: 108 or 115. In another embodiment, the sdAb has an amino acid sequence of SEQ ID NO: 108. In yet another embodiment, the sdAb has an amino acid sequence of SEQ ID NO: 115.

In certain embodiments, the sdAb has an amino acid sequence of one of anti-HSA sdAbs disclosed in WO 2019/246003 A1 or WO 2019/246004 A1, the disclosure of each of which is incorporated herein by reference in its entirety.

In certain embodiments, the sdAb is a human antibody. In certain embodiments, the sdAb is a humanized antibody.

In yet another embodiment, provided herein is a fusion protein comprising an interleukin-2 domain, an interleukin-21 domain, and an albumin binding domain; wherein the albumin binding domain is an sdAb.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker; and wherein the albumin binding domain is an sdAb.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker; and wherein the albumin binding domain is an sdAb.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is an sdAb.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker; and wherein the albumin binding domain is an sdAb.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly; and wherein the albumin binding domain is an sdAb.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker; and wherein the albumin binding domain is an sdAb.

In one embodiment, the fusion protein provided herein consists of one interleukin-2 domain, one interleukin-21 domain, and one albumin binding domain; wherein the albumin binding domain is an sdAb.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; wherein the albumin binding domain is an sdAb.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly; wherein the albumin binding domain is an sdAb.

In one embodiment, the fusion protein provided herein consists of one interleukin-2 domain, one interleukin-21 domain, one albumin binding domain, and one peptide linker; wherein the albumin binding domain is an sdAb.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is an sdAb.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is an sdAb.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly; and wherein the albumin binding domain is an sdAb.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker; and wherein the albumin binding domain is an sdAb.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker; and wherein the albumin binding domain is an sdAb.

In yet another embodiment, the albumin binding domain is a $V_HH$ single domain antibody that binds to an albumin. In certain embodiments, the albumin binding domain is $V_HH$ single domain antibody that binds to an HSA.

In certain embodiments, the $V_HH$ single domain antibody binds to an HSA with a $K_d$ ranging from about 10 pM to about 1,000 nM. In certain embodiments, the $V_HH$ single domain antibody binds to an HSA with a $K_d$ ranging from about 1 nM to about 500 nM. In certain embodiments, the $V_HH$ single domain antibody binds to an HSA with a $K_d$ ranging from about 1 nM to about 200 nM. In certain embodiments, the $V_HH$ single domain antibody binds to an HSA with a $K_d$ ranging from about 1 nM to about 100 nM.

In one embodiment, the $V_HH$ single domain antibody comprises: (i) heavy chain CDR1 of SEQ ID NO: 101, heavy chain CDR2 of SEQ ID NO: 102, and heavy chain CDR3 of SEQ ID NO: 103; or (ii) heavy chain CDR1 of SEQ ID NO: 109, heavy chain CDR2 of SEQ ID NO: 110, and heavy chain CDR3 of SEQ ID NO: 111. In certain embodiments, the CDRs provided herein are numbered using the IMGT numbering system. In another embodiment, the $V_HH$ single domain antibody comprises heavy chain CDR1 of SEQ ID NO: 101, heavy chain CDR2 of SEQ ID NO: 102, and heavy chain CDR3 of SEQ ID NO: 103. In yet another embodiment, the $V_HH$ single domain antibody comprises heavy chain CDR1 of SEQ ID NO: 109, heavy chain CDR2 of SEQ ID NO: 110, and heavy chain CDR3 of SEQ ID NO: 111.

In one embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 104 or 112;
FR2 is an amino acid sequence of SEQ ID NO: 105 or 113;
FR3 is an amino acid sequence of SEQ ID NO: 106; and
FR4 is an amino acid sequence of SEQ ID NO: 107 or 114.

In another embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 104;
FR2 is an amino acid sequence of SEQ ID NO: 105;
FR3 is an amino acid sequence of SEQ ID NO: 106; and
FR4 is an amino acid sequence of SEQ ID NO: 107.

In yet another embodiment, the $V_HH$ single domain antibody has the structure of FR1-CDR1-FR2-CDR2-FR3-CDR3-FR4, wherein:
CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
FR1 is an amino acid sequence of SEQ ID NO: 112;
FR2 is an amino acid sequence of SEQ ID NO: 113;
FR3 is an amino acid sequence of SEQ ID NO: 106; and
FR4 is an amino acid sequence of SEQ ID NO: 114.

In one embodiment, the $V_HH$ single domain antibody has an amino acid sequence of SEQ ID NO: 108 or 115. In another embodiment, the $V_HH$ single domain antibody has an amino acid sequence of SEQ ID NO: 108. In yet another embodiment, the $V_HH$ single domain antibody has an amino acid sequence of SEQ ID NO: 115.

In certain embodiments, the $V_HH$ single domain antibody has an amino acid sequence of one of $V_HH$ single domain antibodies disclosed in WO 2019/246003 A1 or WO 2019/246004 A1, the disclosure of each of which is incorporated herein by reference in its entirety.

In certain embodiments, the $V_HH$ single domain antibody is a human antibody. In certain embodiments, the $V_HH$ single domain antibody is a humanized antibody.

In yet another embodiment, provided herein is a fusion protein comprising an interleukin-2 domain, an interleukin-21 domain, and an albumin binding domain; wherein the albumin binding domain is a $V_HH$ single domain antibody.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker; and wherein the albumin binding domain is a $V_HH$ single domain antibody.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker; and wherein the albumin binding domain is a $V_HH$ single domain antibody.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker; and wherein the albumin binding domain is a $V_HH$ single domain antibody.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly; and wherein the albumin binding domain is a $V_HH$ single domain antibody.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker; and wherein the albumin binding domain is a $V_HH$ single domain antibody.

In one embodiment, the fusion protein provided herein consists of one interleukin-2 domain, one interleukin-21 domain, and one albumin binding domain; and wherein the albumin binding domain is a $V_HH$ single domain antibody.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is a $V_HH$ single domain antibody.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly; and wherein the albumin binding domain is a $V_HH$ single domain antibody.

In one embodiment, the fusion protein provided herein consists of one interleukin-2 domain, one interleukin-21 domain, one albumin binding domain, and one peptide linker; wherein the albumin binding domain is a $V_HH$ single domain antibody.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is a $V_HH$ single domain antibody.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is a $V_HH$ single domain antibody.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly; and wherein the albumin binding domain is a $V_HH$ single domain antibody.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker; and wherein the albumin binding domain is a $V_HH$ single domain antibody.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker; and wherein the albumin binding domain is a $V_HH$ single domain antibody.

In still another embodiment, provided herein is a fusion protein comprising an interleukin-2 domain, an interleukin-21 domain, and an Fc domain.

In one embodiment, the fusion protein provided herein comprises an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the C-terminus of the interleukin-21 domain is connected to the N-terminus of the second peptide chain of the Fc domain directly or via the second peptide linker.

In another embodiment, the fusion protein provided herein comprises an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the N-terminus of the interleukin-21 domain is connected to the C-terminus of the second peptide chain of the Fc domain directly or via the second peptide linker.

In yet another embodiment, the fusion protein provided herein comprises an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the N-terminus of the interleukin-21 domain is connected to the C-terminus of the second peptide chain of the Fc domain directly or via the second peptide linker.

In yet another embodiment, the fusion protein provided herein comprises an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the C-terminus of the interleukin-21 domain is connected to the N-terminus of the second peptide chain of the Fc domain directly or via the second peptide linker.

In yet another embodiment, the fusion protein provided herein comprises first and second interleukin-2 domains, an interleukin-21 domain, an Fc domain having first and second peptide chains, and optionally a first, second, and third peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; and the N-terminus of the interleukin-21 domain is connected to the C-terminus of the first peptide chain of the Fc domain directly or via the third peptide linker.

In yet another embodiment, the fusion protein provided herein comprises first and second interleukin-2 domains, an interleukin-21 domain, an Fc domain having first and second peptide chains, and optionally a first, second, and third peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; and the C-terminus of the interleukin-21 domain is connected to the N-terminus of the first peptide chain of the Fc domain directly or via the third peptide linker.

In yet another embodiment, provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; the N-terminus of the first interleukin-21 domain is connected to the C-terminus of the first peptide chain of the Fc domain directly or via the third peptide linker; and the N-terminus of the second interleukin-21 domain is connected to the C-terminus of the second peptide chain of the Fc domain directly or via the fourth peptide linker.

In yet another embodiment, provided herein is a fusion protein comprising first and second interleukin-2 domains, first and second interleukin-21 domains, an Fc domain having first and second peptide chains, and optionally a first, second, third, and fourth peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; the C-terminus of the first interleukin-21 domain is connected to the N-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

In still another embodiment, provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the N-terminus of the second interleukin-2 domain is connected to the C-terminus of the second peptide chain of the Fc domain directly or via the second peptide linker; the N-terminus of the first interleukin-21 domain is connected to the C-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

In one embodiment, the Fc domain is a hIgG1 Fc domain or a mutein thereof, or a fragment thereof. In another embodiment, the Fc domain is a hIgG1 Fc chain 1 or a mutein thereof, or a fragment thereof. In yet another embodiment, the Fc domain is a hIgG1 Fc chain 2 or a mutein thereof, or a fragment thereof. In another embodiment, the Fc domain is a hIgG2 Fc domain or a mutein thereof, or a fragment thereof. In still another embodiment, the Fc domain is a hIgG4 Fc domain or a mutein thereof, or a fragment thereof.

In one embodiment, the Fc domain comprises an amino acid sequence of SEQ ID NO: 116, 117, 118, 119, 120, 121, 122, or 123. In yet another embodiment, the Fc domain comprises an amino acid sequence of SEQ ID NO: 116. In another embodiment, the Fc domain comprises an amino acid sequence of SEQ ID NO: 117. In yet another embodiment, the Fc domain comprises an amino acid sequence of SEQ ID NO: 118. In yet another embodiment, the Fc domain comprises an amino acid sequence of SEQ ID NO: 119. In yet another embodiment, the Fc domain comprises an amino acid sequence of SEQ ID NO: 120. In yet another embodiment, the Fc domain comprises an amino acid sequence of SEQ ID NO: 121. In yet another embodiment, the Fc domain comprises an amino acid sequence of SEQ ID NO: 122. In still another embodiment, the Fc domain comprises an amino acid sequence of SEQ ID NO: 123.

In one embodiment, the Fc domain comprises a pair of chains in a knobs-in-holes configuration.

In one embodiment, the interleukin-2 domain in the fusion protein provided herein comprises an amino acid sequence of a wide-type interleukin-2. In another embodiment, the interleukin-2 domain in the fusion protein provided herein comprises an amino acid sequence of a wild-type human interleukin-2.

In one embodiment, the interleukin-2 domain in the fusion protein provided herein has an amino acid sequence of SEQ ID NO: 1, 2, 3, 4, or 5. In another embodiment, the interleukin-2 domain in the fusion protein provided herein has an amino acid sequence of SEQ ID NO: 1. In yet another embodiment, the interleukin-2 domain in the fusion protein provided herein has an amino acid sequence of SEQ ID NO: 2. In yet another embodiment, the interleukin-2 domain in the fusion protein provided herein has an amino acid sequence of SEQ ID NO: 3. In yet another embodiment, the interleukin-2 domain in the fusion protein provided herein has an amino acid sequence of SEQ ID NO: 4. In still another embodiment, the interleukin-2 domain in the fusion protein provided herein has an amino acid sequence of SEQ ID NO: 5.

In one embodiment, the interleukin-2 domain in the fusion protein provided herein is glycosylated. In another embodiment, the interleukin-2 domain in the fusion protein provided herein is N-glycosylated.

In one embodiment, the fusion protein containing the N-glycosylated interleukin-2 domain has a reduced binding affinity to an interleukin-2 receptor-α (IL-2Rα) chain as compared to a wild-type interleukin-2. In certain embodiments, the binding affinity of the fusion protein to an interleukin-2 receptor-α (IL-2Rα) is measured by its association constant ($K_a$), which is the inverse of its dissociation constant ($K_d$).

In certain embodiments, the fusion protein containing the N-glycosylated interleukin-2 domain has a $K_d$ to the IL-2Rα of no less than about 2 times, no less than about 5 times, no less than about 10 times, no less than about 100 times, or no less than about 1,000 times higher than that of the wild-type interleukin-2 to the IL-2Rα. In one embodiment, the fusion protein containing the N-glycosylated interleukin-2 domain has a $K_d$ to the IL-2Rα of no less than about 2 times higher than that of the wild-type interleukin-2 to the IL-2Rα. In another embodiment, the fusion protein containing the N-glycosylated interleukin-2 domain has a $K_d$ to the IL-2Rα of no less than about 5 times higher than that of the wild-type interleukin-2 to the IL-2Rα. In yet another embodiment, the fusion protein containing the N-glycosylated interleukin-2 domain has a $K_d$ to the IL-2Rα of no less than about 10 times higher than that of the wild-type interleukin-2 to the IL-2Rα. In yet another embodiment, the fusion protein containing the N-glycosylated interleukin-2 domain has a $K_d$ to the IL-2Rα of no less than about 100 times higher than that of the wild-type interleukin-2 to the IL-2Rα. In still another embodiment, the fusion protein containing the N-glycosylated interleukin-2 domain has a $K_d$ to the IL-2Rα of no less than about 1,000 times higher than that of the wild-type interleukin-2 to the IL-2Rα.

In one embodiment, the wild-type interleukin-2 is a human wild-type interleukin-2. In another embodiment, the human wild-type interleukin-2 has an amino acid sequence of SEQ ID NO: 1, 2, 3, 4, or 5. In yet another embodiment, the human wild-type interleukin-2 has an amino acid sequence of SEQ ID NO: 1. In yet another embodiment, the human wild-type interleukin-2 has an amino acid sequence of SEQ ID NO: 2. In yet another embodiment, the human wild-type interleukin-2 has an amino acid sequence of SEQ ID NO: 3. In yet another embodiment, the human wild-type interleukin-2 has an amino acid sequence of SEQ ID NO: 4. In still another embodiment, the human wild-type interleukin-2 has an amino acid sequence of SEQ ID NO: 5.

In one embodiment, the fusion protein containing the N-glycosylated interleukin-2 domain has a $K_d$ to an IL-2Rα of no less than about 20 nM, no less than about 50 nM, no less than about 100 nM, no less than about 1 μM, no less than about 10 μM, no less than about 100 μM, or no less than about 1 mM. In certain embodiments, the fusion protein containing the N-glycosylated interleukin-2 domain has a $K_d$ to the IL-2Rα of no less than about 20 nM. In certain embodiments, the fusion protein containing the N-glycosylated interleukin-2 domain has a $K_d$ to the IL-2Rα of no less than about 50 nM. In certain embodiments, the fusion protein containing the N-glycosylated interleukin-2 domain has a $K_d$ to the IL-2Rα of no less than about 100 nM. In certain embodiments, the fusion protein containing the N-glycosylated interleukin-2 domain has a $K_d$ to the IL-2Rα of no less than about 1 M. In certain embodiments, the fusion protein containing the N-glycosylated interleukin-2 domain has a $K_d$ to the IL-2Rα receptor (CD25) of no less than about 10 μM. In certain embodiments, the fusion protein containing the N-glycosylated interleukin-2 domain has a $K_d$ to the IL-2Rα of no less than about 100 μM. In certain embodiments, the fusion protein containing the N-glycosylated interleukin-2 domain has a $K_d$ to the IL-2Rα of no less than about 1 mM. In certain embodiments, the fusion protein containing the N-glycosylated interleukin-2 domain has no measurable binding to the IL-2Rα. In certain embodiments, the fusion protein containing the N-glycosylated interleukin-2 domain has no detectable binding to the IL-2Rα as measured with a surface plasmon resonance (SPR) method. In certain embodiments, the fusion protein containing the N-glycosylated interleukin-2 domain has no detectable binding to the IL-2Rα as measured with bio-layer interferometry (BLI).

In yet another embodiment, the fusion protein containing the N-glycosylated interleukin-2 domain has a selectivity for an IL-2Rβ over an IL-2Rα; wherein the selectivity is no greater than about 1, no greater than about 0.5, no greater than about 0.2, no greater than about 0.1, no greater than about 0.01, or no greater than about 0.001; and wherein the selectivity is measured as a ratio of a $K_d$ of the fusion protein to the IL-2Rβ over a $K_d$ of the fusion protein to the IL-2Rα. In certain embodiments, the fusion protein containing the N-glycosylated interleukin-2 domain has a selectivity of no greater than about 1. In certain embodiments, the fusion protein containing the N-glycosylated interleukin-2 domain has a selectivity of no greater than about 0.5. In certain embodiments, the fusion protein containing the N-glycosylated interleukin-2 domain has a selectivity of no greater than about 0.2. In certain embodiments, the fusion protein containing the N-glycosylated interleukin-2 domain has a selectivity of no greater than about 0.1. In certain embodiments, the fusion protein containing the N-glycosylated interleukin-2 domain has a selectivity of no greater than about 0.01. In certain embodiments, the fusion protein containing the N-glycosylated interleukin-2 domain has a selectivity of no greater than about 0.001.

In one embodiment, the IL-2Rα is a human IL-2Rα. In another embodiment, the human IL-2Rα has an amino acid sequence of SEQ ID NO: 98.

In one embodiment, the IL-2Rβ is a human IL-2Rβ. In another embodiment, the human IL-2Rβ has an amino acid sequence of SEQ ID NO: 99.

In one embodiment, the dissociation constant of the fusion protein to an IL-2Rα is determined with a surface plasmon resonance (SPR) method. In another embodiment, the dissociation constant of the fusion protein to an IL-2Rα is determined with a BIACORE® assay. In yet another embodiment, the dissociation constant of the fusion protein to an IL-2Rα is determined with bio-layer interferometry (BLI). In still another embodiment, the dissociation constant of the fusion protein to an IL-2Rα is determined with an OCTET® assay.

In one embodiment, the dissociation constant of the fusion protein to an IL-2Rβ is determined with a SPR method. In another embodiment, the dissociation constant of the fusion protein to an IL-2Rβ is determined with a BIACORE® assay. In yet another embodiment, the dissociation constant of the fusion protein to an IL-2Rβ is determined with BLI. In still another embodiment, the dissociation constant of the fusion protein to an IL-2Rβ is determined with an OCTET® assay.

In yet another embodiment, the fusion protein containing the N-glycosylated interleukin-2 domain has a selectivity for an IL-2Rβ and IL-2Rγ complex over an IL-2Rα; wherein the selectivity is no greater than about 0.01 or no greater than about 0.001; and wherein the selectivity is measured as a ratio of a $K_d$ of the fusion protein to the IL-2Rβ and IL-2Rγ complex over a $K_d$ of the fusion protein to the IL-2Rα. In certain embodiments, the fusion protein containing the N-glycosylated interleukin-2 domain has a selectivity of no greater than about 0.01. In certain embodiments, the fusion protein containing the N-glycosylated interleukin-2 domain has a selectivity of no greater than about 0.001. In one embodiment, the dissociation constants of the fusion protein to the IL-2Rα and the IL-2Rβ and IL-2Rγ complex are determined as described in Richert et al., *J. Mol. Biol.* 2004, 339, 1115-9.

In one embodiment, the IL-2Rγ is a human IL-2Rγ. In another embodiment, the human IL-2Rγ has an amino acid sequence of SEQ ID NO: 100.

In yet another embodiment, the N-glycosylated interleukin-2 domain in the fusion protein provided herein is an N-glycosylated polypeptide of 133 amino acids.

In yet another embodiment, the N-glycosylated interleukin-2 domain in the fusion protein provided herein comprises one, two, three, four, or more substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5.

In one embodiment, the N-glycosylated interleukin-2 domain in the fusion protein provided herein comprises an amino acid substitution at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the N-glycosylated interleukin-2 domain in the fusion protein provided herein comprises an amino acid substitution at position K35, M39, A73, or D109 as set forth in an amino acid sequence of SEQ ID NO: 1, 2, 3, 4, or 5.

In another embodiment, the N-glycosylated interleukin-2 domain in the fusion protein provided herein comprises two substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises two substitutions at position P34, K35, L36, T37, R38, L40, T41, F42, K43, F44, Y45, M46, P47, E61, E62, L63, P65, L66, E67, E68, V69, L70, N71, L72, Q74, Y107, D109, and/or T111 as set forth in an amino acid sequence of SEQ ID NO: 1, 2, 3, 4, or 5.

In yet another embodiment, the N-glycosylated interleukin-2 domain in the fusion protein provided herein comprises three substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises three substitutions at position R38, L40, F42, Y45, E61, E62, K64, P65, and/or L66 as set forth in an amino acid sequence of SEQ ID NO: 1, 2, 3, 4, or 5.

In yet another embodiment, the N-glycosylated interleukin-2 domain in the fusion protein provided herein comprises four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises four substitutions at position R38, L40, F42, and Y45 as set forth in an amino acid sequence of SEQ ID NO: 1, 2, 3, 4, or 5.

In yet another embodiment, the N-glycosylated interleukin-2 domain in the fusion protein provided herein comprises one, two, three, or four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In one embodiment, the N-glycosylated interleukin-2 domain in the fusion protein provided herein comprises one substitution selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In another embodiment, the N-glycosylated interleukin-2 domain in the fusion protein provided herein comprises two substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In yet another embodiment, the N-glycosylated interleukin-2 domain in the fusion protein provided herein comprises the substitutions of R38N and Y45N as set forth in an amino acid sequence of SEQ ID NO: 1, 2, 3, 4, or 5. In yet another embodiment, the N-glycosylated interleukin-2 domain in the fusion protein provided herein comprises three substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In still another embodiment, the N-glycosylated interleukin-2 domain in the fusion protein provided herein comprises four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5.

In yet another embodiment, the N-glycosylated interleukin-2 domain in the fusion protein provided herein comprises one, two, three, or more N-glycosylation sites, each independently having an amino acid sequence of NXT or NXS, wherein each X is independently A, C, D, E, F, G, H, I, K, L, M, N, Q, R, S, T, V, W, or Y.

In one embodiment, the N-glycosylated interleukin-2 domain in the fusion protein provided herein comprises an N-glycosylation site having an amino acid sequence of NXT or NXS, wherein each X is independently A, C, D, E, F, G, H, I, K, L, M, N, Q, R, S, T, V, W, or Y. In another embodiment, the N-glycosylated interleukin-2 domain in the fusion protein provided herein comprises two N-glycosylation sites, each independently having an amino acid sequence of NXT or NXS, wherein each X is independently A, C, D, E, F, G, H, I, K, L, M, N, Q, R, S, T, V, W, or Y. In yet another embodiment, the N-glycosylated interleukin-2 domain in the fusion protein provided herein comprises an N-glycosylation site of NFT and an N-glycosylation site of NMT. In still another embodiment, the N-glycosylated interleukin-2 domain in the fusion protein provided herein comprises three N-glycosylation sites, each independently having an amino acid sequence of NXT or NXS, wherein each X is independently A, C, D, E, F, G, H, I, K, L, M, N, Q, R, S, T, V, W, or Y.

In one embodiment, each X is independently A, C, D, E, F, G, H, I, K, M, N, Q, R, S, T, V, W, or Y. In another embodiment, each X is independently A, C, D, G, H, K, M, N, Q, R, S, T, V, W, or Y. In yet another embodiment, each X is independently A, E, F, K, L, M, R, V, W, or Y. In still another embodiment, each X is independently F or M.

In yet another embodiment, the N-glycosylated interleukin-2 domain in the fusion protein provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS.

In one embodiment, the N-glycosylated interleukin-2 domain in the fusion protein provided herein comprises an N-glycosylation site having an amino acid sequence of NAT or NAS. In another embodiment, the N-glycosylated interleukin-2 domain in the fusion protein provided herein comprises an N-glycosylation site having an amino acid sequence of NET or NES. In yet another embodiment, the N-glycosylated interleukin-2 domain in the fusion protein provided herein comprises an N-glycosylation site having an amino acid sequence of NFT or NFS. In yet another embodiment, the N-glycosylated interleukin-2 domain in the fusion protein provided herein comprises an N-glycosylation site having an amino acid sequence of NKT or NKS. In yet another embodiment, the N-glycosylated interleukin-2 domain in the fusion protein provided herein comprises an N-glycosylation site having an amino acid sequence of NLT or NLS. In yet another embodiment, the N-glycosylated interleukin-2 domain in the fusion protein provided herein comprises an N-glycosylation site having an amino acid sequence of NMT or NMS. In yet another embodiment, the N-glycosylated interleukin-2 domain in the fusion protein provided herein comprises an N-glycosylation site having an amino acid sequence of NRT or NRS. In yet another embodiment, the N-glycosylated interleukin-2 domain in the fusion protein provided herein comprises an N-glycosylation site having an amino acid sequence of NVT or NVS. In yet another embodiment, the N-glycosylated interleukin-2 domain in the fusion protein provided herein comprises an N-glycosylation site having an amino acid sequence of NWT or NWS. In still another embodiment, the N-glycosylated interleukin-2 domain in the fusion protein provided herein comprises an N-glycosylation site having an amino acid sequence of NYT or NYS.

In yet another embodiment, the N-glycosylated interleukin-2 domain in the fusion protein provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS, each independently starting at position 34, 35, 37, 38, 39, 41, 42, 43, 44, 45, 61, 62, 64, 65, 66, 68, 69, 71, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an N-glycosylation site having an amino acid sequence of NKT or NKS, each independently starting at position 34 or 42 as set forth in an amino acid sequence of SEQ ID NO: 1, 2, 3, 4, or 5.

In another embodiment, the N-glycosylated interleukin-2 domain in the fusion protein provided herein comprises an N-glycosylation site having an amino acid sequence of NLT or NLS, each independently starting at position 35, 39, 62, 65, 69, or 71 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NRT or NRS, each independently starting at position 37 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NMT or NMS, each independently starting at position 38 or 45 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NFT or NFS, each independently starting at position 41 or 43 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NYT or NYS, each independently starting at position 44 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NET or NES, each independently starting at position 61, 66, or 109 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NAT or NAS, each independently starting at position 64, 72, or 107 as set forth in an amino acid sequence of SEQ ID NO: 1, 2, 3, 4, or 5.

In still another embodiment, the N-glycosylated interleukin-2 domain in the fusion protein provided herein comprises an N-glycosylation site having an amino acid sequence of NVT or NVS, each independently starting at position 68 as set forth in an amino acid sequence of SEQ ID NO: 1, 2, 3, 4, or 5.

In yet another embodiment, the N-glycosylated interleukin-2 domain in the fusion protein provided herein comprises an amino acid sequence of NA, NE, NK, NM, or NW.

In one embodiment, the N-glycosylated interleukin-2 domain in the fusion protein provided herein comprises an amino acid sequence of NA. In another embodiment, the N-glycosylated interleukin-2 domain in the fusion protein provided herein comprises an amino acid sequence of NE. In yet another embodiment, the N-glycosylated interleukin-2 domain in the fusion protein provided herein comprises an amino acid sequence of NK. In yet another embodiment, the N-glycosylated interleukin-2 domain in the fusion protein provided herein comprises an amino acid sequence of NM. In still another embodiment, the N-glycosylated interleukin-2 domain in the fusion protein provided herein comprises an amino acid sequence of NW.

In yet another embodiment, the N-glycosylated interleukin-2 domain in the fusion protein provided herein comprises an amino acid sequence of NA, NE, NK, NM, or NW, each independently starting at position 34, 38, 42, 45, 61, 64, 66, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an amino acid sequence of NK starting at position 34 or 42 as set forth in an amino acid sequence of SEQ ID NO: 1, 2, 3, 4, or 5. In another embodiment, the N-glycosylated interleukin-2 domain in the fusion protein provided herein comprises an amino acid sequence of NM starting at position 38 or 45 as set forth in an amino acid sequence of SEQ ID NO: 1, 2, 3, 4, or 5. In yet another embodiment, the N-glycosylated interleukin-2 domain in the fusion protein provided herein comprises an amino acid sequence of NE starting at position 61, 66, or 109 as set forth in an amino acid sequence of SEQ ID NO: 1, 2, 3, 4, or 5. In still another embodiment, the N-glycosylated interleukin-2 domain in the fusion protein provided herein comprises an amino acid sequence of NA starting at position 64, 72, or 107 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site that comprises an amino acid sequence of NK, NM, NE, NW, or NA.

In one embodiment, the N-glycosylated interleukin-2 domain in the fusion protein provided herein comprises an N-glycosylation site that comprises an amino acid sequence of NK. In another embodiment, the N-glycosylated interleukin-2 domain in the fusion protein provided herein comprises an N-glycosylation site that comprises an amino acid sequence of NM. In yet another embodiment, the N-glycosylated interleukin-2 domain in the fusion protein provided herein comprises an N-glycosylation site that comprises an amino acid sequence of NE. In yet another embodiment, the N-glycosylated interleukin-2 domain in the fusion protein provided herein comprises an N-glycosylation site that comprises an amino acid sequence of NW. In still another embodiment, the N-glycosylated interleukin-2 domain in the fusion protein provided herein comprises an N-glycosylation site that comprises an amino acid sequence of NA.

In yet another embodiment, the N-glycosylated interleukin-2 domain in the fusion protein provided herein comprises an N-glycosylation site that comprises an amino acid sequence of NK, NM, NE, NW, or NA, each independently starting at position 34, 38, 42, 45, 61, 64, 66, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an N-glycosylation site that comprises an amino acid sequence of NK starting at position 34 or 42 as set forth in an amino acid sequence of SEQ ID NO: 1, 2, 3, 4, or 5. In another embodiment, the N-glycosylated interleukin-2 domain in the fusion protein provided herein comprises an N-glycosylation site that comprises an amino acid sequence of NM starting at position 38 or 45 as set forth in an amino acid sequence of SEQ ID NO: 1, 2, 3, 4, or 5. In yet another embodiment, the N-glycosylated interleukin-2 domain in the fusion protein provided herein comprises an N-glycosylation site that comprises an amino acid sequence of NE starting at position 61, 66, or 109 as set forth in an amino acid sequence of SEQ ID NO: 1, 2, 3, 4, or 5. In still another embodiment, the N-glycosylated interleukin-2 domain in the fusion protein provided herein comprises an N-glycosylation site that comprises an amino acid sequence of NA starting at position 64, 72, or 107 as set forth in an amino acid sequence of SEQ ID NO: 1, 2, 3, 4, or 5.

In one embodiment, the N-glycosylated interleukin-2 domain in the fusion protein provided herein comprises an amino acid substitution P34N, wherein the asparagine at position 34 is N-glycosylated. In another embodiment, the N-glycosylated interleukin-2 domain in the fusion protein provided herein comprises an amino acid substitution K35N, wherein the asparagine at position 35 is N-glycosylated. In yet another embodiment, the N-glycosylated interleukin-2 domain in the fusion protein provided herein comprises an amino acid substitution T37N, wherein the asparagine at position 37 is N-glycosylated. In yet another embodiment, the N-glycosylated interleukin-2 domain in the fusion protein provided herein comprises an amino acid substitution R38N, wherein the asparagine at position 38 is N-glycosylated. In yet another embodiment, the N-glycosylated interleukin-2 domain in the fusion protein provided herein comprises an amino acid substitution M39N, wherein the asparagine at position 39 is N-glycosylated. In yet another embodiment, the N-glycosylated interleukin-2 domain in the fusion protein provided herein comprises an amino acid substitution T41N, wherein the asparagine at position 41 is N-glycosylated. In yet another embodiment, the N-glycosylated interleukin-2 domain in the fusion protein provided herein comprises an amino acid substitution F42N, wherein the asparagine at position 42 is N-glycosylated. In yet another embodiment, the N-glycosylated interleukin-2 domain in the fusion protein provided herein comprises an amino acid substitution K43N, wherein the asparagine at position 43 is N-glycosylated. In yet another embodiment, the N-glycosylated interleukin-2 domain in the fusion protein provided herein comprises an amino acid substitution F44N, wherein the asparagine at position 44 is N-glycosylated. In yet another embodiment, the N-glycosylated interleukin-2 domain in the fusion protein provided herein comprises an amino acid substitution Y45N, wherein the asparagine at position 45 is N-glycosylated. In yet another embodiment, the N-glycosylated interleukin-2 domain in the fusion protein provided herein comprises an amino acid substitution E61N, wherein the asparagine at position 61 is N-glycosylated. In yet another embodiment, the N-glycosylated interleukin-2 domain in the fusion protein provided herein comprises an amino acid substitution E62N, wherein the asparagine at position 62 is N-glycosylated. In yet another embodiment, the N-glycosylated interleukin-2 domain in the fusion protein provided herein comprises an amino acid substitution K64N, wherein the asparagine at position 64 is N-glycosylated. In yet another embodiment, the N-glycosylated interleukin-2 domain in the fusion protein provided herein comprises an amino acid substitution P65N, wherein the asparagine at position 65 is N-glycosylated. In yet another embodiment, the N-glycosylated interleukin-2 domain in the fusion protein provided herein comprises an amino acid substitution L66N, wherein the asparagine at position 66 is N-glycosylated. In yet another embodiment, the N-glycosylated interleukin-2 domain in the fusion protein provided herein comprises an amino acid substitution E68N, wherein the asparagine at position 68 is N-glycosylated. In yet another embodiment, the N-glycosylated interleukin-2 domain in the fusion protein provided herein comprises an amino acid substitution V69N, wherein the asparagine at position 69 is N-glycosylated. In yet another embodiment, the N-glycosylated interleukin-2 domain in the fusion protein provided herein comprises an amino acid substitution A73T or A73S, wherein the asparagine at position 71 is N-glycosylated. In yet another embodiment, the N-glycosylated interleukin-2 domain in the fusion protein provided herein comprises an amino acid substitution L72N, wherein the asparagine at position 72 is N-glycosylated. In yet another embodiment, the N-glycosylated interleukin-2 domain in the fusion protein provided herein comprises an amino acid substitution Y107N, wherein the asparagine at position 107 is N-glycosylated. In still another embodiment, the N-glycosylated interleukin-2 domain in the fusion protein provided herein comprises an amino acid substitution D109N, wherein the asparagine at position 109 is N-glycosylated.

In yet another embodiment, the N-glycosylated interleukin-2 domain in the fusion protein provided herein comprises an N-glycosylation site at an interface residue between an interleukin-2 and an interleukin-2 receptor-α (IL-2Rα) chain.

In one embodiment, the interface residue is K35, T37, R38, T41, F42, K43, F44, Y45, E61, E62, K64, P65, E68, L72, or Y107 as set forth in an amino acid sequence of SEQ ID NO: 1, 2, 3, 4, or 5. In another embodiment, the interface residue is K35 as set forth in an amino acid sequence of SEQ ID NO: 1, 2, 3, 4, or 5. In yet another embodiment, the interface residue is T37 as set forth in an amino acid sequence of SEQ ID NO: 1, 2, 3, 4, or 5. In yet another embodiment, the interface residue is R38 as set forth in an amino acid sequence of SEQ ID NO: 1, 2, 3, 4, or 5. In yet another embodiment, the interface residue is T41 as set forth in an amino acid sequence of SEQ ID NO: 1, 2, 3, 4, or 5. In yet another embodiment, the interface residue is F42 as set forth in an amino acid sequence of SEQ ID NO: 1, 2, 3, 4, or 5. In yet another embodiment, the interface residue is K43 as set forth in an amino acid sequence of SEQ ID NO: 1, 2, 3, 4, or 5. In yet another embodiment, the interface residue is F44 as set forth in an amino acid sequence of SEQ ID NO: 1, 2, 3, 4, or 5. In yet another embodiment, the interface residue is Y45 as set forth in an amino acid sequence of SEQ ID NO: 1, 2, 3, 4, or 5. In yet another embodiment, the interface residue is E61 as set forth in an amino acid sequence of SEQ ID NO: 1, 2, 3, 4, or 5. In yet another embodiment, the interface residue is E62 as set forth in an amino acid sequence of SEQ ID NO: 1, 2, 3, 4, or 5. In yet another embodiment, the interface residue is K64 as set forth in an amino acid sequence of SEQ ID NO: 1, 2, 3, 4, or 5. In yet another embodiment, the interface residue is P65 as set forth in an amino acid sequence of SEQ ID NO: 1, 2, 3, 4, or 5. In yet another embodiment, the interface residue is E68 as set forth in an amino acid sequence of SEQ ID NO: 1, 2, 3, 4, or 5. In yet another embodiment, the interface residue is L72 as set forth in an amino acid sequence of SEQ ID NO: 1, 2, 3, 4, or 5. In still another embodiment, the interface residue is Y107 as set forth in an amino acid sequence of SEQ ID NO: 1, 2, 3, 4, or 5.

In one embodiment, the N-glycosylated interleukin-2 domain in the fusion protein provided herein comprises an amino acid substitution K35N, wherein the asparagine at position 35 is N-glycosylated. In another embodiment, the N-glycosylated interleukin-2 domain in the fusion protein provided herein comprises an amino acid substitution T37N, wherein the asparagine at position 37 is N-glycosylated. In yet another embodiment, the N-glycosylated interleukin-2 domain in the fusion protein provided herein comprises an amino acid substitution R38N, wherein the asparagine at position 38 is N-glycosylated. In yet another embodiment, the N-glycosylated interleukin-2 domain in the fusion protein provided herein comprises an amino acid substitution T41N, wherein the asparagine at position 41 is N-glycosylated. In yet another embodiment, the N-glycosylated interleukin-2 domain in the fusion protein provided herein comprises an amino acid substitution F42N, wherein the asparagine at position 42 is N-glycosylated. In yet another embodiment, the N-glycosylated interleukin-2 domain in the fusion protein provided herein comprises an amino acid substitution K43N, wherein the asparagine at position 43 is N-glycosylated. In yet another embodiment, the N-glycosylated interleukin-2 domain in the fusion protein provided herein comprises an amino acid substitution F44N, wherein the asparagine at position 44 is N-glycosylated. In yet another embodiment, the N-glycosylated interleukin-2 domain in the fusion protein provided herein comprises an amino acid substitution Y45N, wherein the asparagine at position 45 is N-glycosylated. In yet another embodiment, the N-glycosylated interleukin-2 domain in the fusion protein provided herein comprises an amino acid substitution E61N, wherein the asparagine at position 61 is N-glycosylated. In yet another embodiment, the N-glycosylated interleukin-2 domain in the fusion protein provided herein comprises an amino acid substitution E62N, wherein the asparagine at position 62 is N-glycosylated. In yet another embodiment, the N-glycosylated interleukin-2 domain in the fusion protein provided herein comprises an amino acid substitution K64N, wherein the asparagine at position 64 is N-glycosylated. In yet another embodiment, the N-glycosylated interleukin-2 domain in the fusion protein provided herein comprises an amino acid substitution P65N, wherein the asparagine at position 65 is N-glycosylated. In yet another embodiment, the N-glycosylated interleukin-2 domain in the fusion protein provided herein comprises an amino acid substitution E68N, wherein the asparagine at position 68 is N-glycosylated. In yet another embodiment, the N-glycosylated interleukin-2 domain in the fusion protein provided herein comprises an amino acid substitution L72N, wherein the asparagine at position 72 is N-glycosylated. In still another embodiment, the N-glycosylated interleukin-2 domain in the fusion protein provided herein comprises an amino acid substitution Y107N, wherein the asparagine at position 107 is N-glycosylated.

In still another embodiment, the N-glycosylated interleukin-2 domain in the fusion protein provided herein comprises an N-glycosylation site at position K35, T37, R38, T41, F42, K43, F44, Y45, E61, E62, K64, P65, E68, L72, or Y107 as set forth in an amino acid sequence of SEQ ID NO: 1, 2, 3, 4, or 5.

In one embodiment, the N-glycosylated interleukin-2 domain in the fusion protein provided herein comprises an N-glycosylation site at position K35 as set forth in an amino acid sequence of SEQ ID NO: 1, 2, 3, 4, or 5. In another embodiment, the N-glycosylated interleukin-2 domain in the fusion protein provided herein comprises an N-glycosylation site at position T37 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position R38 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position T41 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position F42 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position K43 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position F44 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position Y45 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E61 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E62 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position K64 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position P65 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E68 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position L72 as set forth in an amino acid sequence of SEQ ID NO: 1, 2, 3, 4, or 5. In still another embodiment, the N-glycosylated interleukin-2 domain in the fusion protein provided herein comprises an N-glycosylation site at position Y107 as set forth in an amino acid sequence of SEQ ID NO: 1, 2, 3, 4, or 5.

In certain embodiments, the N-glycosylated interleukin-2 domain in the fusion protein provided herein comprises an amino acid sequence that is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the N-glycosylated interleukin-2 domain in the fusion protein provided herein comprises an amino acid sequence that is no less than about 80% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 85% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 90% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 91% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 92% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 93% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 94% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 95% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 96% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 97% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 98% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 99% identical to an amino acid sequence of SEQ ID NO: 1, 2, 3, 4, or 5.

In certain embodiments, the N-glycosylated interleukin-2 domain in the fusion protein provided herein is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the N-glycosylated interleukin-2 domain in the fusion protein provided herein is no less than about 80% identical to an amino acid sequence of SEQ ID NO: 1, 2, 3, 4, or 5. In certain embodiments, the N-glycosylated interleukin-2 domain in the fusion protein provided herein is no less than about 85% identical to an amino acid sequence of SEQ ID NO: 1, 2, 3, 4, or 5. In certain embodiments, the N-glycosylated interleukin-2 domain in the fusion protein provided herein is no less than about 90% identical to an amino acid sequence of SEQ ID NO: 1, 2, 3, 4, or 5. In certain embodiments, the N-glycosylated interleukin-2 domain in the fusion protein provided herein is no less than about 91% identical to an amino acid sequence of SEQ ID NO: 1, 2, 3, 4, or 5. In certain embodiments, the N-glycosylated interleukin-2 domain in the fusion protein provided herein is no less than about 92% identical to an amino acid sequence of SEQ ID NO: 1, 2, 3, 4, or 5. In certain embodiments, the N-glycosylated interleukin-2 domain in the fusion protein provided herein is no less than about 93% identical to an amino acid sequence of SEQ ID NO: 1, 2, 3, 4, or 5. In certain embodiments, the N-glycosylated interleukin-2 domain in the fusion protein provided herein is no less than about 94% identical to an amino acid sequence of SEQ ID NO: 1, 2, 3, 4, or 5. In certain embodiments, the N-glycosylated interleukin-2 domain in the fusion protein provided herein is no less than about 95% identical to an amino acid sequence of SEQ ID NO: 1, 2, 3, 4, or 5. In certain embodiments, the N-glycosylated interleukin-2 domain in the fusion protein provided herein is no less than about 96% identical to an amino acid sequence of SEQ ID NO: 1, 2, 3, 4, or 5. In certain embodiments, the N-glycosylated interleukin-2 domain in the fusion protein provided herein is no less than about 97% identical to an amino acid sequence of SEQ ID NO: 1, 2, 3, 4, or 5. In certain embodiments, the N-glycosylated interleukin-2 domain in the fusion protein provided herein is no less than about 98% identical to an amino acid sequence of SEQ ID NO: 1, 2, 3, 4, or 5. In certain embodiments, the N-glycosylated interleukin-2 domain in the fusion protein provided herein is no less than about 99% identical to an amino acid sequence of SEQ ID NO: 1, 2, 3, 4, or 5.

In certain embodiments, the N-glycosylated interleukin-2 domain in the fusion protein provided herein comprises an amino acid substitution: K35N, M39N, A73T, A73S, or D109N, as set forth in an amino acid sequence of SEQ ID NO: 1, 2, 3, 4, or 5.

In one embodiment, the N-glycosylated interleukin-2 domain in the fusion protein provided herein comprises an amino acid substitution: K35N, as set forth in an amino acid sequence of SEQ ID NO: 1, 2, 3, 4, or 5. In another embodiment, the N-glycosylated interleukin-2 domain in the fusion protein provided herein comprises an amino acid sequence of SEQ ID NO: 10, 11, 12, or 13. In yet another embodiment, the amino acid sequence of the N-glycosylated interleukin-2 domain in the fusion protein provided herein is SEQ ID NO: 10, 11, 12, or 13.

In one embodiment, the N-glycosylated interleukin-2 domain in the fusion protein provided herein comprises an amino acid substitution: M39N, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 86 or 87. In yet another embodiment, the amino acid sequence of the N-glycosylated interleukin-2 domain in the fusion protein provided herein is SEQ ID NO: 86 or 87.

In one embodiment, the N-glycosylated interleukin-2 domain in the fusion protein provided herein comprises an amino acid substitution: A73T or A73S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 70, 71, 72, or 73. In yet another embodiment, the amino acid sequence of the N-glycosylated interleukin-2 domain in the fusion protein provided herein is SEQ ID NO: 70, 71, 72, or 73.

In one embodiment, the N-glycosylated interleukin-2 domain in the fusion protein provided herein comprises an amino acid substitution: D109N, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 82, 83, 84, or 85. In yet another embodiment, the amino acid sequence of the N-glycosylated interleukin-2 domain in the fusion protein provided herein is SEQ ID NO: 82, 83, 84, or 85.

In certain embodiments, the N-glycosylated interleukin-2 domain in the fusion protein provided herein comprises a two-amino acid substitution combination selected from: (i) P34N and L36T or L36S; (ii) K35N and T37S; (iii) T37N and M39T or M39S; (iv) R38N and L40T or L40S; (v) T41N and K43T or K43S; (vi) F42N and F44T or F44S; (vii) K43N and Y45T or Y45S; (viii) F44N and M46T or M46S; (ix) Y45N and P47T or P47S; (x) E61N and L63T or L63S; (xi) E62N and K64T or K64S; (xii) P65N and E67T or E67S; (xiii) L66N and E68T or E68S; (xiv) E68N and L70T or L70S; (xv) V69N and N71T or N71S; (xvi) L72N and Q74T or Q74S; (xvii) Y107N and D109T or D109S; and (xviii) D109N and T111S; as set forth in an amino acid sequence of SEQ ID NO: 1, 2, 3, 4, or 5.

In one embodiment, the N-glycosylated interleukin-2 domain in the fusion protein provided herein comprises two amino acid substitutions: (i) P34N and (ii) L36T or L36S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 6, 7, 8, or 9. In yet another embodiment, the amino acid sequence of the N-glycosylated interleukin-2 domain in the fusion protein provided herein is SEQ ID NO: 6, 7, 8, or 9.

In one embodiment, the N-glycosylated interleukin-2 domain in the fusion protein provided herein comprises two amino acid substitutions: K35N and T37S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 11 or 13. In yet another embodiment, the amino acid sequence of the N-glycosylated interleukin-2 domain in the fusion protein provided herein is SEQ ID NO: 11 or 13.

In one embodiment, the N-glycosylated interleukin-2 domain in the fusion protein provided herein comprises two amino acid substitutions: (i) T37N and (ii) M39T or M39S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 14, 15, 16, or 17. In yet another embodiment, the amino acid sequence of the N-glycosylated interleukin-2 domain in the fusion protein provided herein is SEQ ID NO: 14, 15, 16, or 17.

In one embodiment, the N-glycosylated interleukin-2 domain in the fusion protein provided herein comprises two amino acid substitutions: (i) R38N and (ii) L40T or L40S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 18, 19, 20, or 21. In yet another embodiment, the amino acid sequence of the N-glycosylated interleukin-2 domain in the fusion protein provided herein is SEQ ID NO: 18, 19, 20, or 21.

In one embodiment, the N-glycosylated interleukin-2 domain in the fusion protein provided herein comprises two amino acid substitutions: (i) T41N and (ii) K43T or K43S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 22, 23, 24, or 25. In yet another embodiment, the amino acid sequence of the N-glycosylated interleukin-2 domain in the fusion protein provided herein is SEQ ID NO: 22, 23, 24, or 25.

In one embodiment, the N-glycosylated interleukin-2 domain in the fusion protein provided herein comprises two amino acid substitutions: (i) F42N and (ii) F44T or F44S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 26, 27, 28, or 29. In yet another embodiment, the amino acid sequence of the N-glycosylated interleukin-2 domain in the fusion protein provided herein is SEQ ID NO: 26, 27, 28, or 29.

In one embodiment, the N-glycosylated interleukin-2 domain in the fusion protein provided herein comprises two amino acid substitutions: (i) K43N and (ii) Y45T or Y45S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 30, 31, 32, or 33. In yet another embodiment, the amino acid sequence of the N-glycosylated interleukin-2 domain in the fusion protein provided herein is SEQ ID NO: 30, 31, 32, or 33.

In one embodiment, the N-glycosylated interleukin-2 domain in the fusion protein provided herein comprises two amino acid substitutions: (i) F44N and (ii) M46T or M46S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 34, 35, 36, or 37. In yet another embodiment, the amino acid sequence of the N-glycosylated interleukin-2 domain in the fusion protein provided herein is SEQ ID NO: 34, 35, 36, or 37.

In one embodiment, the N-glycosylated interleukin-2 domain in the fusion protein provided herein comprises two amino acid substitutions: (i) Y45N and (ii) P47T or P47S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 38, 39, 40, or 41. In yet another embodiment, the amino acid sequence of the N-glycosylated interleukin-2 domain in the fusion protein provided herein is SEQ ID NO: 38, 39, 40, or 41.

In one embodiment, the N-glycosylated interleukin-2 domain in the fusion protein provided herein comprises two amino acid substitutions: (i) E61N and (ii) L63T or L63S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 42, 43, 44, or 45. In yet another embodiment, the amino acid sequence of the N-glycosylated interleukin-2 domain in the fusion protein provided herein is SEQ ID NO: 42, 43, 44, or 45.

In one embodiment, the N-glycosylated interleukin-2 domain in the fusion protein provided herein comprises two amino acid substitutions: (i) E62N and (ii) K64T or K64S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 46, 47, 48, or 49. In yet another embodiment, the amino acid sequence of the N-glycosylated interleukin-2 domain in the fusion protein provided herein is SEQ ID NO: 46, 47, 48, or 49.

In one embodiment, the N-glycosylated interleukin-2 domain in the fusion protein provided herein comprises two amino acid substitutions: (i) P65N and (ii) E67T or E67S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 54, 55, 56, or 57. In yet another embodiment, the amino acid sequence of the N-glycosylated interleukin-2 domain in the fusion protein provided herein is SEQ ID NO: 54, 55, 56, or 57.

In one embodiment, the N-glycosylated interleukin-2 domain in the fusion protein provided herein comprises two amino acid substitutions: (i) L66N and (ii) E68T or E68S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 58, 59, 60, or 61. In yet another embodiment, the amino acid sequence of the N-glycosylated interleukin-2 domain in the fusion protein provided herein is SEQ ID NO: 58, 59, 60, or 61.

In one embodiment, the N-glycosylated interleukin-2 domain in the fusion protein provided herein comprises two amino acid substitutions: (i) E68N and (ii) L70T or L70S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 62, 63, 64, or 65. In yet another embodiment, the amino acid sequence of the N-glycosylated interleukin-2 domain in the fusion protein provided herein is SEQ ID NO: 62, 63, 64, or 65.

In one embodiment, the N-glycosylated interleukin-2 domain in the fusion protein provided herein comprises two amino acid substitutions: (i) V69N and (ii) N71T or N71S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 66, 67, 68, or 69. In yet another embodiment, the amino acid sequence of the N-glycosylated interleukin-2 domain in the fusion protein provided herein is SEQ ID NO: 66, 67, 68, or 69.

In one embodiment, the N-glycosylated interleukin-2 domain in the fusion protein provided herein comprises two amino acid substitutions: (i) L72N and (ii) Q74T or Q74S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 74, 75, 76, or 77. In yet another embodiment, the amino acid sequence of the N-glycosylated interleukin-2 domain in the fusion protein provided herein is SEQ ID NO: 74, 75, 76, or 77.

In one embodiment, the N-glycosylated interleukin-2 domain in the fusion protein provided herein comprises two amino acid substitutions: (i) Y107N and (ii) D109T or D109S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 78, 79, 80, or 81. In yet another embodiment, the amino acid sequence of the N-glycosylated interleukin-2 domain in the fusion protein provided herein is SEQ ID NO: 78, 79, 80, or 81.

In one embodiment, the N-glycosylated interleukin-2 domain in the fusion protein provided herein comprises two amino acid substitutions: (i) D109N and (ii) T111S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 83 or 85. In yet another embodiment, the amino acid sequence of the N-glycosylated interleukin-2 domain in the fusion protein provided herein is SEQ ID NO: 83 or 85.

In one embodiment, the N-glycosylated interleukin-2 domain in the fusion protein provided herein comprises three amino acid substitutions: (i) R38N, (ii) L40T or L40S, and (iii) F42A, Y45A, E61A, or E62A, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 90, 91, 92, 93, 94, 95, 96, or 97. In yet another embodiment, the amino acid sequence of the N-glycosylated interleukin-2 domain in the fusion protein provided herein is SEQ ID NO: 90, 91, 92, 93, 94, 95, 96, or 97.

In one embodiment, the N-glycosylated interleukin-2 domain in the fusion protein provided herein comprises three amino acid substitutions: (i) K64N, (ii) P65A, and (iii) L66T or L66S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 50, 51, 52, or 52. In yet another embodiment, the amino acid sequence of the N-glycosylated interleukin-2 domain in the fusion protein provided herein is SEQ ID NO: 50, 51, 52, or 52.

In one embodiment, the N-glycosylated interleukin-2 domain in the fusion protein provided herein comprises four amino acid substitutions: (i) R38N, (ii) L40T or L40S, (iii) K43N, and (iv) Y45T or Y45S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 88 or 89. In yet another embodiment, the amino acid sequence of the N-glycosylated interleukin-2 domain in the fusion protein provided herein is SEQ ID NO: 88 or 89.

In yet another embodiment, the N-glycosylated interleukin-2 domain in the fusion protein provided herein comprises an amino acid sequence selected from SEQ ID NO: 6 to 97.

In still another embodiment, the N-glycosylated interleukin-2 domain in the fusion protein provided herein comprises an amino acid sequence selected from SEQ ID NO: 18 to 21, 30 to 33, and 88 to 97.

In one embodiment, the N-glycosylated interleukin-2 domain in the fusion protein provided herein has one glycan. In another embodiment, the N-glycosylated interleukin-2 domain in the fusion protein provided herein has one glycan attached to the nitrogen in the side chain of an asparagine residue.

In one embodiment, the N-glycosylated interleukin-2 domain in the fusion protein provided herein has two glycans. In another embodiment, the N-glycosylated interleukin-2 domain in the fusion protein provided herein has two glycans, of which at least one glycan is attached to the nitrogen in the side chain of an asparagine residue. In yet another embodiment, the N-glycosylated interleukin-2 domain in the fusion protein provided herein has two glycans, each of which is attached to the nitrogen in the side chain of an asparagine residue.

In one embodiment, the N-glycosylated interleukin-2 domain in the fusion protein provided herein has three glycans.

In one embodiment, the glycan is an N-glycan.

In one embodiment, the N-glycan on the N-glycosylated interleukin-2 domain in the fusion protein provided herein is oligomannose-type. In another embodiment, the N-glycan on the N-glycosylated interleukin-2 domain in the fusion protein provided herein is complex-type. In another embodiment, the N-glycan on the N-glycosylated interleukin-2 domain in the fusion protein provided herein is hydride-type.

In one embodiment, the N-glycan on the N-glycosylated interleukin-2 domain in the fusion protein provided herein is biantennary complex-type. In another embodiment, the N-glycan on the N-glycosylated interleukin-2 domain in the fusion protein provided herein is triantennary complex-type. In yet another embodiment, the N-glycan on the N-glycosylated interleukin-2 domain in the fusion protein provided herein is tetraantennary complex-type.

In one embodiment, the N-glycan on the N-glycosylated interleukin-2 domain in the fusion protein provided herein is one of the glycans described in FIG. 7. Szabo et al., *J.* Proteome. Res. 2018, 17, 1559-74, the disclosure of which is incorporated herein by reference in its entirety.

In certain embodiments, the N-glycosylated interleukin-2 domain in the fusion protein provided herein further includes one or more additional substitutions, deletions, and/or insertions; and/or one or more additional post-translational modifications.

In one embodiment, the interleukin-2 domain in the fusion protein provided herein is an interleukin-2 mutein. In one embodiment, the interleukin-2 mutein comprising one, two, three, four, or more substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5.

In one embodiment, the interleukin-2 mutein comprises an amino acid substitution at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the interleukin-2 mutein comprises an amino acid substitution at position K35, M39, A73, or D109 as set forth in an amino acid sequence of SEQ ID NO: 1, 2, 3, 4, or 5.

In another embodiment, the interleukin-2 mutein comprises two substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the interleukin-2 mutein comprises two substitutions at position P34, K35, L36, T37, R38, L40, T41, F42, K43, F44, Y45, M46, P47, E61, E62, L63, P65, L66, E67, E68, V69, L70, N71, L72, Q74, Y107, D109, and/or T111 as set forth in an amino acid sequence of SEQ ID NO: 1, 2, 3, 4, or 5.

In yet another embodiment, the interleukin-2 mutein comprises three substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the interleukin-2 mutein comprises three substitutions at position R38, L40, F42, Y45, E61, E62, K64, P65, and/or L66 as set forth in an amino acid sequence of SEQ ID NO: 1, 2, 3, 4, or 5.

In still another embodiment, the interleukin-2 mutein comprises four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the interleukin-2 mutein comprises four substitutions at position R38, L40, F42, and Y45 as set forth in an amino acid sequence of SEQ ID NO: 1, 2, 3, 4, or 5.

In yet another embodiment, the interleukin-2 mutein comprises one, two, three, or four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In one embodiment, the interleukin-2 mutein comprises one substitution selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In another embodiment, the interleukin-2 mutein comprises two substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In yet another embodiment, the interleukin-2 mutein comprises the substitutions of R38N and Y45N as set forth in an amino acid sequence of SEQ ID NO: 1, 2, 3, 4, or 5. In yet another embodiment, the interleukin-2 mutein comprises three substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In still another embodiment, the interleukin-2 mutein comprises four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5.

In yet another embodiment, the interleukin-2 mutein comprises one, two, three, or more N-glycosylation sites, each independently having an amino acid sequence of NXT or NXS, wherein each X is independently A, C, D, E, F, G, H, I, K, L, M, N, Q, R, S, T, V, W, or Y.

In one embodiment, the interleukin-2 mutein comprises an N-glycosylation site having an amino acid sequence of NXT or NXS, wherein each X is independently A, C, D, E, F, G, H, I, K, L, M, N, Q, R, S, T, V, W, or Y. In another embodiment, the interleukin-2 mutein comprises two N-glycosylation sites, each independently having an amino acid sequence of NXT or NXS, wherein each X is independently A, C, D, E, F, G, H, I, K, L, M, N, Q, R, S, T, V, W, or Y. In yet another embodiment, the interleukin-2 mutein comprises an N-glycosylation site of NFT and an N-glycosylation site of NMT. In still another embodiment, the interleukin-2 mutein comprises four N-glycosylation sites, each independently having an amino acid sequence of NXT or NXS, wherein each X is independently A, C, D, E, F, G, H, I, K, L, M, N, Q, R, S, T, V, W, or Y.

In one embodiment, each X is independently A, C, D, E, F, G, H, I, K, M, N, Q, R, S, T, V, or Y. In another embodiment, each X is independently A, C, D, G, H, K, M, N, Q, R, S, T, V, W, or Y. In yet another embodiment, each X is independently A, E, F, K, L, M, R, V, W, or Y. In still another embodiment, each X is independently F or M.

In yet another embodiment, the interleukin-2 mutein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS.

In one embodiment, the interleukin-2 mutein comprises an N-glycosylation site having an amino acid sequence of NAT or NAS. In another embodiment, the interleukin-2 mutein comprises an N-glycosylation site having an amino acid sequence of NET or NES. In yet another embodiment, the interleukin-2 mutein comprises an N-glycosylation site having an amino acid sequence of NFT or NFS. In yet another embodiment, the interleukin-2 mutein comprises an N-glycosylation site having an amino acid sequence of NKT or NKS. In yet another embodiment, the interleukin-2 mutein comprises an N-glycosylation site having an amino acid sequence of NLT or NLS. In yet another embodiment, the interleukin-2 mutein comprises an N-glycosylation site having an amino acid sequence of NMT or NMS. In yet another embodiment, the interleukin-2 mutein comprises an N-glycosylation site having an amino acid sequence of NRT or NRS. In yet another embodiment, the interleukin-2 mutein comprises an N-glycosylation site having an amino acid sequence of NVT or NVS. In yet another embodiment, the interleukin-2 mutein comprises an N-glycosylation site having an amino acid sequence of NWT or NWS. In still another embodiment, the interleukin-2 mutein comprises an N-glycosylation site having an amino acid sequence of NYT or NYS.

In yet another embodiment, the interleukin-2 mutein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS, each independently starting at position 34, 35, 37, 38, 39, 41, 42, 43, 44, 45, 61, 62, 64, 65, 66, 68, 69, 71, 72, 107, or 109 as set forth in an amino acid sequence of SEQ ID NO: 1, 2, 3, 4, or 5.

In one embodiment, the interleukin-2 mutein comprises an N-glycosylation site having an amino acid sequence of NKT or NKS, each independently starting at position 34 or 42 as set forth in an amino acid sequence of SEQ ID NO: 1, 2, 3, 4, or 5.

In another embodiment, the interleukin-2 mutein comprises an N-glycosylation site having an amino acid sequence of NLT or NLS, each independently starting at position 35, 39, 62, 65, 69, or 71 as set forth in an amino acid sequence of SEQ ID NO: 1, 2, 3, 4, or 5.

In yet another embodiment, the interleukin-2 mutein comprises an N-glycosylation site having an amino acid sequence of NRT or NRS, each independently starting at position 37 as set forth in an amino acid sequence of SEQ ID NO: 1, 2, 3, 4, or 5.

In yet another embodiment, the interleukin-2 mutein comprises an N-glycosylation site having an amino acid sequence of NMT or NMS, each independently starting at position 38 or 45 as set forth in an amino acid sequence of SEQ ID NO: 1, 2, 3, 4, or 5.

In yet another embodiment, the interleukin-2 mutein comprises an N-glycosylation site having an amino acid sequence of NFT or NFS, each independently starting at position 41 or 43 as set forth in an amino acid sequence of SEQ ID NO: 1, 2, 3, 4, or 5.

In yet another embodiment, the interleukin-2 mutein comprises an N-glycosylation site having an amino acid sequence of NYT or NYS, each independently starting at position 44 as set forth in an amino acid sequence of SEQ ID NO: 1, 2, 3, 4, or 5.

In yet another embodiment, the interleukin-2 mutein comprises an N-glycosylation site having an amino acid sequence of NET or NES, each independently starting at position 61, 66, or 109 as set forth in an amino acid sequence of SEQ ID NO: 1, 2, 3, 4, or 5.

In yet another embodiment, the interleukin-2 mutein comprises an N-glycosylation site having an amino acid sequence of NAT or NAS, each independently starting at position 64, 72, or 107 as set forth in an amino acid sequence of SEQ ID NO: 1, 2, 3, 4, or 5.

In still another embodiment, the interleukin-2 mutein comprises an N-glycosylation site having an amino acid sequence of NVT or NVS, each independently starting at position 68 as set forth in an amino acid sequence of SEQ ID NO: 1, 2, 3, 4, or 5.

In yet another embodiment, the interleukin-2 mutein comprises an amino acid sequence of NA, NE, NK, NM, or NW.

In one embodiment, the interleukin-2 mutein comprises an amino acid sequence of NA. In another embodiment, the interleukin-2 mutein comprises an amino acid sequence of NE. In yet another embodiment, the interleukin-2 mutein comprises an amino acid sequence of NK. In yet another embodiment, the interleukin-2 mutein comprises an amino acid sequence of NM. In still another embodiment, the interleukin-2 mutein comprises an amino acid sequence of NW.

In yet another embodiment, the interleukin-2 mutein comprises an amino acid sequence of NA, NE, NK, NM, or NW, each independently starting at position 34, 38, 42, 45, 61, 64, 66, 72, 107, or 109 as set forth in an amino acid sequence of SEQ ID NO: 1, 2, 3, 4, or 5.

In one embodiment, the interleukin-2 mutein comprises an amino acid sequence of NK starting at position 34 or 42 as set forth in an amino acid sequence of SEQ ID NO: 1, 2, 3, 4, or 5. In another embodiment, the interleukin-2 mutein comprises an amino acid sequence of NM starting at position 38 or 45 as set forth in an amino acid sequence of SEQ ID NO: 1, 2, 3, 4, or 5. In yet another embodiment, the interleukin-2 mutein comprises an amino acid sequence of NE starting at position 61, 66, or 109 as set forth in an amino acid sequence of SEQ ID NO: 1, 2, 3, 4, or 5. In still another embodiment, the interleukin-2 mutein comprises an amino acid sequence of NA starting at position 64, 72, or 107 as set forth in an amino acid sequence of SEQ ID NO: 1, 2, 3, 4, or 5.

In yet another embodiment, the interleukin-2 mutein comprises an N-glycosylation site that comprises an amino acid sequence of NK, NM, NE, NW, or NA.

In one embodiment, the interleukin-2 mutein comprises an N-glycosylation site that comprises an amino acid sequence of NK. In another embodiment, the interleukin-2 mutein comprises an N-glycosylation site that comprises an amino acid sequence of NM. In yet another embodiment, the interleukin-2 mutein comprises an N-glycosylation site that comprises an amino acid sequence of NE. In yet another embodiment, the interleukin-2 mutein comprises an N-glycosylation site that comprises an amino acid sequence of NW. In still another embodiment, the interleukin-2 mutein comprises an N-glycosylation site that comprises an amino acid sequence of NA.

In yet another embodiment, the interleukin-2 mutein comprises a N-glycosylation site that comprises an amino acid sequence of NK, NM, NE, NW, or NA, each independently starting at position 34, 38, 42, 45, 61, 64, 66, 72, 107, or 109 as set forth in an amino acid sequence of SEQ ID NO: 1, 2, 3, 4, or 5.

In one embodiment, the interleukin-2 mutein comprises an N-glycosylation site that comprises an amino acid sequence of NK starting at position 34 or 42 as set forth in an amino acid sequence of SEQ ID NO: 1, 2, 3, 4, or 5. In another embodiment, the interleukin-2 mutein comprises an N-glycosylation site that comprises an amino acid sequence of NM starting at position 38 or 45 as set forth in an amino acid sequence of SEQ ID NO: 1, 2, 3, 4, or 5. In yet another embodiment, the interleukin-2 mutein comprises an N-glycosylation site that comprises an amino acid sequence of NE starting at position 61, 66, or 109 as set forth in an amino acid sequence of SEQ ID NO: 1, 2, 3, 4, or 5. In still another embodiment, the interleukin-2 mutein comprises an N-glycosylation site that comprises an amino acid sequence of NA starting at position 64, 72, or 107 as set forth in an amino acid sequence of SEQ ID NO: 1, 2, 3, 4, or 5.

In yet another embodiment, the interleukin-2 mutein comprises an N-glycosylation site at an interface residue between an interleukin-2 and an interleukin-2 receptor-α (IL-2Rα) chain.

In one embodiment, the interface residue is K35, T37, R38, T41, F42, K43, F44, Y45, E61, E62, K64, P65, E68, L72, or Y107 as set forth in SEQ ID NO: 1, 2, 3, 4, or 5. In another embodiment, the interface residue is K35 as set forth in SEQ ID NO: 1, 2, 3, 4, or 5. In yet another embodiment, the interface residue is T37 as set forth in SEQ ID NO: 1, 2, 3, 4, or 5. In yet another embodiment, the interface residue is R38 as set forth in SEQ ID NO: 1, 2, 3, 4, or 5. In yet another embodiment, the interface residue is T41 as set forth in SEQ ID NO: 1, 2, 3, 4, or 5. In yet another embodiment, the interface residue is F42 as set forth in SEQ ID NO: 1, 2, 3, 4, or 5. In yet another embodiment, the interface residue is K43 as set forth in SEQ ID NO: 1, 2, 3, 4, or 5. In yet another embodiment, the interface residue is F44 as set forth in SEQ ID NO: 1, 2, 3, 4, or 5. In yet another embodiment, the interface residue is Y45 as set forth in SEQ ID NO: 1, 2, 3, 4, or 5. In yet another embodiment, the interface residue is E61 as set forth in SEQ ID NO: 1, 2, 3, 4, or 5. In yet another embodiment, the interface residue is E62 as set forth in SEQ ID NO: 1, 2, 3, 4, or 5. In yet another embodiment, the interface residue is K64 as set forth in SEQ ID NO: 1, 2, 3, 4, or 5. In yet another embodiment, the interface residue is P65 as set forth in SEQ ID NO: 1, 2, 3, 4, or 5. In yet another embodiment, the interface residue is E68 as set forth in SEQ ID NO: 1, 2, 3, 4, or 5. In still another embodiment, the interface residue is L72 as set forth in SEQ ID NO: 1, 2, 3, 4, or 5. In yet another embodiment, the interface residue is Y107 as set forth in SEQ ID NO: 1, 2, 3, 4, or 5.

In still another embodiment, the interleukin-2 mutein comprises an N-glycosylation site at position K35, T37, R38, T41, F42, K43, F44, Y45, E61, E62, K64, P65, E68, L72, or Y107 as set forth in an amino acid sequence of SEQ ID NO: 1, 2, 3, 4, or 5.

In one embodiment, the interleukin-2 mutein comprises an N-glycosylation site at position K35 as set forth in an amino acid sequence of SEQ ID NO: 1, 2, 3, 4, or 5. In another embodiment, the interleukin-2 mutein comprises an N-glycosylation site at position T37 as set forth in an amino acid sequence of SEQ ID NO: 1, 2, 3, 4, or 5. In yet another embodiment, the interleukin-2 mutein comprises an N-glycosylation site at position R38 as set forth in an amino acid sequence of SEQ ID NO: 1, 2, 3, 4, or 5. In yet another embodiment, the interleukin-2 mutein comprises an N-glycosylation site at position T41 as set forth in an amino acid sequence of SEQ ID NO: 1, 2, 3, 4, or 5. In yet another embodiment, the interleukin-2 mutein comprises an N-glycosylation site at position F42 as set forth in an amino acid sequence of SEQ ID NO: 1, 2, 3, 4, or 5. In yet another embodiment, the interleukin-2 mutein comprises an N-glycosylation site at position K43 as set forth in an amino acid sequence of SEQ ID NO: 1, 2, 3, 4, or 5. In yet another embodiment, the interleukin-2 mutein comprises an N-glycosylation site at position F44 as set forth in an amino acid sequence of SEQ ID NO: 1, 2, 3, 4, or 5. In yet another embodiment, the interleukin-2 mutein comprises an N-glycosylation site at position Y45 as set forth in an amino acid sequence of SEQ ID NO: 1, 2, 3, 4, or 5. In yet another embodiment, the interleukin-2 mutein comprises an N-glycosylation site at position E61 as set forth in an amino acid sequence of SEQ ID NO: 1, 2, 3, 4, or 5. In yet another embodiment, the interleukin-2 mutein comprises an N-glycosylation site at position E62 as set forth in an amino acid sequence of SEQ ID NO: 1, 2, 3, 4, or 5. In yet another embodiment, the interleukin-2 mutein comprises an N-glycosylation site at position K64 as set forth in an amino acid sequence of SEQ ID NO: 1, 2, 3, 4, or 5. In yet another embodiment, the interleukin-2 mutein comprises an N-glycosylation site at position P65 in an amino acid sequence of SEQ ID NO: 1, 2, 3, 4, or 5. In yet another embodiment, the interleukin-2 mutein comprises an N-glycosylation site at position E68 as set forth in an amino acid sequence of SEQ ID NO: 1, 2, 3, 4, or 5. In yet another embodiment, the interleukin-2 mutein comprises an N-glycosylation site at position L72 as set forth in an amino acid sequence of SEQ ID NO: 1, 2, 3, 4, or 5. In still another embodiment, the interleukin-2 mutein comprises an N-glycosylation site at position Y107 as set forth in an amino acid sequence of SEQ ID NO: 1, 2, 3, 4, or 5.

In certain embodiments, the interleukin-2 mutein comprises an amino acid sequence that is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the interleukin-2 mutein is no less than about 80% identical to an amino acid sequence of SEQ ID NO: 1, 2, 3, 4, or 5. In certain embodiments, the interleukin-2 mutein comprises an amino acid sequence that is no less than about 85% identical to an amino acid sequence of SEQ ID NO: 1, 2, 3, 4, or 5. In certain embodiments, the interleukin-2 mutein comprises an amino acid sequence that is no less than about 90% identical to an amino acid sequence of SEQ ID NO: 1, 2, 3, 4, or 5. In certain embodiments, the interleukin-2 mutein comprises an amino acid sequence that is no less than about 91% identical to an amino acid sequence of SEQ ID NO: 1, 2, 3, 4, or 5. In certain embodiments, the interleukin-2 mutein comprises an amino acid sequence that is no less than about 92% identical to an amino acid sequence of SEQ ID NO: 1, 2, 3, 4, or 5. In certain embodiments, the interleukin-2 mutein comprises an amino acid sequence that is no less than about 93% identical to an amino acid sequence of SEQ ID NO: 1, 2, 3, 4, or 5. In certain embodiments, the interleukin-2 mutein comprises an amino acid sequence that is no less than about 94% identical to an amino acid sequence of SEQ ID NO: 1, 2, 3, 4, or 5. In certain embodiments, the interleukin-2 mutein comprises an amino acid sequence that is no less than about 95% identical to an amino acid sequence of SEQ ID NO: 1, 2, 3, 4, or 5. In certain embodiments, the interleukin-2 mutein comprises an amino acid sequence that is no less than about 96% identical to an amino acid sequence of SEQ ID NO: 1, 2, 3, 4, or 5. In certain embodiments, the interleukin-2 mutein comprises an amino acid sequence that is no less than about 97% identical to an amino acid sequence of SEQ ID NO: 1, 2, 3, 4, or 5. In certain embodiments, the interleukin-2 mutein comprises an amino acid sequence that is no less than about 98% identical to an amino acid sequence of SEQ ID NO: 1, 2, 3, 4, or 5. In certain embodiments, the interleukin-2 mutein comprises an amino acid sequence that is no less than about 99% identical to an amino acid sequence of SEQ ID NO: 1, 2, 3, 4, or 5.

In certain embodiments, the interleukin-2 mutein is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the interleukin-2 mutein is no less than about 80% identical to an amino acid sequence of SEQ ID NO: 1, 2, 3, 4, or 5. In certain embodiments, the interleukin-2 mutein is no less than about 85% identical to an amino acid sequence of SEQ ID NO: 1, 2, 3, 4, or 5. In certain embodiments, the interleukin-2 mutein is no less than about 90% identical to an amino acid sequence of SEQ ID NO: 1, 2, 3, 4, or 5. In certain embodiments, the interleukin-2 mutein is no less than about 91% identical to an amino acid sequence of SEQ ID NO: 1, 2, 3, 4, or 5. In certain embodiments, the interleukin-2 mutein is no less than about 92% identical to an amino acid sequence of SEQ ID NO: 1, 2, 3, 4, or 5. In certain embodiments, the interleukin-2 mutein is no less than about 93% identical to an amino acid sequence of SEQ ID NO: 1, 2, 3, 4, or 5. In certain embodiments, the interleukin-2 mutein is no less than about 94% identical to an amino acid sequence of SEQ ID NO: 1, 2, 3, 4, or 5. In certain embodiments, the interleukin-2 mutein is no less than about 95% identical to an amino acid sequence of SEQ ID NO: 1, 2, 3, 4, or 5. In certain embodiments, the interleukin-2 mutein is no less than about 96% identical to an amino acid sequence of SEQ ID NO: 1, 2, 3, 4, or 5. In certain embodiments, the interleukin-2 mutein is no less than about 97% identical to an amino acid sequence of SEQ ID NO: 1, 2, 3, 4, or 5. In certain embodiments, the interleukin-2 mutein is no less than about 98% identical to an amino acid sequence of SEQ ID NO: 1, 2, 3, 4, or 5. In certain embodiments, the interleukin-2 mutein is no less than about 99% identical to an amino acid sequence of SEQ ID NO: 1, 2, 3, 4, or 5.

In certain embodiments, the interleukin-2 mutein comprises an amino acid substitution: K35N, M39N, A73T, A73S, or D109N, as set forth in an amino acid sequence of SEQ ID NO: 1, 2, 3, 4, or 5.

In one embodiment, the interleukin-2 mutein comprises an amino acid substitution: K35N, as set forth in an amino acid sequence of SEQ ID NO: 1, 2, 3, 4, or 5. In another embodiment, the interleukin-2 mutein comprises an amino acid sequence of SEQ ID NO: 10, 11, 12, or 13. In yet another embodiment, the amino acid sequence of the interleukin-2 mutein is SEQ ID NO: 10, 11, 12, or 13.

In one embodiment, the interleukin-2 mutein comprises an amino acid substitution: M39N, as set forth in an amino acid sequence of SEQ ID NO: 1, 2, 3, 4, or 5. In another embodiment, the interleukin-2 mutein comprises the amino acid sequence of SEQ ID NO: 86 or 87. In yet another embodiment, the amino acid sequence of the interleukin-2 mutein is SEQ ID NO: 86 or 87.

In one embodiment, the interleukin-2 mutein comprises an amino acid substitution: A73T or A73S, as set forth in an amino acid sequence of SEQ ID NO: 1, 2, 3, 4, or 5. In another embodiment, the interleukin-2 mutein comprises the amino acid sequence of SEQ ID NO: 70, 71, 72, or 73. In yet another embodiment, the amino acid sequence of the interleukin-2 mutein is SEQ ID NO: 70, 71, 72, or 73.

In one embodiment, the interleukin-2 mutein comprises an amino acid substitution: D109N, as set forth in an amino acid sequence of SEQ ID NO: 1, 2, 3, 4, or 5. In another embodiment, the interleukin-2 mutein comprises the amino acid sequence of SEQ ID NO: 82, 83, 84, or 85. In yet another embodiment, the amino acid sequence of the interleukin-2 mutein is SEQ ID NO: 82, 83, 84, or 85.

In certain embodiments, the interleukin-2 mutein comprises a two-amino acid substitution combination selected from (i) P34N and L36T or L36S; (ii) K35N and T37S; (iii) T37N and M39T or M39S; (iv) R38N and L40T or L40S; (v) T41N and K43T or K43S; (vi) F42N and F44T or F44S; (vii) K43N and Y45T or Y45S; (viii) F44N and M46T or M46S; (ix) Y45N and P47T or P47S; (x) E61N and L63T or L63S; (xi) E62N and K64T or K64S; (xii) P65N and E67T or E67S; (xiii) L66N and E68T or E68S; (xiv) E68N and L70T or L70S; (xv) V69N and N71T or N71S; (xvi) L72N and Q74T or Q74S; (xvii) Y107N and D109T or D109S; or (xviii) D109N and T111S; as set forth in an amino acid sequence of SEQ ID NO: 1, 2, 3, 4, or 5.

In one embodiment, the interleukin-2 mutein comprises two amino acid substitutions: (i) P34N and (ii) L36T or L36S, as set forth in an amino acid sequence of SEQ ID NO: 1, 2, 3, 4, or 5. In another embodiment, the interleukin-2 mutein comprises the amino acid sequence of SEQ ID NO: 6, 7, 8, or 9. In yet another embodiment, the amino acid sequence of the interleukin-2 mutein is SEQ ID NO: 6, 7, 8, or 9.

In one embodiment, the interleukin-2 mutein comprises two amino acid substitutions: K35N and T37S, as set forth in an amino acid sequence of SEQ ID NO: 1, 2, 3, 4, or 5. In another embodiment, the interleukin-2 mutein comprises the amino acid sequence of SEQ ID NO: 11 or 13. In yet another embodiment, the amino acid sequence of the interleukin-2 mutein is SEQ ID NO: 11 or 13.

In one embodiment, the interleukin-2 mutein comprises two amino acid substitutions: (i) T37N and (ii) M39T or M39S, as set forth in an amino acid sequence of SEQ ID NO: 1, 2, 3, 4, or 5. In another embodiment, the interleukin-2 mutein comprises the amino acid sequence of SEQ ID NO: 14, 15, 16, or 17. In yet another embodiment, the amino acid sequence of the interleukin-2 mutein is SEQ ID NO: 14, 15, 16, or 17.

In one embodiment, the interleukin-2 mutein comprises two amino acid substitutions: (i) R38N and (ii) L40T or L40S, as set forth in an amino acid sequence of SEQ ID NO: 1, 2, 3, 4, or 5. In another embodiment, the interleukin-2 mutein comprises the amino acid sequence of SEQ ID NO: 18, 19, 20, or 21. In yet another embodiment, the amino acid sequence of the interleukin-2 mutein is SEQ ID NO: 18, 19, 20, or 21.

In one embodiment, the interleukin-2 mutein comprises two amino acid substitutions: (i) T41N and (ii) K43T or K43S, as set forth in an amino acid sequence of SEQ ID NO: 1, 2, 3, 4, or 5. In another embodiment, the interleukin-2 mutein comprises the amino acid sequence of SEQ ID NO: 22, 23, 24, or 25. In yet another embodiment, the amino acid sequence of the interleukin-2 mutein is SEQ ID NO: 22, 23, 24, or 25.

In one embodiment, the interleukin-2 mutein comprises two amino acid substitutions: (i) F42N and (ii) F44T or F44S, as set forth in an amino acid sequence of SEQ ID NO: 1, 2, 3, 4, or 5. In another embodiment, the interleukin-2 mutein comprises the amino acid sequence of SEQ ID NO: 26, 27, 28, or 29. In yet another embodiment, the amino acid sequence of the interleukin-2 mutein is SEQ ID NO: 26, 27, 28, or 29.

In one embodiment, the interleukin-2 mutein comprises two amino acid substitutions: (i) K43N and (ii) Y45T or Y45S, as set forth in an amino acid sequence of SEQ ID NO: 1, 2, 3, 4, or 5. In another embodiment, the interleukin-2 mutein comprises the amino acid sequence of SEQ ID NO: 30, 31, 32, or 33. In yet another embodiment, the amino acid sequence of the interleukin-2 mutein is SEQ ID NO: 30, 31, 32, or 33.

In one embodiment, the interleukin-2 mutein comprises two amino acid substitutions: (i) F44N and (ii) M46T or M46S, as set forth in an amino acid sequence of SEQ ID NO: 1, 2, 3, 4, or 5. In another embodiment, the interleukin-2 mutein comprises the amino acid sequence of SEQ ID NO: 34, 35, 36, or 37. In yet another embodiment, the amino acid sequence of the interleukin-2 mutein is SEQ ID NO: 34, 35, 36, or 37.

In one embodiment, the interleukin-2 mutein comprises two amino acid substitutions: (i) Y45N and (ii) P47T or P47S, as set forth in an amino acid sequence of SEQ ID NO: 1, 2, 3, 4, or 5. In another embodiment, the interleukin-2 mutein comprises the amino acid sequence of SEQ ID NO: 38, 39, 40, or 41. In yet another embodiment, the amino acid sequence of the interleukin-2 mutein is SEQ ID NO: 38, 39, 40, or 41.

In one embodiment, the interleukin-2 mutein comprises two amino acid substitutions: (i) E61N and (ii) L63T or L63S, as set forth in an amino acid sequence of SEQ ID NO: 1, 2, 3, 4, or 5. In another embodiment, the interleukin-2 mutein comprises the amino acid sequence of SEQ ID NO: 42, 43, 44, or 45. In yet another embodiment, the amino acid sequence of the interleukin-2 mutein is SEQ ID NO: 42, 43, 44, or 45.

In one embodiment, the interleukin-2 mutein comprises two amino acid substitutions: (i) E62N and (ii) K64T or K64S, as set forth in an amino acid sequence of SEQ ID NO: 1, 2, 3, 4, or 5. In another embodiment, the interleukin-2 mutein comprises the amino acid sequence of SEQ ID NO: 46, 47, 48, or 49. In yet another embodiment, the amino acid sequence of the interleukin-2 mutein is SEQ ID NO: 46, 47, 48, or 49.

In one embodiment, the interleukin-2 mutein comprises two amino acid substitutions: (i) P65N and (ii) E67T or E67S, as set forth in an amino acid sequence of SEQ ID NO: 1, 2, 3, 4, or 5. In another embodiment, the interleukin-2 mutein comprises the amino acid sequence of SEQ ID NO: 54, 55, 56, or 57. In yet another embodiment, the amino acid sequence of the interleukin-2 mutein is SEQ ID NO: 54, 55, 56, or 57.

In one embodiment, the interleukin-2 mutein comprises two amino acid substitutions: (i) L66N and (ii) E68T or E68S, as set forth in an amino acid sequence of SEQ ID NO: 1, 2, 3, 4, or 5. In another embodiment, the interleukin-2 mutein comprises the amino acid sequence of SEQ ID NO: 58, 59, 60, or 61. In yet another embodiment, the amino acid sequence of the interleukin-2 mutein is SEQ ID NO: 58, 59, 60, or 61.

In one embodiment, the interleukin-2 mutein comprises two amino acid substitutions: (i) E68N and (ii) L70T or L70S, as set forth in an amino acid sequence of SEQ ID NO: 1, 2, 3, 4, or 5. In another embodiment, the interleukin-2 mutein comprises the amino acid sequence of SEQ ID NO: 62, 63, 64, or 65. In yet another embodiment, the amino acid sequence of the interleukin-2 mutein is SEQ ID NO: 62, 63, 64, or 65.

In one embodiment, the interleukin-2 mutein comprises two amino acid substitutions: (i) V69N and (ii) N71T or N71S, as set forth in an amino acid sequence of SEQ ID NO: 1, 2, 3, 4, or 5. In another embodiment, the interleukin-2 mutein comprises the amino acid sequence of SEQ ID NO: 66, 67, 68, or 69. In yet another embodiment, the amino acid sequence of the interleukin-2 mutein is SEQ ID NO: 66, 67, 68, or 69.

In one embodiment, the interleukin-2 mutein comprises two amino acid substitutions: (i) L72N and (ii) Q74T or Q74S, as set forth in an amino acid sequence of SEQ ID NO: 1, 2, 3, 4, or 5. In another embodiment, the interleukin-2 mutein comprises the amino acid sequence of SEQ ID NO: 74, 75, 76, or 77. In yet another embodiment, the amino acid sequence of the interleukin-2 mutein is SEQ ID NO: 74, 75, 76, or 77.

In one embodiment, the interleukin-2 mutein comprises two amino acid substitutions: (i) Y107N and (ii) D109T or D109S, as set forth in an amino acid sequence of SEQ ID NO: 1, 2, 3, 4, or 5. In another embodiment, the interleukin-2 mutein comprises the amino acid sequence of SEQ ID NO: 78, 79, 80, or 81. In yet another embodiment, the amino acid sequence of the interleukin-2 mutein is SEQ ID NO: 78, 79, 80, or 81.

In one embodiment, the interleukin-2 mutein comprises two amino acid substitutions: (i) D109N and (ii) T111S, as set forth in an amino acid sequence of SEQ ID NO: 1, 2, 3, 4, or 5. In another embodiment, the interleukin-2 mutein comprises the amino acid sequence of SEQ ID NO: 83 or 85. In yet another embodiment, the amino acid sequence of the interleukin-2 mutein is SEQ ID NO: 83 or 85.

In one embodiment, the interleukin-2 mutein comprises three amino acid substitutions: (i) R38N, (ii) L40T or L40S, and (iii) F42A, Y45A, E61A, or E62A, as set forth in an amino acid sequence of SEQ ID NO: 1, 2, 3, 4, or 5. In another embodiment, the interleukin-2 mutein comprises the amino acid sequence of SEQ ID NO: 90, 91, 92, 93, 94, 95, 96, or 97. In yet another embodiment, the amino acid sequence of the interleukin-2 mutein is SEQ ID NO: 90, 91, 92, 93, 94, 95, 96, or 97.

In one embodiment, the interleukin-2 mutein comprises three amino acid substitutions: (i) K64N, (ii) P65A, and (iii) L66T or L66S, as set forth in an amino acid sequence of SEQ ID NO: 1, 2, 3, 4, or 5. In another embodiment, the interleukin-2 mutein comprises the amino acid sequence of SEQ ID NO: 50, 51, 52, or 52. In yet another embodiment, the amino acid sequence of the interleukin-2 mutein is SEQ ID NO: 50, 51, 52, or 52.

In one embodiment, the interleukin-2 mutein comprises four amino acid substitutions: (i) R38N, (ii) L40T, (iii) K43N, or (iv) Y45T or Y45S, as set forth in an amino acid sequence of SEQ ID NO: 1, 2, 3, 4, or 5. In another embodiment, the interleukin-2 mutein comprises the amino acid sequence of SEQ ID NO: 88 or 89. In yet another embodiment, the amino acid sequence of the interleukin-2 mutein is SEQ ID NO: 88 or 89.

In yet another embodiment, the interleukin-2 mutein comprises an amino acid sequence selected from SEQ ID NO: 6 to 97.

In still another embodiment, the interleukin-2 mutein comprises an amino acid sequence selected from SEQ ID NO: 18 to 21, 30 to 33, and 88 to 97.

In certain embodiments, the interleukin-2 mutein further includes one or more additional substitutions, deletions, and/or insertions; and/or one or more additional post-translational modifications.

In one embodiment, the interleukin-21 domain in the fusion protein provided herein is a wide-type interleukin-21 domain. In another embodiment, the interleukin-21 domain in the fusion protein provided herein is a wild-type human interleukin-21 domain. In yet another embodiment, the interleukin-21 domain in the fusion protein provided herein is an interleukin-21 variant. In still another embodiment, the interleukin-21 domain in the fusion protein provided herein is an interleukin-21 mutein.

In certain embodiments, the interleukin-21 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 156.

In certain embodiments, the interleukin-21 domain in the fusion protein provided herein comprises an amino acid sequence that is no less than about 70% identical to an amino acid sequence of SEQ ID NO: 156. In certain embodiments, the interleukin-21 domain in the fusion protein provided herein comprises an amino acid sequence that is no less than about 75% identical to an amino acid sequence of SEQ ID NO: 156. In certain embodiments, the interleukin-21 domain in the fusion protein provided herein comprises an amino acid sequence that is no less than about 80% identical to an amino acid sequence of SEQ ID NO: 156. In certain embodiments, the interleukin-21 domain in the fusion protein provided herein comprises an amino acid sequence that is no less than about 85% identical to an amino acid sequence of SEQ ID NO: 156. In certain embodiments, the interleukin-21 domain in the fusion protein provided herein comprises an amino acid sequence that is no less than about 90% identical to an amino acid sequence of SEQ ID NO: 156. In certain embodiments, the interleukin-21 domain in the fusion protein provided herein comprises an amino acid sequence that is no less than about 91% identical to an amino acid sequence of SEQ ID NO: 156. In certain embodiments, the interleukin-21 domain in the fusion protein provided herein comprises an amino acid sequence that is no less than about 92% identical to an amino acid sequence of SEQ ID NO: 156. In certain embodiments, the interleukin-21 domain in the fusion protein provided herein comprises an amino acid sequence that is no less than about 93% identical to an amino acid sequence of SEQ ID NO: 156. In certain embodiments, the interleukin-21 domain in the fusion protein provided herein comprises an amino acid sequence that is no less than about 94% identical to an amino acid sequence of SEQ ID NO: 156. In certain embodiments, the interleukin-21 domain in the fusion protein provided herein comprises an amino acid sequence that is no less than about 95% identical to an amino acid sequence of SEQ ID NO: 156. In certain embodiments, the interleukin-21 domain in the fusion protein provided herein comprises an amino acid sequence that is no less than about 96% identical to an amino acid sequence of SEQ ID NO: 156. In certain embodiments, the interleukin-21 domain in the fusion protein provided herein comprises an amino acid sequence that is no less than about 97% identical to an amino acid sequence of SEQ ID NO: 156. In certain embodiments, the interleukin-21 domain in the fusion protein provided herein comprises an amino acid sequence that is no less than about 98% identical to an amino acid sequence of SEQ ID NO: 156. In certain embodiments, the interleukin-21 domain in the fusion protein provided herein comprises an amino acid sequence that is no less than about 99% identical to an amino acid sequence of SEQ ID NO: 156.

In certain embodiments, the interleukin-21 domain in the fusion protein provided herein is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 156.

In certain embodiments, the interleukin-21 domain in the fusion protein provided herein is no less than about 70% identical to an amino acid sequence of SEQ ID NO: 156. In certain embodiments, the interleukin-21 domain in the fusion protein provided herein is no less than about 75% identical to an amino acid sequence of SEQ ID NO: 156. In certain embodiments, the interleukin-21 domain in the fusion protein provided herein is no less than about 80% identical to an amino acid sequence of SEQ ID NO: 156. In certain embodiments, the interleukin-21 domain in the fusion protein provided herein is no less than about 85% identical to an amino acid sequence of SEQ ID NO: 156. In certain embodiments, the interleukin-21 domain in the fusion protein provided herein is no less than about 90% identical to an amino acid sequence of SEQ ID NO: 156. In certain embodiments, the interleukin-21 domain in the fusion protein provided herein is no less than about 91% identical to an amino acid sequence of SEQ ID NO: 156. In certain embodiments, the interleukin-21 domain in the fusion protein provided herein is no less than about 92% identical to an amino acid sequence of SEQ ID NO: 156. In certain embodiments, the interleukin-21 domain in the fusion protein provided herein is no less than about 93% identical to an amino acid sequence of SEQ ID NO: 156. In certain embodiments, the interleukin-21 domain in the fusion protein provided herein is no less than about 94% identical to an amino acid sequence of SEQ ID NO: 156. In certain embodiments, the interleukin-21 domain in the fusion protein provided herein is no less than about 95% identical to an amino acid sequence of SEQ ID NO: 156. In certain embodiments, the interleukin-21 domain in the fusion protein provided herein is no less than about 96% identical to an amino acid sequence of SEQ ID NO: 156. In certain embodiments, the interleukin-21 domain in the fusion protein provided herein is no less than about 97% identical to an amino acid sequence of SEQ ID NO: 156. In certain embodiments, the interleukin-21 domain in the fusion protein provided herein is no less than about 98% identical to an amino acid sequence of SEQ ID NO: 156. In certain embodiments, the interleukin-21 domain in the fusion protein provided herein is no less than about 99% identical to an amino acid sequence of SEQ ID NO: 156.

In certain embodiments, the interleukin-21 variant lacks about 1 to about 10 amino acids between S124 and S133 as set forth in an amino acid sequence of SEQ ID NO: 156. In one embodiment, the interleukin-21 variant lacks one amino acid between S124 and S133 as set forth in an amino acid sequence of SEQ ID NO: 156. In another embodiment, the interleukin-21 variant lacks two amino acids between S124 and S133 as set forth in an amino acid sequence of SEQ ID NO: 156. In yet another embodiment, the interleukin-21 variant lacks three amino acids between S124 and S133 as set forth in an amino acid sequence of SEQ ID NO: 156. In yet another embodiment, the interleukin-21 variant lacks four amino acids between S124 and S133 as set forth in an amino acid sequence of SEQ ID NO: 156. In yet another embodiment, the interleukin-21 variant lacks five amino acids between S124 and S133 as set forth in an amino acid sequence of SEQ ID NO: 156. In yet another embodiment, the interleukin-21 variant lacks six amino acids between S124 and S133 as set forth in an amino acid sequence of SEQ ID NO: 156. In yet another embodiment, the interleukin-21 variant lacks seven amino acids between S124 and S133 as set forth in an amino acid sequence of SEQ ID NO: 156. In yet another embodiment, the interleukin-21 variant lacks eight amino acids between S124 and S133 as set forth in an amino acid sequence of SEQ ID NO: 156. In yet another embodiment, the interleukin-21 variant lacks nine amino acids between S124 and S133 as set forth in an amino acid sequence of SEQ ID NO: 156. In still another embodiment, the interleukin-21 variant lacks ten amino acids between S124 and S133 as set forth in an amino acid sequence of SEQ ID NO: 156.

In one embodiment, the interleukin-21 domain in the fusion protein provided herein has an amino acid sequence of SEQ ID NO: 156, 157, or 158. In another embodiment, the interleukin-21 domain in the fusion protein provided herein has an amino acid sequence of SEQ ID NO: 156. In yet another embodiment, the interleukin-21 domain in the fusion protein provided herein has an amino acid sequence of SEQ ID NO: 157. In yet another embodiment, the interleukin-21 domain in the fusion protein provided herein has an amino acid sequence of SEQ ID NO: 158.

In certain embodiments, the interleukin-21 domain in the fusion protein provided herein further includes one or more additional substitutions, deletions, and/or insertions; and/or one or more additional post-translational modifications.

In certain embodiments, the fusion protein has a dissociation constant to IL-21Rα ranging from about 1 pM to about 100 nM, from about 2 pM to about 10 nM, from about 5 pM to about 2 nM, or from about 10 pM to about 0.5 nM. In certain embodiments, the fusion protein has a dissociation constant to IL-21Rα ranging from about 1 pM to about 100 nM. In certain embodiments, the fusion protein has a dissociation constant to IL-21Rα ranging from about 2 pM to about 10 nM. In certain embodiments, the fusion protein has a dissociation constant to IL-21Rα ranging from about 5 pM to about 2 nM. In certain embodiments, the fusion protein has a dissociation constant to IL-21Rα ranging from about 10 pM to about 0.5 nM.

In one embodiment, each peptide linker in the fusion protein provided herein independently comprises a peptide linker having an amino acid sequence of GSG or one of SEQ ID NOs: 124 to 155. In another embodiment, each peptide linker in the fusion protein provided herein is independently a peptide linker having an amino acid sequence of GSG or one of SEQ ID NOs: 124 to 155.

In one embodiment, each peptide linker in the fusion protein provided herein independently comprises a GSG linker having an amino acid sequence of GSG or SEQ ID NO: 124, 125, or 126. In another embodiment, each peptide linker in the fusion protein provided herein is independently a GSG linker having an amino acid sequence of GSG or SEQ ID NO: 124, 125, or 126. In yet another embodiment, each peptide linker in the fusion protein provided herein independently comprises a G3S linker having an amino acid sequence of SEQ ID NO: 127, 128, 129, or 130. In yet another embodiment, each peptide linker in the fusion protein provided herein is independently a G3S linker having an amino acid sequence of SEQ ID NO: 127, 128, 129, or 130. In yet another embodiment, each peptide linker in the fusion protein provided herein independently comprises a G4S linker having an amino acid sequence of SEQ ID NO: 131, 132, 133, or 134. In yet another embodiment, each peptide linker in the fusion protein provided herein is independently a G4S linker having an amino acid sequence of SEQ ID NO: 131, 132, 133, or 134. In yet another embodiment, each peptide linker in the fusion protein provided herein independently comprises an SGSG linker having an amino acid sequence of SEQ ID NO: 135, 136, 137, or 138. In yet another embodiment, each peptide linker in the fusion protein provided herein is independently an SGSG linker having an amino acid sequence of SEQ ID NO: 135, 136, 137, or 138. In yet another embodiment, each peptide linker in the fusion protein provided herein independently comprises an SG3S linker having an amino acid sequence of SEQ ID NO: 139, 140, 141, or 142. In yet another embodiment, each peptide linker in the fusion protein provided herein is independently an SG3S linker having an amino acid sequence of SEQ ID NO: 139, 140, 141, or 142. In yet another embodiment, each peptide linker in the fusion protein provided herein independently comprises an SG4S linker having an amino acid sequence of SEQ ID NO: 143, 144, 145, or 146. In yet another embodiment, each peptide linker in the fusion protein provided herein is independently an SG4S linker having an amino acid sequence of SEQ ID NO: 143, 144, 145, or 146. In yet another embodiment, each peptide linker in the fusion protein provided herein independently comprises an EAAAK linker having an amino acid sequence of SEQ ID NO: 147, 148, 149, or 150. In yet another embodiment, each peptide linker in the fusion protein provided herein is independently an EAAAK linker having an amino acid sequence of SEQ ID NO: 147, 148, 149, or 150. In yet another embodiment, each peptide linker in the fusion protein provided herein independently comprises a PAPAP linker having an amino acid sequence of SEQ ID NO: 151, 152, 153, or 154. In yet another embodiment, each peptide linker in the fusion protein provided herein is independently a PAPAP linker having an amino acid sequence of SEQ ID NO: 151, 152, 153, or 154. In yet another embodiment, each peptide linker in the fusion protein provided herein independently comprises a linker having an amino acid sequence of SEQ ID NO: 155. In yet another embodiment, each peptide linker in the fusion protein provided herein is independently comprises a linker having an amino acid sequence of SEQ ID NO: 155.

In one embodiment, the first peptide linker in the fusion protein provided herein independently comprises a peptide linker having an amino acid sequence of GSG or one of SEQ ID NOs: 124 to 155. In another embodiment, the first peptide linker in the fusion protein provided herein is independently a peptide linker having an amino acid sequence of GSG or one of SEQ ID NOs: 124 to 155.

In one embodiment, the first peptide linker in the fusion protein provided herein independently comprises a GSG linker having an amino acid sequence of GSG or SEQ ID NO: 124, 125, or 126. In another embodiment, the first peptide linker in the fusion protein provided herein is independently a GSG linker having an amino acid sequence of GSG or SEQ ID NO: 124, 125, or 126. In yet another embodiment, the first peptide linker in the fusion protein provided herein independently comprises a G3S linker having an amino acid sequence of SEQ ID NO: 127, 128, 129, or 130. In yet another embodiment, the first peptide linker in the fusion protein provided herein is independently a G3S linker having an amino acid sequence of SEQ ID NO: 127, 128, 129, or 130. In yet another embodiment, the first peptide linker in the fusion protein provided herein independently comprises a G4S linker having an amino acid sequence of SEQ ID NO: 131, 132, 133, or 134. In yet another embodiment, the first peptide linker in the fusion protein provided herein is independently a G4S linker having an amino acid sequence of SEQ ID NO: 131, 132, 133, or 134. In yet another embodiment, the first peptide linker in the fusion protein provided herein independently comprises an SGSG linker having an amino acid sequence of SEQ ID NO: 135, 136, 137, or 138. In yet another embodiment, the first peptide linker in the fusion protein provided herein is independently an SGSG linker having an amino acid sequence of SEQ ID NO: 135, 136, 137, or 138. In yet another embodiment, the first peptide linker in the fusion protein provided herein independently comprises an SG3S linker having an amino acid sequence of SEQ ID NO: 139, 140, 141, or 142. In yet another embodiment, the first peptide linker in the fusion protein provided herein is independently an SG3S linker having an amino acid sequence of SEQ ID NO: 139, 140, 141, or 142. In yet another embodiment, the first peptide linker in the fusion protein provided herein independently comprises an SG4S linker having an amino acid sequence of SEQ ID NO: 143, 144, 145, or 146. In yet another embodiment, the first peptide linker in the fusion protein provided herein is independently an SG4S linker having an amino acid sequence of SEQ ID NO: 143, 144, 145, or 146. In yet another embodiment, the first peptide linker in the fusion protein provided herein independently comprises an EAAAK linker having an amino acid sequence of SEQ ID NO: 147, 148, 149, or 150. In yet another embodiment, the first peptide linker in the fusion protein provided herein is independently an EAAAK linker having an amino acid sequence of SEQ ID NO: 147, 148, 149, or 150. In yet another embodiment, the first peptide linker in the fusion protein provided herein independently comprises a PAPAP linker having an amino acid sequence of SEQ ID NO: 151, 152, 153, or 154. In yet another embodiment, the first peptide linker in the fusion protein provided herein is independently a PAPAP linker having an amino acid sequence of SEQ ID NO: 151, 152, 153, or 154. In yet another embodiment, the first peptide linker in the fusion protein provided herein independently comprises a linker having an amino acid sequence of SEQ ID NO: 155. In yet another embodiment, the first peptide linker in the fusion protein provided herein is independently comprises a linker having an amino acid sequence of SEQ ID NO: 155.

In one embodiment, the second peptide linker in the fusion protein provided herein independently comprises a peptide linker having an amino acid sequence of GSG or one of SEQ ID NOs: 124 to 155. In another embodiment, the second peptide linker in the fusion protein provided herein is independently a peptide linker having an amino acid sequence of GSG or one of SEQ ID NOs: 124 to 155.

In one embodiment, the second peptide linker in the fusion protein provided herein independently comprises a GSG linker having an amino acid sequence of GSG or SEQ ID NO: 124, 125, or 126. In another embodiment, the second peptide linker in the fusion protein provided herein is independently a GSG linker having an amino acid sequence of GSG or SEQ ID NO: 124, 125, or 126. In yet another embodiment, the second peptide linker in the fusion protein provided herein independently comprises a G3S linker having an amino acid sequence of SEQ ID NO: 127, 128, 129, or 130. In yet another embodiment, the second peptide linker in the fusion protein provided herein is independently a G3S linker having an amino acid sequence of SEQ ID NO: 127, 128, 129, or 130. In yet another embodiment, the second peptide linker in the fusion protein provided herein independently comprises a G4S linker having an amino acid sequence of SEQ ID NO: 131, 132, 133, or 134. In yet another embodiment, the second peptide linker in the fusion protein provided herein is independently a G4S linker having an amino acid sequence of SEQ ID NO: 131, 132, 133, or 134. In yet another embodiment, the second peptide linker in the fusion protein provided herein independently comprises an SGSG linker having an amino acid sequence of SEQ ID NO: 135, 136, 137, or 138. In yet another embodiment, the second peptide linker in the fusion protein provided herein is independently an SGSG linker having an amino acid sequence of SEQ ID NO: 135, 136, 137, or 138. In yet another embodiment, the second peptide linker in the fusion protein provided herein independently comprises an SG3S linker having an amino acid sequence of SEQ ID NO: 139, 140, 141, or 142. In yet another embodiment, the second peptide linker in the fusion protein provided herein is independently an SG3S linker having an amino acid sequence of SEQ ID NO: 139, 140, 141, or 142. In yet another embodiment, the second peptide linker in the fusion protein provided herein independently comprises an SG4S linker having an amino acid sequence of SEQ ID NO: 143, 144, 145, or 146. In yet another embodiment, the second peptide linker in the fusion protein provided herein is independently an SG4S linker having an amino acid sequence of SEQ ID NO: 143, 144, 145, or 146. In yet another embodiment, the second peptide linker in the fusion protein provided herein independently comprises an EAAAK linker having an amino acid sequence of SEQ ID NO: 147, 148, 149, or 150. In yet another embodiment, the second peptide linker in the fusion protein provided herein is independently an EAAAK linker having an amino acid sequence of SEQ ID NO: 147, 148, 149, or 150. In yet another embodiment, the second peptide linker in the fusion protein provided herein independently comprises a PAPAP linker having an amino acid sequence of SEQ ID NO: 151, 152, 153, or 154. In yet another embodiment, the second peptide linker in the fusion protein provided herein is independently a PAPAP linker having an amino acid sequence of SEQ ID NO: 151, 152, 153, or 154. In yet another embodiment, the second peptide linker in the fusion protein provided herein independently comprises a linker having an amino acid sequence of SEQ ID NO: 155. In yet another embodiment, the second peptide linker in the fusion protein provided herein is independently comprises a linker having an amino acid sequence of SEQ ID NO: 155.

In one embodiment, the third peptide linker in the fusion protein provided herein independently comprises a peptide linker having an amino acid sequence of GSG or one of SEQ ID NOs: 124 to 155. In another embodiment, the third peptide linker in the fusion protein provided herein is independently a peptide linker having an amino acid sequence of GSG or one of SEQ ID NOs: 124 to 155.

In one embodiment, the third peptide linker in the fusion protein provided herein independently comprises a GSG linker having an amino acid sequence of GSG or SEQ ID NO: 124, 125, or 126. In another embodiment, the third peptide linker in the fusion protein provided herein is independently a GSG linker having an amino acid sequence of GSG or SEQ ID NO: 124, 125, or 126. In yet another embodiment, the third peptide linker in the fusion protein provided herein independently comprises a G3S linker having an amino acid sequence of SEQ ID NO: 127, 128, 129, or 130. In yet another embodiment, the third peptide linker in the fusion protein provided herein is independently a G3S linker having an amino acid sequence of SEQ ID NO: 127, 128, 129, or 130. In yet another embodiment, the third peptide linker in the fusion protein provided herein independently comprises a G4S linker having an amino acid sequence of SEQ ID NO: 131, 132, 133, or 134. In yet another embodiment, the third peptide linker in the fusion protein provided herein is independently a G4S linker having an amino acid sequence of SEQ ID NO: 131, 132, 133, or 134. In yet another embodiment, the third peptide linker in the fusion protein provided herein independently comprises an SGSG linker having an amino acid sequence of SEQ ID NO: 135, 136, 137, or 138. In yet another embodiment, the third peptide linker in the fusion protein provided herein is independently an SGSG linker having an amino acid sequence of SEQ ID NO: 135, 136, 137, or 138. In yet another embodiment, the third peptide linker in the fusion protein provided herein independently comprises an SG3S linker having an amino acid sequence of SEQ ID NO: 139, 140, 141, or 142. In yet another embodiment, the third peptide linker in the fusion protein provided herein is independently an SG3S linker having an amino acid sequence of SEQ ID NO: 139, 140, 141, or 142. In yet another embodiment, the third peptide linker in the fusion protein provided herein independently comprises an SG4S linker having an amino acid sequence of SEQ ID NO: 143, 144, 145, or 146. In yet another embodiment, the third peptide linker in the fusion protein provided herein is independently an SG4S linker having an amino acid sequence of SEQ ID NO: 143, 144, 145, or 146. In yet another embodiment, the third peptide linker in the fusion protein provided herein independently comprises an EAAAK linker having an amino acid sequence of SEQ ID NO: 147, 148, 149, or 150. In yet another embodiment, the third peptide linker in the fusion protein provided herein is independently an EAAAK linker having an amino acid sequence of SEQ ID NO: 147, 148, 149, or 150. In yet another embodiment, the third peptide linker in the fusion protein provided herein independently comprises a PAPAP linker having an amino acid sequence of SEQ ID NO: 151, 152, 153, or 154. In yet another embodiment, the third peptide linker in the fusion protein provided herein is independently a PAPAP linker having an amino acid sequence of SEQ ID NO: 151, 152, 153, or 154. In yet another embodiment, the third peptide linker in the fusion protein provided herein independently comprises a linker having an amino acid sequence of SEQ ID NO: 155. In yet another embodiment, the third peptide linker in the fusion protein provided herein is independently comprises a linker having an amino acid sequence of SEQ ID NO: 155.

In one embodiment, the fourth peptide linker in the fusion protein provided herein independently comprises a peptide linker having an amino acid sequence of GSG or one of SEQ ID NOs: 124 to 155. In another embodiment, the fourth peptide linker in the fusion protein provided herein is independently a peptide linker having an amino acid sequence of GSG or one of SEQ ID NOs: 124 to 155.

In one embodiment, the fourth peptide linker in the fusion protein provided herein independently comprises a GSG linker having an amino acid sequence of GSG or SEQ ID NO: 124, 125, or 126. In another embodiment, the fourth peptide linker in the fusion protein provided herein is independently a GSG linker having an amino acid sequence of GSG or SEQ ID NO: 124, 125, or 126. In yet another embodiment, the fourth peptide linker in the fusion protein provided herein independently comprises a G3S linker having an amino acid sequence of SEQ ID NO: 127, 128, 129, or 130. In yet another embodiment, the fourth peptide linker in the fusion protein provided herein is independently a G3S linker having an amino acid sequence of SEQ ID NO: 127, 128, 129, or 130. In yet another embodiment, the fourth peptide linker in the fusion protein provided herein independently comprises a G4S linker having an amino acid sequence of SEQ ID NO: 131, 132, 133, or 134. In yet another embodiment, the fourth peptide linker in the fusion protein provided herein is independently a G4S linker having an amino acid sequence of SEQ ID NO: 131, 132, 133, or 134. In yet another embodiment, the fourth peptide linker in the fusion protein provided herein independently comprises an SGSG linker having an amino acid sequence of SEQ ID NO: 135, 136, 137, or 138. In yet another embodiment, the fourth peptide linker in the fusion protein provided herein is independently an SGSG linker having an amino acid sequence of SEQ ID NO: 135, 136, 137, or 138. In yet another embodiment, the fourth peptide linker in the fusion protein provided herein independently comprises an SG3S linker having an amino acid sequence of SEQ ID NO: 139, 140, 141, or 142. In yet another embodiment, the fourth peptide linker in the fusion protein provided herein is independently an SG3S linker having an amino acid sequence of SEQ ID NO: 139, 140, 141, or 142. In yet another embodiment, the fourth peptide linker in the fusion protein provided herein independently comprises an SG4S linker having an amino acid sequence of SEQ ID NO: 143, 144, 145, or 146. In yet another embodiment, the fourth peptide linker in the fusion protein provided herein is independently an SG4S linker having an amino acid sequence of SEQ ID NO: 143, 144, 145, or 146. In yet another embodiment, the fourth peptide linker in the fusion protein provided herein independently comprises an EAAAK linker having an amino acid sequence of SEQ ID NO: 147, 148, 149, or 150. In yet another embodiment, the fourth peptide linker in the fusion protein provided herein is independently an EAAAK linker having an amino acid sequence of SEQ ID NO: 147, 148, 149, or 150. In yet another embodiment, the fourth peptide linker in the fusion protein provided herein independently comprises a PAPAP linker having an amino acid sequence of SEQ ID NO: 151, 152, 153, or 154. In yet another embodiment, the fourth peptide linker in the fusion protein provided herein is independently a PAPAP linker having an amino acid sequence of SEQ ID NO: 151, 152, 153, or 154. In yet another embodiment, the fourth peptide linker in the fusion protein provided herein independently comprises a linker having an amino acid sequence of SEQ ID NO: 155. In yet another embodiment, the fourth peptide linker in the fusion protein provided herein is independently comprises a linker having an amino acid sequence of SEQ ID NO: 155.

In one embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one $V_HH$ single domain antibody having an amino acid sequence of SEQ ID NOs: 108 or 115; and optionally one or two peptide linkers, each independently having an amino acid sequence of GSG or any one of SEQ ID NOs: 124 to 155.

In another embodiment, provided herein is a fusion protein comprising one interleukin-2 domain having an amino acid sequence of SEQ ID NO: 2 or 8; one interleukin-21 domain having an amino acid sequence of SEQ ID NO: 156 or 157; one $V_HH$ single domain antibody having an amino acid sequence of SEQ ID NO: 108 or 115; and optionally one or two peptide linkers, each independently having an amino acid sequence of SEQ ID NO: 126 or 133.

In yet another embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one $V_HH$ single domain antibody having an amino acid sequence of SEQ ID NOs: 108 or 115; and one peptide linker having an amino acid sequence of GSG or any one of SEQ ID NOs: 124 to 155; wherein the C-terminus of the interleukin-2 domain is connected to the N-terminus of the peptide linker, the C-terminus of the peptide linker is connected to the N-terminus of the $V_HH$ single domain antibody, and the C-terminus of the $V_HH$ single domain antibody is connected to the N-terminus of the interleukin-21 domain; or wherein the C-terminus of the interleukin-21 domain is connected to the N-terminus of the $V_HH$ single domain antibody, the C-terminus of the $V_HH$ single domain antibody is connected to the N-terminus of the peptide linker, and the C-terminus of the peptide linker is connected to the N-terminus of the interleukin-2 domain.

In yet another embodiment, provided herein is a fusion protein comprising one interleukin-2 domain having an amino acid sequence of SEQ ID NO: 2 or 8; one interleukin-21 domain having an amino acid sequence of SEQ ID NO:

156 or 157; one V$_H$H single domain antibody having an amino acid sequence of SEQ ID NO: 108 or 115; and one peptide linker having an amino acid sequence of SEQ ID NO: 126 or 133; wherein the C-terminus of the interleukin-2 domain is connected to the N-terminus of the peptide linker, the C-terminus of the peptide linker is connected to the N-terminus of the V$_H$H single domain antibody, and the C-terminus of the V$_H$H single domain antibody is connected to the N-terminus of the interleukin-21 domain; or wherein the C-terminus of the interleukin-21 domain is connected to the N-terminus of the V$_H$H single domain antibody, the C-terminus of the V$_H$H single domain antibody is connected to the N-terminus of the peptide linker, and the C-terminus of the peptide linker is connected to the N-terminus of the interleukin-2 domain.

In still another embodiment, provided herein is an interleukin-2 and interleukin-21 fusion protein having an amino acid sequence of any one of SEQ ID NOs: 159 to 171.

In one embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one Fc domain having an amino acid sequence of any one of SEQ ID NOs: 116 to 123; and optionally one or two peptide linkers, each independently having an amino acid sequence of GSG or any one of SEQ ID NOs: 124 to 155.

In another embodiment, provided herein is a fusion protein comprising two interleukin-2 domains, each independently having an amino acid sequence of any one of SEQ ID NOs: 1 to 97; one interleukin-21 domain having an amino acid sequence of any one of SEQ ID NOs: 156 to 158; one Fc domain having an amino acid sequence of any one of SEQ ID NOs: 116 to 123; and optionally one, two, or three peptide linkers, each independently having an amino acid sequence of GSG or any one of SEQ ID NOs: 124 to 155.

In one embodiment, the fusion protein provided herein is produced from a yeast cell, insect cell, mammalian cell, a human cell, or a plant cell. In another embodiment, the fusion protein provided herein is produced from a yeast cell. In yet another embodiment, the fusion protein provided herein is produced from an insect cell. In yet another embodiment, the fusion protein provided herein is produced from a mammalian cell. In yet another embodiment, the fusion protein provided herein is produced from a CHO cell. In yet another embodiment, the fusion protein provided herein is produced from a human cell. In yet another embodiment, the fusion protein provided herein is produced from a plant cell.

Pharmaceutical Compositions

In one embodiment, provided herein is a pharmaceutical composition comprising a fusion protein provided herein and a pharmaceutically acceptable excipient.

In one embodiment, the pharmaceutical composition is formulated as single dosage form.

In one embodiment, the pharmaceutical composition provided herein is a solid formulation. In another embodiment, the pharmaceutical composition provided herein is a lyophilized solid formulation. In yet another embodiment, the pharmaceutical composition provided herein is a solution. In yet another embodiment, the pharmaceutical composition provided herein is an aqueous solution. In still another embodiment, the pharmaceutical composition provided herein is sterilized.

In one embodiment, the pharmaceutical composition provided herein is formulated in a dosage form for parenteral administration. In another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for intratumoral administration.

Methods of Use

In one embodiment, provided herein is a method for treating, preventing, or ameliorating a proliferative disease in a subject, comprising administering to the subject in need thereof a therapeutically effective amount of a fusion protein provided herein.

In one embodiment, the proliferative disease is cancer. In another embodiment, the proliferative disease is metastatic cancer. In yet another embodiment, the proliferative disease is renal cell carcinoma (RCC) or melanoma. In yet another embodiment, the proliferative disease is metastatic renal cell carcinoma (RCC) or metastatic melanoma.

In another embodiment, provided herein is a method of activating an immune effector cell, comprising contacting the cell with an effective amount of a fusion protein provided herein.

In certain embodiments, the therapeutically effective amount is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

In certain embodiments, the subject is a mammal. In certain embodiments, the subject is a human.

The disclosure will be further understood by the following non-limiting examples.

EXAMPLES

Example 1

Cloning, Expression, and Purification of IL-2 and IL-21 Fusion Proteins

The amino acid sequences of the human IL-2 and IL-21 were obtained from UNIPROT (IL-2: P60568, 21-153 aa; IL-21: Q9HBE4, 25-162 aa). The deoxyoligonucleotide sequences encoding the human IL-2 and IL-21 were codon optimized for CHO cell expression. The deoxyoligonucleotide sequences of the human IL-2, IL-21, and their muteins were commercially synthesized.

Figure 4:
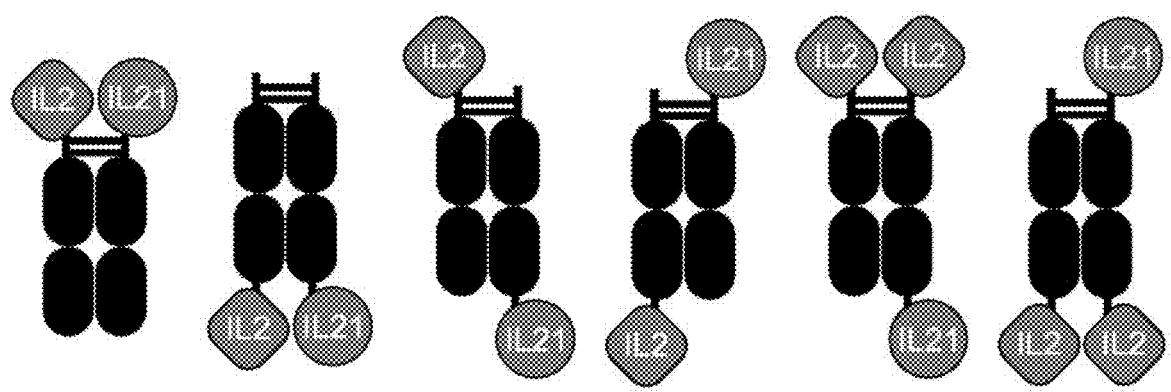
FIG. 4 shows the configurations of exemplary fusion proteins comprising an IL-2 domain, an IL-21 domain, and an Fc domain with two peptide chains as an example of a half-life extension domain.
Figure 5:
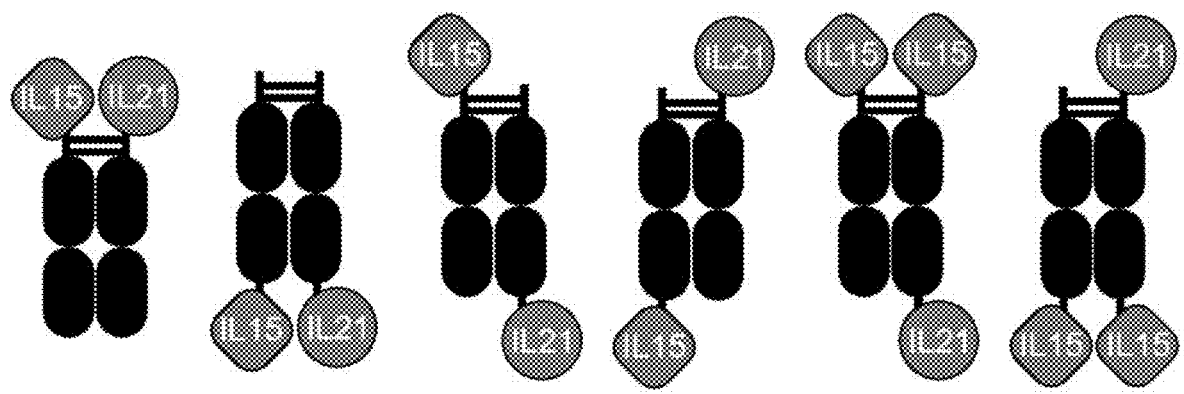
FIG. 5 shows the configurations of exemplary fusion proteins comprising an IL-15 domain, an IL-21 domain, and an Fc domain with two peptide chains as an example of a half-life extension domain.
Figure 6:
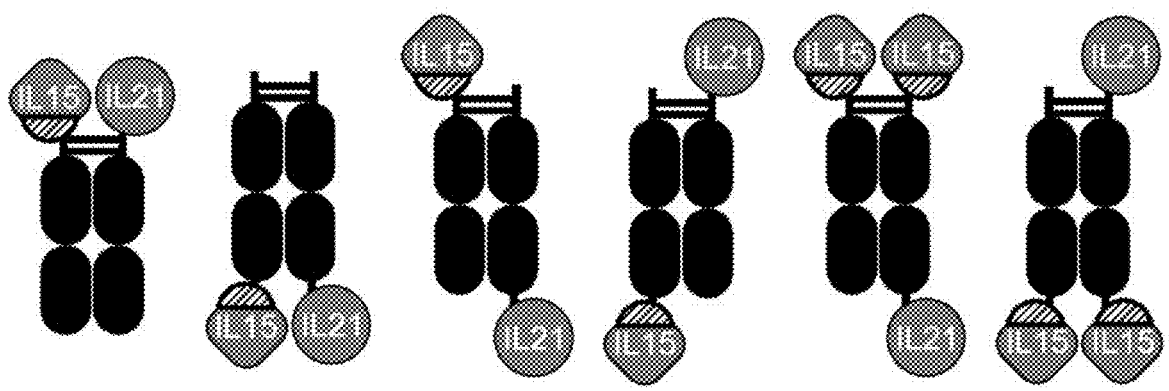
FIG. 6 shows the configurations of exemplary fusion proteins comprising an IL-15 variant domain, an IL-21 domain, and an Fc domain with two peptide chains as an example of a half-life extension domain.
Figure 7:
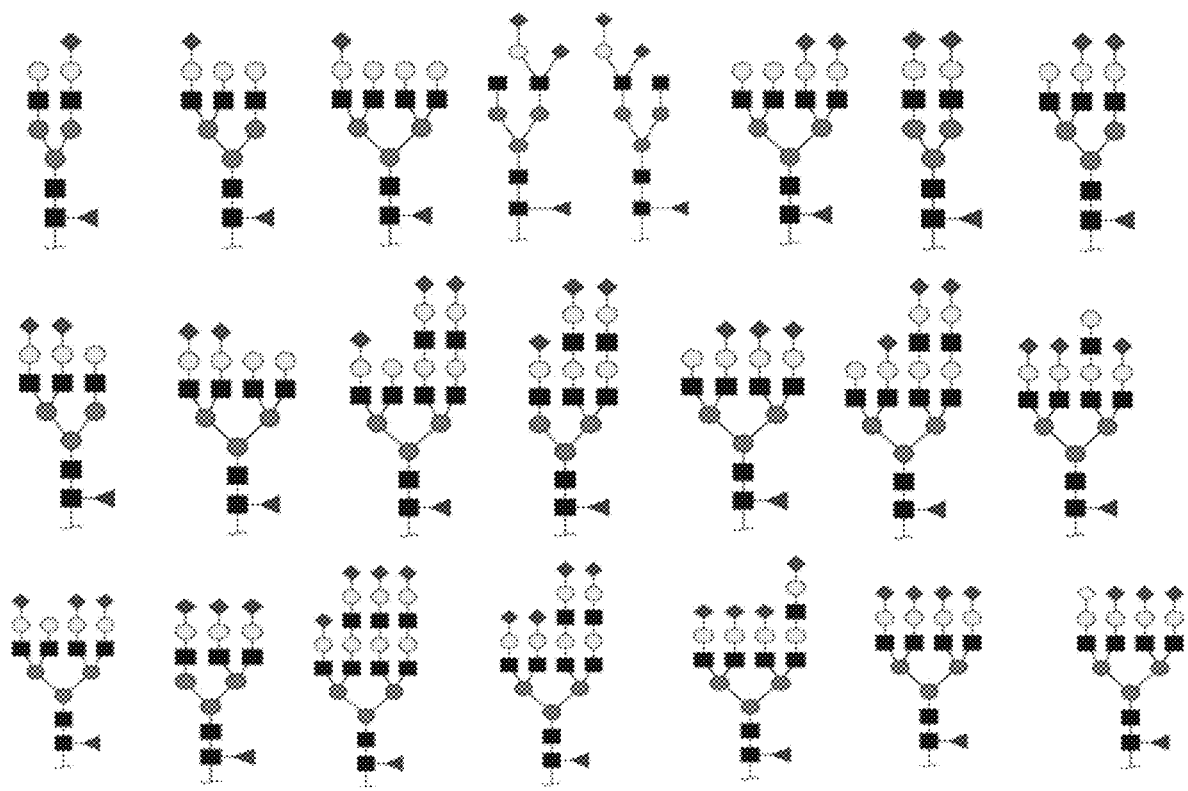
FIG. 7 illustrates the structures of certain N-glycans.

Certain configurations of fusion proteins containing (i) the human IL-2 or a mutein thereof, (ii) the human IL-21 or a mutein thereof, and (iii) an anti-human serum albumin (HSA) antibody are illustrated in FIG. 1. Certain configurations of fusion proteins containing (i) the human IL-2 or a mutein thereof, (ii) the human IL-21 or a mutein thereof, and (iii) a human IgG Fc or a mutein thereof are illustrated in FIG. 4.

The deoxyoligonucleotide sequences encoding the human IL-2, IL-21, peptide linkers, and an anti-HSA V$_H$H antibody or human IgG Fc were seamlessly assembled together by homology assembly cloning with commercially available kits. The oligonucleotides of the fusion proteins were each independently inserted into a UCOE® expression vector CET1019-AS-Puro for CHO cell expression.

The oligonucleotide sequence encoding a fusion protein was transiently expressed in EXPICHO™ cells. Briefly, on Day −1, EXPICHO-S™ cells were seeded at 3-4×10⁶ cells/mL with the EXPICHO™ expression medium in a vented Erlenmeyer shake flask. The flask was placed on a 125 rpm orbital shaker in a 37° C. incubator with 8% $CO_2$. On Day 0, plasmid DNA was mixed with the EXPIFECTAMINE™ CHO reagent. The mixture was then slowly added to the cells. After 16 hours, the cells were transferred to a 32° C. incubator with 5% $CO_2$. The cells were fed twice on Day 1 and Day 5 with the EXPICHO™ feed. The CHO cells were harvested on Day 8-12.

The fusion proteins produced in the CHO cells were purified by a two-step purification process comprising protein A affinity chromatography using protein A (e.g., AMSPHERE™ A3) resin and ion exchange chromatography (e.g., CAPTO™ S IMPACT).

For the protein A affinity chromatography, a protein A affinity column was loaded with a clarified CHO medium and then washed twice with 20 mM sodium phosphate and once with 20 mM sodium phosphate with 0.5 M NaCl at pH 7.5. The fusion protein was eluted with 50 mM sodium acetate at pH 3.0 supplied with 1% isopropanol by volume.

The purified fusion protein was then buffer exchanged into 20 mM sodium phosphate at pH 6.0 in preparation of AKTA™ purification. The fusion protein was loaded onto 1 mL HITRAP CAPTO™ S IMPACT column. After loading, the column was washed with 20 mM sodium phosphate at pH 6.0 for 10 column volumes (CV). After washing, the fusion protein was eluted with 20 mM sodium phosphate at pH 6.0 plus 1 M NaCl by a gradient of 0-100% in 22.5 CV. The fusion protein was eluted off at ~12 mS/cm. Eluted fractions were pooled and buffer exchanged into a solution containing 5 mM histidine, 20 mM NaCl, and 0.02% TWEEN-80 at pH 4.0 for storage.

Example 2

Effect of IL-2/IL-21 Fusion Proteins on STAT3 Signaling

The IL-2/IL-21 fusion proteins were evaluated in a STAT3 signaling assay.

Pfeiffer cells were maintained in RPMI-1640 containing 10% fetal bovine serum and penicillin/streptomycin. The Pfeiffer cells (100,000) were treated with a hIL-21-anti-HSA fusion protein (C1) as a control; or IL-2/IL-21 fusion proteins for 30 minutes at 37° C. and 5% $CO_2$ in Hanks balanced salt solution containing 10 mM HEPES. Phospho-STAT3 was measured using a phospho-STAT3 (Tyr705) homogeneous time resolved fluorescence (HTRF) assay. The signal ratio at 665 nm/620 nm was multiplied by 1000, plotted, and fit using a dose response curve (GRAPHPAD PRISM) to calculate $EC_{50}$ values. The $EC_{50}$ values determined are summarized in Table 1 below.

In the table, C1 represents a hIL-21-anti-HSA fusion protein comprising an IL-21 domain of an amino acid sequence of SEQ ID NO: 156 and an sdAb of SEQ ID NO: 108, where the C-terminus of the IL-21 domain is connected directly to the N-terminus of the sdAb.

A1 represents an IL-2/IL-21 fusion protein of SEQ ID NO: 159, which comprises an IL-2 domain of SEQ ID NO: 2, an IL-21 domain of SEQ ID NO: 156, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

A2 represents an IL-2/IL-21 fusion protein of SEQ ID NO: 160, which comprises an IL-2 domain of SEQ ID NO: 20, an IL-21 domain of SEQ ID NO: 156, an sdAb of SEQ ID NO: 108, and a peptide linker of SEQ ID NO: 126, where the C-terminus of the IL-2 domain is connected directly to the N-terminus of the peptide linker, the N-terminus of which is connected directly to the C-terminus of the sdAb, the N-terminus of which is connected directly to the C-terminus of the IL-21 domain.

A3 represents an IL-2/IL-21 fusion protein of SEQ ID NO: 161, which comprises an IL-2 domain of SEQ ID NO: 20, an IL-21 domain of SEQ ID NO: 156, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

A4 represents an IL-2/IL-21 fusion protein of SEQ ID NO: 163, which comprises an IL-2 domain of SEQ ID NO: 20, an IL-21 domain of SEQ ID NO: 157, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

TABLE 1

|  | C1 | A1 | A2 | A3 | A4 |
|---|---|---|---|---|---|
| $EC_{50}$ (pM) | 95 | 82 | 89 | 61 | 199 |

The results show that the IL-2/IL-21 fusion proteins have similar signaling potency as the hIL-21-anti-HSA fusion protein (C1) in activating the STAT3 signaling pathway.

Example 3

Effect of IL-2/IL-21 Fusion Proteins on STAT5 Signaling

The IL-2/IL-21 fusion proteins were evaluated in a STAT5 signaling assay.

Lousy cells were maintained in RPMI-1640 containing 10% fetal bovine serum and penicillin/streptomycin. The Loucy cells (100,000) were treated with a hIL-2-anti-HSA fusion protein (hIL-2-anti-HSA (C2) or hIL-2 mutant-anti-HSA (C3)) as a control, or IL-2/IL-21 fusion proteins for 30 minutes at 37° C. and 5% $CO_2$ in the Hanks balanced salt solution containing 10 mM HEPES. Phospho-STAT5 was measured using a phospho-STAT5 (Tyr694) homogeneous time resolved fluorescence (HTRF) assay. The signal ratio at 665 nm/620 nm was multiplied by 1000, plotted, and fit using a dose response curve (GRAPHPAD PRISM) to calculate $EC_{50}$ values. The $EC_{50}$ values determined are summarized in Table 2 below.

In the table, C2 represents a hIL-2-anti-HSA fusion protein comprising an IL-2 domain of an amino acid sequence of SEQ ID NO: 2, an sdAb of SEQ ID NO: 108, and a peptide linker of SEQ ID NO: 126, where the C-terminus of the IL-2 domain is connected directly to the N-terminus of the peptide linker, the C-terminus of which is connected directly to the N-terminus of the sdAb. C3 represents a hIL-2-anti-HSA fusion protein comprising an IL-2 domain of an amino acid sequence of SEQ ID NO: 20, an sdAb of SEQ ID NO: 108, and a peptide linker of SEQ ID NO: 126, where the C-terminus of the IL-2 domain is connected directly to the N-terminus of the peptide linker, the C-terminus of which is connected directly to the N-terminus of the sdAb.

TABLE 2

|  | C2 | C3 | A1 | A2 | A3 | A4 |
|---|---|---|---|---|---|---|
| $EC_{50}$ (nM) | 9.0 | 5.1 | 1.5 | 2.2 | 1.6 | 3.2 |

The results show that the IL-2/IL-21 fusion proteins have better signaling potency compared to hIL-2-anti-HSA (C2) and glycosylated hIL-2-anti-HSA (C3) in cells that only express IL-2Rβ and IL-2Rγ.

Example 4

In Vitro Potency of IL-2/IL-21 Fusion Proteins with CD3/CD28 Activated T-Cells

The in vitro potency of hIL-21-anti-HSA (C1), hIL-2-anti-HSA (C2), or fusion proteins (A1, A2, and A3) was determined by quantifying improvement in N87 (stomach cancer) cell killing by CD3/CD28 stimulated CD3+ T-cell.

The N87 cancer cells were maintained in RPMI-1640 containing 10% fetal bovine serum and penicillin/streptomycin. On Day 0, 10,000 N87 cells/well were plated in the culture medium in a 96-well flat bottom plate. On Day 1, 30,000 CD3+ T cells/well and 1:300 diluted anti-CD3/anti-CD28 antibody complex were added to the cancer cells together with hIL-21-anti-HAS (C1), hIL-2-anti-HSA (C2), or fusion proteins (A1, A2, and A3). The plates were incubated for 72 h at 37° C. and 5% $CO_2$. The cells were then fixed with 4% paraformaldehyde and nuclei stained with SYTOX™ Orange. The number of remaining cancer cells was calculated by counting the number of cancer cell nuclei remaining in each well using the CYTATION™ 1. The $IC_{50}$ values determined are summarized in Table 3 below.

TABLE 3

|  | C1 | C2 | A1 | A2 | A3 |
|---|---|---|---|---|---|
| $IC_{50}$ (pM) | 13.7 | 9.8 | 5.4 | 3.4 | 1.6 |

Example 5

Binding Studies of IL-2/IL-21 Fusion Proteins to Human IL-2Rα

OCTET® RED96 is used to characterize the interactions of IL-2/IL-21 fusion proteins with a human IL-2Rα. Briefly, an IL-2Rα-Fc fusion protein is loaded onto an anti-human IgG Fc capture (AHC) biosensor. The biosensor is then dipped into a solution containing an IL-2/IL-21 fusion protein at 100, 200, 400, or 800 nM. Primary experimental data is analyzed with global fitting to determine a dissociation constant ($K_d$).

Example 6

Binding Studies of IL-2/IL-21 Fusion Proteins to Human IL-2Rβ

OCTET® RED96 is used to characterize the interactions of IL-2/IL-21 fusion proteins with a human IL-2Rβ. Briefly, an IL-2Rβ-Fc fusion protein is loaded onto an anti-human IgG Fc capture (AHC) biosensor. The biosensor is then dipped into a solution containing an IL-2/IL-21 fusion protein at 200, 400, or 800 nM. Primary experimental data is analyzed with global fitting to determine a dissociation constant ($K_d$).

Example 7

Glycan Analysis

The glycan profile of a fusion protein is analyzed using an ADVANCEBIO GLY-X™ N-glycan prep with INSTANTPC™ kit. The domain is denatured and N-glycans are released by an N-glycanase at 50° C. The released N-glycans are labeled by an INSTANTPC™ dye and then cleaned up with a Gly-X™. The labeled glycans are analyzed on an HPLC system equipped with an ACQUITY UPLC Glycan BEH Amide column (130 Å, 1.7 μm, 2.1 mm×150 mm) connected to a Shimadzu NEXERA-I LC-2040C 3D MT coupled with a RF-20A fluorescence detector. The N-glycans are identified by comparing them with the INSTANTPC™ labeled glycan standard libraries from Agilent Technologies.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of activating STAT3 and STAT5 signaling pathways in a subject with cancer, comprising administering to the subject a therapeutically effective amount of a fusion protein comprising an interleukin-2 domain, an interleukin-21 domain, and an albumin binding domain:

wherein the interleukin-2 domain comprises the amino acid sequence of SEQ ID NO: 1, 2, 3, 4, or 5; or wherein the interleukin-2 domain is an N-glycosylated interleukin-2 comprising one, two, three, or four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in the amino acid sequence of SEQ ID NO: 1, 2, 3, 4, or 5;

wherein the interleukin-21 domain comprises the amino acid sequence of SEQ ID NO: 156, 157, or 158; and wherein the C-terminus of the interleukin-2 domain is connected to the N-terminus of the interleukin-21 domain directly or via a peptide linker; and the C-terminus of the interleukin-21 domain is connected to the N-terminus of the albumin binding domain directly or via a peptide linker; or wherein the C-terminus of the interleukin-21 domain is connected to the N-terminus of the interleukin-2 domain directly or via a peptide linker; and the C-terminus of the interleukin-2 domain is connected to the N-terminus of the albumin binding domain directly or via a peptide linker; or wherein the C-terminus of the interleukin-2 domain is connected to the N-terminus of the albumin binding domain directly or via a peptide linker; and the C-terminus of the albumin binding domain is connected to the N-terminus of the interleukin-21 domain directly or via a peptide linker; or wherein the C-terminus of the interleukin-21 domain is connected to the N-terminus of the albumin binding domain directly or via a peptide linker; and the C-terminus of the albumin binding domain is connected to the N-terminus of the interleukin-2 domain directly or via a peptide linker; or wherein the C-terminus of the albumin binding domain is connected to the N-terminus of the interleukin-2 domain directly or via a peptide linker; and the C-terminus of the interleukin-2 domain is connected to the N-terminus of the interleukin-21 domain directly or via a peptide linker; or wherein the C-terminus of the albumin binding domain is connected to the N-terminus of the interleukin-21 domain directly or via a peptide linker; and the C-terminus of the interleukin-21 domain is connected to the N-terminus of the interleukin-2 domain directly or via a peptide linker.

2. The method of claim 1, wherein the fusion protein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

3. The method of claim 1, wherein the fusion protein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

4. The method of claim 1, wherein the albumin binding domain of the fusion protein is a single domain antibody.

5. The method of claim 4, wherein the single domain antibody of the fusion protein comprises: (i) CDR1 of SEQ ID NO: 101, CDR2 of SEQ ID NO: 102, and CDR3 of SEQ ID NO: 103; or (ii) CDR1 of SEQ ID NO: 109, CDR2 of SEQ ID NO: 110, and CDR3 of SEQ ID NO: 111.

6. The method of claim 1, wherein the interleukin-2 domain of the fusion protein comprises one, two, three, or four, substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in the amino acid sequence of SEQ ID NO: 1, 2, 3, 4, or 5.

7. The method of claim 6, wherein the interleukin-2 domain of the fusion protein comprises four substitutions at positions R38, L40, F42, and Y45 as set forth in the amino acid sequence of SEQ ID NO: 1, 2, 3, 4, or 5.

8. The method of claim 1, wherein the interleukin-2 domain of the fusion protein comprises an N-glycosylation site having the amino acid sequence of NXT or NXS, wherein each X is independently A, C, D, E, F, G, H, I, K, L, M, N, Q, R, S, T, V, W, or Y.

9. The method of claim 1, wherein the interleukin-2 domain of the fusion protein comprises an N-glycosylation site having the amino acid sequence of NMT or NMS, each independently starting at position 38 or 45 as set forth in the amino acid sequence of SEQ ID NO: 1, 2, 3, 4, or 5.

10. The method of claim 1, wherein the interleukin-2 domain of the fusion protein comprises an N-glycosylation site at an interface residue between an interleukin-2 and an interleukin-2 receptor-α chain.

11. The method of claim 10, wherein the interface residue is R38 as set forth in the amino acid sequence of SEQ ID NO: 1, 2, 3, 4, or 5.

12. The method of claim 1, wherein the interleukin-2 domain of the fusion protein comprises two amino acid substitutions: (i) R38N and (ii) L40T or L40S as set forth in the amino acid sequence of SEQ ID NO: 1, 2, 3, 4, or 5.

13. The method of claim 1, wherein the interleukin-2 domain of the fusion protein comprises three amino acid substitutions: (i) R38N, (ii) L40T or L40S, and (iii) F42A, Y45A, E61A, or E62A, as set forth in the amino acid sequence of SEQ ID NO: 1, 2, 3, 4, or 5.

14. The method of claim 1, wherein the interleukin-2 domain of the fusion protein comprises four amino acid substitutions: (i) R38N, (ii) L40T or L40S, (iii) K43N, or (iv) Y45T or Y45S, as set forth in the amino acid sequence of SEQ ID NO: 1, 2, 3, 4, or 5.

15. The method of claim 1, wherein the interleukin-2 domain of the fusion protein comprises the amino acid sequence selected from SEQ ID NOs: 1 to 5 and 18.

16. The method of claim 1, wherein the interleukin-2 domain of the fusion protein comprises the amino acid sequence selected from SEQ ID NOs: 1 to 5.

17. The method of claim 1, wherein the interleukin-2 domain of the fusion protein comprises the amino acid sequence of SEQ ID NO: 18.

18. The method of claim 1, wherein the interleukin-21 domain of the fusion protein comprises the amino acid sequence of SEQ ID NO: 156 or 157.

19. The method of claim 1, wherein each peptide linker is independently a peptide linker having the amino acid sequence of GSG or one of SEQ ID NOs: 124 to 155.

20. The method of claim 1, wherein the fusion protein comprises one interleukin-2 domain having the amino acid sequence of any one of SEQ ID NOs: 1 to 5 and 18; one interleukin-21 domain having the amino acid sequence of any one of SEQ ID NOs: 156 to 158; one $V_H H$ single domain antibody having the amino acid sequence of SEQ ID NO: 108 or 115; and optionally one or two peptide linkers, each independently having the amino acid sequence of GSG or any one of SEQ ID NOs: 124 to 155.

21. The method of claim 1, wherein the fusion protein comprises one interleukin-2 domain having the amino acid sequence of SEQ ID NO: 2 or 18; one interleukin-21 domain having the amino acid sequence of SEQ ID NO: 156 or 157; one $V_H H$ single domain antibody having the amino acid sequence of SEQ ID NO: 108 or 115; and optionally one or two peptide linkers, each independently having the amino acid sequence of SEQ ID NO: 126 or 133.

22. The method of claim 1, wherein the fusion protein comprises one interleukin-2 domain having the amino acid sequence of any one of SEQ ID NOs: 1 to 5 and 18; one interleukin-21 domain having the amino acid sequence of any one of SEQ ID NOs: 156 to 158; one $V_H H$ single domain antibody having the amino acid sequence of SEQ ID NO: 108 or 115; and one peptide linker having the amino acid sequence of GSG or any one of SEQ ID NOs: 124 to 155; wherein the C-terminus of the interleukin-2 domain is connected to the N-terminus of the peptide linker, the C-terminus of the peptide linker is connected to the N-terminus of the $V_H H$ single domain antibody, and the C-terminus of the $V_H H$ single domain antibody is connected to the N-terminus of the interleukin-21 domain; or wherein the C-terminus of the interleukin-21 domain is connected to the N-terminus of the $V_H H$ single domain antibody, the C-terminus of the $V_H H$ single domain antibody is connected to the N-terminus of the peptide linker, and the C-terminus of the peptide linker is connected to the N-terminus of the interleukin-2 domain.

23. The method of claim 1, wherein the fusion protein comprises one interleukin-2 domain having the amino acid sequence of SEQ ID NO: 2 or 18; one interleukin-21 domain having the amino acid sequence of SEQ ID NO: 156 or 157; one $V_H H$ single domain antibody having the amino acid sequence of SEQ ID NO: 108 or 115; and one peptide linker having the amino acid sequence of SEQ ID NO: 126 or 133; wherein the C-terminus of the interleukin-2 domain is connected to the N-terminus of the peptide linker, the C-terminus of the peptide linker is connected to the N-terminus of the $V_H H$ single domain antibody, and the C-terminus of the $V_H H$ single domain antibody is connected to the N-terminus of the interleukin-21 domain; or wherein the C-terminus of the interleukin-21 domain is connected to the N-terminus of the $V_H H$ single domain antibody, the C-terminus of the $V_H H$ single domain antibody is connected to the N-terminus of the peptide linker, and the C-terminus of the peptide linker is connected to the N-terminus of the interleukin-2 domain.

24. The method of claim 1, wherein the fusion protein has the amino acid sequence selected from SEQ ID NOs: 159 to 163 and 166 to 171.

25. The method of claim 1, wherein the cancer is metastatic cancer.

26. The method of claim 1, wherein the cancer is renal cell carcinoma (RCC).

27. The method of claim 26, wherein the cancer is metastatic renal cell carcinoma (RCC).

28. The method of claim 4, wherein the single domain antibody of the fusion protein has the amino acid sequence of SEQ ID NO: 108.

29. The method of claim 4, wherein the single domain antibody of the fusion protein has the amino acid sequence of SEQ ID NO: 115.

* * * * *

SEQUENCE LISTING

```
Sequence total quantity: 172
SEQ ID NO: 1           moltype = AA  length = 133
FEATURE                Location/Qualifiers
source                 1..133
                       mol_type = protein
                       organism = Homo sapiens
SEQUENCE: 1
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 2           moltype = AA  length = 133
FEATURE                Location/Qualifiers
source                 1..133
```

```
                        mol_type = protein
                        organism = Homo sapiens
SEQUENCE: 2
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 3            moltype = AA  length = 133
FEATURE                 Location/Qualifiers
source                  1..133
                        mol_type = protein
                        organism = Homo sapiens
SEQUENCE: 3
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLT                                                      133

SEQ ID NO: 4            moltype = AA  length = 133
FEATURE                 Location/Qualifiers
source                  1..133
                        mol_type = protein
                        organism = Homo sapiens
SEQUENCE: 4
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 5            moltype = AA  length = 133
FEATURE                 Location/Qualifiers
source                  1..133
                        mol_type = protein
                        organism = Homo sapiens
SEQUENCE: 5
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFAQSIIS TLT                                                      133

SEQ ID NO: 6            moltype = AA  length = 133
FEATURE                 Location/Qualifiers
source                  1..133
                        mol_type = protein
                        organism = Homo sapiens
SEQUENCE: 6
APTSSSTKKT QLQLEHLLLD LQMILNGINN YKNNKTTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 7            moltype = AA  length = 133
FEATURE                 Location/Qualifiers
source                  1..133
                        mol_type = protein
                        organism = Homo sapiens
SEQUENCE: 7
APTSSSTKKT QLQLEHLLLD LQMILNGINN YKNNKSTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 8            moltype = AA  length = 133
FEATURE                 Location/Qualifiers
source                  1..133
                        mol_type = protein
                        organism = Homo sapiens
SEQUENCE: 8
APASSSTKKT QLQLEHLLLD LQMILNGINN YKNNKTTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 9            moltype = AA  length = 133
FEATURE                 Location/Qualifiers
source                  1..133
                        mol_type = protein
                        organism = Homo sapiens
SEQUENCE: 9
APASSSTKKT QLQLEHLLLD LQMILNGINN YKNNKSTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 10           moltype = AA  length = 133
FEATURE                 Location/Qualifiers
```

```
source                  1..133
                        mol_type = protein
                        organism = Homo sapiens
SEQUENCE: 10
APTSSSTKKT QLQLEHLLLD LQMILNGINN YKNPNLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 11           moltype = AA  length = 133
FEATURE                 Location/Qualifiers
source                  1..133
                        mol_type = protein
                        organism = Homo sapiens
SEQUENCE: 11
APTSSSTKKT QLQLEHLLLD LQMILNGINN YKNPNLSRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 12           moltype = AA  length = 133
FEATURE                 Location/Qualifiers
source                  1..133
                        mol_type = protein
                        organism = Homo sapiens
SEQUENCE: 12
APASSSTKKT QLQLEHLLLD LQMILNGINN YKNPNLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 13           moltype = AA  length = 133
FEATURE                 Location/Qualifiers
source                  1..133
                        mol_type = protein
                        organism = Homo sapiens
SEQUENCE: 13
APASSSTKKT QLQLEHLLLD LQMILNGINN YKNPNLSRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 14           moltype = AA  length = 133
FEATURE                 Location/Qualifiers
source                  1..133
                        mol_type = protein
                        organism = Homo sapiens
SEQUENCE: 14
APTSSSTKKT QLQLEHLLLD LQMILNGINN YKNPKLNRTL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 15           moltype = AA  length = 133
FEATURE                 Location/Qualifiers
source                  1..133
                        mol_type = protein
                        organism = Homo sapiens
SEQUENCE: 15
APTSSSTKKT QLQLEHLLLD LQMILNGINN YKNPKLNRSL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 16           moltype = AA  length = 133
FEATURE                 Location/Qualifiers
source                  1..133
                        mol_type = protein
                        organism = Homo sapiens
SEQUENCE: 16
APASSSTKKT QLQLEHLLLD LQMILNGINN YKNPKLNRTL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 17           moltype = AA  length = 133
FEATURE                 Location/Qualifiers
source                  1..133
                        mol_type = protein
                        organism = Homo sapiens
SEQUENCE: 17
APASSSTKKT QLQLEHLLLD LQMILNGINN YKNPKLNRSL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 18           moltype = AA  length = 133
```

```
FEATURE               Location/Qualifiers
source                1..133
                      mol_type = protein
                      organism = Homo sapiens
SEQUENCE: 18
APTSSSTKKT QLQLEHLLLD LQMILNGINN YKNPKLTNMT TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 19         moltype = AA  length = 133
FEATURE               Location/Qualifiers
source                1..133
                      mol_type = protein
                      organism = Homo sapiens
SEQUENCE: 19
APTSSSTKKT QLQLEHLLLD LQMILNGINN YKNPKLTNMS TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 20         moltype = AA  length = 133
FEATURE               Location/Qualifiers
source                1..133
                      mol_type = protein
                      organism = Homo sapiens
SEQUENCE: 20
APASSSTKKT QLQLEHLLLD LQMILNGINN YKNPKLTNMT TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 21         moltype = AA  length = 133
FEATURE               Location/Qualifiers
source                1..133
                      mol_type = protein
                      organism = Homo sapiens
SEQUENCE: 21
APASSSTKKT QLQLEHLLLD LQMILNGINN YKNPKLTNMS TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 22         moltype = AA  length = 133
FEATURE               Location/Qualifiers
source                1..133
                      mol_type = protein
                      organism = Homo sapiens
SEQUENCE: 22
APTSSSTKKT QLQLEHLLLD LQMILNGINN YKNPKLTRML NFTFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 23         moltype = AA  length = 133
FEATURE               Location/Qualifiers
source                1..133
                      mol_type = protein
                      organism = Homo sapiens
SEQUENCE: 23
APTSSSTKKT QLQLEHLLLD LQMILNGINN YKNPKLTRML NFSFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 24         moltype = AA  length = 133
FEATURE               Location/Qualifiers
source                1..133
                      mol_type = protein
                      organism = Homo sapiens
SEQUENCE: 24
APASSSTKKT QLQLEHLLLD LQMILNGINN YKNPKLTRML NFTFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 25         moltype = AA  length = 133
FEATURE               Location/Qualifiers
source                1..133
                      mol_type = protein
                      organism = Homo sapiens
SEQUENCE: 25
APASSSTKKT QLQLEHLLLD LQMILNGINN YKNPKLTRML NFSFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133
```

```
SEQ ID NO: 26               moltype = AA  length = 133
FEATURE                     Location/Qualifiers
source                      1..133
                            mol_type = protein
                            organism = Homo sapiens
SEQUENCE: 26
APTSSSTKKT QLQLEHLLLD LQMILNGINN YKNPKLTRML TNKTYMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 27               moltype = AA  length = 133
FEATURE                     Location/Qualifiers
source                      1..133
                            mol_type = protein
                            organism = Homo sapiens
SEQUENCE: 27
APTSSSTKKT QLQLEHLLLD LQMILNGINN YKNPKLTRML TNKSYMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 28               moltype = AA  length = 133
FEATURE                     Location/Qualifiers
source                      1..133
                            mol_type = protein
                            organism = Homo sapiens
SEQUENCE: 28
APASSSTKKT QLQLEHLLLD LQMILNGINN YKNPKLTRML TNKTYMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 29               moltype = AA  length = 133
FEATURE                     Location/Qualifiers
source                      1..133
                            mol_type = protein
                            organism = Homo sapiens
SEQUENCE: 29
APASSSTKKT QLQLEHLLLD LQMILNGINN YKNPKLTRML TNKSYMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 30               moltype = AA  length = 133
FEATURE                     Location/Qualifiers
source                      1..133
                            mol_type = protein
                            organism = Homo sapiens
SEQUENCE: 30
APTSSSTKKT QLQLEHLLLD LQMILNGINN YKNPKLTRML TFNFTMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 31               moltype = AA  length = 133
FEATURE                     Location/Qualifiers
source                      1..133
                            mol_type = protein
                            organism = Homo sapiens
SEQUENCE: 31
APTSSSTKKT QLQLEHLLLD LQMILNGINN YKNPKLTRML TFNFSMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 32               moltype = AA  length = 133
FEATURE                     Location/Qualifiers
source                      1..133
                            mol_type = protein
                            organism = Homo sapiens
SEQUENCE: 32
APASSSTKKT QLQLEHLLLD LQMILNGINN YKNPKLTRML TFNFTMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133

SEQ ID NO: 33               moltype = AA  length = 133
FEATURE                     Location/Qualifiers
source                      1..133
                            mol_type = protein
                            organism = Homo sapiens
SEQUENCE: 33
APASSSTKKT QLQLEHLLLD LQMILNGINN YKNPKLTRML TFNFSMPKKA TELKHLQCLE    60
EELKPLEEVL NLAQSKNFHL RPRDLISNIN VIVLELKGSE TTFMCEYADE TATIVEFLNR    120
WITFSQSIIS TLT                                                       133
```

```
SEQ ID NO: 34          moltype = AA   length = 133
FEATURE                Location/Qualifiers
source                 1..133
                       mol_type = protein
                       organism = Homo sapiens
SEQUENCE: 34
APTSSSTKKT QLQLEHLLLD LQMILNGINN YKNPKLTRML TFKNYTPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 35          moltype = AA   length = 133
FEATURE                Location/Qualifiers
source                 1..133
                       mol_type = protein
                       organism = Homo sapiens
SEQUENCE: 35
APTSSSTKKT QLQLEHLLLD LQMILNGINN YKNPKLTRML TFKNYSPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 36          moltype = AA   length = 133
FEATURE                Location/Qualifiers
source                 1..133
                       mol_type = protein
                       organism = Homo sapiens
SEQUENCE: 36
APASSSTKKT QLQLEHLLLD LQMILNGINN YKNPKLTRML TFKNYTPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 37          moltype = AA   length = 133
FEATURE                Location/Qualifiers
source                 1..133
                       mol_type = protein
                       organism = Homo sapiens
SEQUENCE: 37
APASSSTKKT QLQLEHLLLD LQMILNGINN YKNPKLTRML TFKNYSPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 38          moltype = AA   length = 133
FEATURE                Location/Qualifiers
source                 1..133
                       mol_type = protein
                       organism = Homo sapiens
SEQUENCE: 38
APTSSSTKKT QLQLEHLLLD LQMILNGINN YKNPKLTRML TFKFNMTKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 39          moltype = AA   length = 133
FEATURE                Location/Qualifiers
source                 1..133
                       mol_type = protein
                       organism = Homo sapiens
SEQUENCE: 39
APTSSSTKKT QLQLEHLLLD LQMILNGINN YKNPKLTRML TFKFNMSKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 40          moltype = AA   length = 133
FEATURE                Location/Qualifiers
source                 1..133
                       mol_type = protein
                       organism = Homo sapiens
SEQUENCE: 40
APASSSTKKT QLQLEHLLLD LQMILNGINN YKNPKLTRML TFKFNMTKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 41          moltype = AA   length = 133
FEATURE                Location/Qualifiers
source                 1..133
                       mol_type = protein
                       organism = Homo sapiens
SEQUENCE: 41
APASSSTKKT QLQLEHLLLD LQMILNGINN YKNPKLTRML TFKFNMSKKA TELKHLQCLE    60
EELKPLEEVL NLAQSKNFHL RPRDLISNIN VIVLELKGSE TTFMCEYADE TATIVEFLNR   120
```

-continued

```
WITFSQSIIS TLT                                                         133

SEQ ID NO: 42           moltype = AA  length = 133
FEATURE                 Location/Qualifiers
source                  1..133
                        mol_type = protein
                        organism = Homo sapiens
SEQUENCE: 42
APTSSSTKKT QLQLEHLLLD LQMILNGINN YKNPKLTRML TFKFYMPKKA TELKHLQCLE        60
NETKPLEEVL NLAQSKNFHL RPRDLISNIN VIVLELKGSE TTFMCEYADE TATIVEFLNR       120
WITFSQSIIS TLT                                                         133

SEQ ID NO: 43           moltype = AA  length = 133
FEATURE                 Location/Qualifiers
source                  1..133
                        mol_type = protein
                        organism = Homo sapiens
SEQUENCE: 43
APTSSSTKKT QLQLEHLLLD LQMILNGINN YKNPKLTRML TFKFYMPKKA TELKHLQCLE        60
NESKPLEEVL NLAQSKNFHL RPRDLISNIN VIVLELKGSE TTFMCEYADE TATIVEFLNR       120
WITFSQSIIS TLT                                                         133

SEQ ID NO: 44           moltype = AA  length = 133
FEATURE                 Location/Qualifiers
source                  1..133
                        mol_type = protein
                        organism = Homo sapiens
SEQUENCE: 44
APASSSTKKT QLQLEHLLLD LQMILNGINN YKNPKLTRML TFKFYMPKKA TELKHLQCLE        60
NETKPLEEVL NLAQSKNFHL RPRDLISNIN VIVLELKGSE TTFMCEYADE TATIVEFLNR       120
WITFSQSIIS TLT                                                         133

SEQ ID NO: 45           moltype = AA  length = 133
FEATURE                 Location/Qualifiers
source                  1..133
                        mol_type = protein
                        organism = Homo sapiens
SEQUENCE: 45
APASSSTKKT QLQLEHLLLD LQMILNGINN YKNPKLTRML TFKFYMPKKA TELKHLQCLE        60
NESKPLEEVL NLAQSKNFHL RPRDLISNIN VIVLELKGSE TTFMCEYADE TATIVEFLNR       120
WITFSQSIIS TLT                                                         133

SEQ ID NO: 46           moltype = AA  length = 133
FEATURE                 Location/Qualifiers
source                  1..133
                        mol_type = protein
                        organism = Homo sapiens
SEQUENCE: 46
APTSSSTKKT QLQLEHLLLD LQMILNGINN YKNPKLTRML TFKFYMPKKA TELKHLQCLE        60
ENLTPLEEVL NLAQSKNFHL RPRDLISNIN VIVLELKGSE TTFMCEYADE TATIVEFLNR       120
WITFSQSIIS TLT                                                         133

SEQ ID NO: 47           moltype = AA  length = 133
FEATURE                 Location/Qualifiers
source                  1..133
                        mol_type = protein
                        organism = Homo sapiens
SEQUENCE: 47
APTSSSTKKT QLQLEHLLLD LQMILNGINN YKNPKLTRML TFKFYMPKKA TELKHLQCLE        60
ENLSPLEEVL NLAQSKNFHL RPRDLISNIN VIVLELKGSE TTFMCEYADE TATIVEFLNR       120
WITFSQSIIS TLT                                                         133

SEQ ID NO: 48           moltype = AA  length = 133
FEATURE                 Location/Qualifiers
source                  1..133
                        mol_type = protein
                        organism = Homo sapiens
SEQUENCE: 48
APASSSTKKT QLQLEHLLLD LQMILNGINN YKNPKLTRML TFKFYMPKKA TELKHLQCLE        60
ENLTPLEEVL NLAQSKNFHL RPRDLISNIN VIVLELKGSE TTFMCEYADE TATIVEFLNR       120
WITFSQSIIS TLT                                                         133

SEQ ID NO: 49           moltype = AA  length = 133
FEATURE                 Location/Qualifiers
source                  1..133
                        mol_type = protein
                        organism = Homo sapiens
SEQUENCE: 49
APASSSTKKT QLQLEHLLLD LQMILNGINN YKNPKLTRML TFKFYMPKKA TELKHLQCLE        60
```

```
ENLSPLEEVL NLAQSKNFHL RPRDLISNIN VIVLELKGSE TTFMCEYADE TATIVEFLNR    120
WITFSQSIIS TLT                                                      133

SEQ ID NO: 50           moltype = AA  length = 133
FEATURE                 Location/Qualifiers
source                  1..133
                        mol_type = protein
                        organism = Homo sapiens
SEQUENCE: 50
APTSSSTKKT QLQLEHLLLD LQMILNGINN YKNPKLTRML TFKFYMPKKA TELKHLQCLE    60
EELNATEEVL NLAQSKNFHL RPRDLISNIN VIVLELKGSE TTFMCEYADE TATIVEFLNR    120
WITFSQSIIS TLT                                                      133

SEQ ID NO: 51           moltype = AA  length = 133
FEATURE                 Location/Qualifiers
source                  1..133
                        mol_type = protein
                        organism = Homo sapiens
SEQUENCE: 51
APTSSSTKKT QLQLEHLLLD LQMILNGINN YKNPKLTRML TFKFYMPKKA TELKHLQCLE    60
EELNASEEVL NLAQSKNFHL RPRDLISNIN VIVLELKGSE TTFMCEYADE TATIVEFLNR    120
WITFSQSIIS TLT                                                      133

SEQ ID NO: 52           moltype = AA  length = 133
FEATURE                 Location/Qualifiers
source                  1..133
                        mol_type = protein
                        organism = Homo sapiens
SEQUENCE: 52
APASSSTKKT QLQLEHLLLD LQMILNGINN YKNPKLTRML TFKFYMPKKA TELKHLQCLE    60
EELNATEEVL NLAQSKNFHL RPRDLISNIN VIVLELKGSE TTFMCEYADE TATIVEFLNR    120
WITFSQSIIS TLT                                                      133

SEQ ID NO: 53           moltype = AA  length = 133
FEATURE                 Location/Qualifiers
source                  1..133
                        mol_type = protein
                        organism = Homo sapiens
SEQUENCE: 53
APASSSTKKT QLQLEHLLLD LQMILNGINN YKNPKLTRML TFKFYMPKKA TELKHLQCLE    60
EELNASEEVL NLAQSKNFHL RPRDLISNIN VIVLELKGSE TTFMCEYADE TATIVEFLNR    120
WITFSQSIIS TLT                                                      133

SEQ ID NO: 54           moltype = AA  length = 133
FEATURE                 Location/Qualifiers
source                  1..133
                        mol_type = protein
                        organism = Homo sapiens
SEQUENCE: 54
APTSSSTKKT QLQLEHLLLD LQMILNGINN YKNPKLTRML TFKFYMPKKA TELKHLQCLE    60
EELKNLTEVL NLAQSKNFHL RPRDLISNIN VIVLELKGSE TTFMCEYADE TATIVEFLNR    120
WITFSQSIIS TLT                                                      133

SEQ ID NO: 55           moltype = AA  length = 133
FEATURE                 Location/Qualifiers
source                  1..133
                        mol_type = protein
                        organism = Homo sapiens
SEQUENCE: 55
APTSSSTKKT QLQLEHLLLD LQMILNGINN YKNPKLTRML TFKFYMPKKA TELKHLQCLE    60
EELKNLSEVL NLAQSKNFHL RPRDLISNIN VIVLELKGSE TTFMCEYADE TATIVEFLNR    120
WITFSQSIIS TLT                                                      133

SEQ ID NO: 56           moltype = AA  length = 133
FEATURE                 Location/Qualifiers
source                  1..133
                        mol_type = protein
                        organism = Homo sapiens
SEQUENCE: 56
APASSSTKKT QLQLEHLLLD LQMILNGINN YKNPKLTRML TFKFYMPKKA TELKHLQCLE    60
EELKNLTEVL NLAQSKNFHL RPRDLISNIN VIVLELKGSE TTFMCEYADE TATIVEFLNR    120
WITFSQSIIS TLT                                                      133

SEQ ID NO: 57           moltype = AA  length = 133
FEATURE                 Location/Qualifiers
source                  1..133
                        mol_type = protein
                        organism = Homo sapiens
SEQUENCE: 57
```

```
APASSSTKKT QLQLEHLLLD LQMILNGINN YKNPKLTRML TFKFYMPKKA TELKHLQCLE    60
EELKNLSEVL NLAQSKNFHL RPRDLISNIN VIVLELKGSE TTFMCEYADE TATIVEFLNR   120
WITFSQSIIS TLT                                                     133

SEQ ID NO: 58           moltype = AA  length = 133
FEATURE                 Location/Qualifiers
source                  1..133
                        mol_type = protein
                        organism = Homo sapiens
SEQUENCE: 58
APTSSSTKKT QLQLEHLLLD LQMILNGINN YKNPKLTRML TFKFYMPKKA TELKHLQCLE    60
EELKPNETVL NLAQSKNFHL RPRDLISNIN VIVLELKGSE TTFMCEYADE TATIVEFLNR   120
WITFSQSIIS TLT                                                     133

SEQ ID NO: 59           moltype = AA  length = 133
FEATURE                 Location/Qualifiers
source                  1..133
                        mol_type = protein
                        organism = Homo sapiens
SEQUENCE: 59
APTSSSTKKT QLQLEHLLLD LQMILNGINN YKNPKLTRML TFKFYMPKKA TELKHLQCLE    60
EELKPNESVL NLAQSKNFHL RPRDLISNIN VIVLELKGSE TTFMCEYADE TATIVEFLNR   120
WITFSQSIIS TLT                                                     133

SEQ ID NO: 60           moltype = AA  length = 133
FEATURE                 Location/Qualifiers
source                  1..133
                        mol_type = protein
                        organism = Homo sapiens
SEQUENCE: 60
APASSSTKKT QLQLEHLLLD LQMILNGINN YKNPKLTRML TFKFYMPKKA TELKHLQCLE    60
EELKPNETVL NLAQSKNFHL RPRDLISNIN VIVLELKGSE TTFMCEYADE TATIVEFLNR   120
WITFSQSIIS TLT                                                     133

SEQ ID NO: 61           moltype = AA  length = 133
FEATURE                 Location/Qualifiers
source                  1..133
                        mol_type = protein
                        organism = Homo sapiens
SEQUENCE: 61
APASSSTKKT QLQLEHLLLD LQMILNGINN YKNPKLTRML TFKFYMPKKA TELKHLQCLE    60
EELKPNESVL NLAQSKNFHL RPRDLISNIN VIVLELKGSE TTFMCEYADE TATIVEFLNR   120
WITFSQSIIS TLT                                                     133

SEQ ID NO: 62           moltype = AA  length = 133
FEATURE                 Location/Qualifiers
source                  1..133
                        mol_type = protein
                        organism = Homo sapiens
SEQUENCE: 62
APTSSSTKKT QLQLEHLLLD LQMILNGINN YKNPKLTRML TFKFYMPKKA TELKHLQCLE    60
EELKPLENVT NLAQSKNFHL RPRDLISNIN VIVLELKGSE TTFMCEYADE TATIVEFLNR   120
WITFSQSIIS TLT                                                     133

SEQ ID NO: 63           moltype = AA  length = 133
FEATURE                 Location/Qualifiers
source                  1..133
                        mol_type = protein
                        organism = Homo sapiens
SEQUENCE: 63
APTSSSTKKT QLQLEHLLLD LQMILNGINN YKNPKLTRML TFKFYMPKKA TELKHLQCLE    60
EELKPLENVS NLAQSKNFHL RPRDLISNIN VIVLELKGSE TTFMCEYADE TATIVEFLNR   120
WITFSQSIIS TLT                                                     133

SEQ ID NO: 64           moltype = AA  length = 133
FEATURE                 Location/Qualifiers
source                  1..133
                        mol_type = protein
                        organism = Homo sapiens
SEQUENCE: 64
APASSSTKKT QLQLEHLLLD LQMILNGINN YKNPKLTRML TFKFYMPKKA TELKHLQCLE    60
EELKPLENVT NLAQSKNFHL RPRDLISNIN VIVLELKGSE TTFMCEYADE TATIVEFLNR   120
WITFSQSIIS TLT                                                     133

SEQ ID NO: 65           moltype = AA  length = 133
FEATURE                 Location/Qualifiers
source                  1..133
                        mol_type = protein
                        organism = Homo sapiens
```

```
SEQUENCE: 65
APASSSTKKT QLQLEHLLLD LQMILNGINN YKNPKLTRML TFKFYMPKKA TELKHLQCLE    60
EELKPLENVS NLAQSKNFHL RPRDLISNIN VIVLELKGSE TTFMCEYADE TATIVEFLNR   120
WITFSQSIIS TLT                                                     133

SEQ ID NO: 66           moltype = AA  length = 133
FEATURE                 Location/Qualifiers
source                  1..133
                        mol_type = protein
                        organism = Homo sapiens
SEQUENCE: 66
APTSSSTKKT QLQLEHLLLD LQMILNGINN YKNPKLTRML TFKFYMPKKA TELKHLQCLE    60
EELKPLEENL TLAQSKNFHL RPRDLISNIN VIVLELKGSE TTFMCEYADE TATIVEFLNR   120
WITFSQSIIS TLT                                                     133

SEQ ID NO: 67           moltype = AA  length = 133
FEATURE                 Location/Qualifiers
source                  1..133
                        mol_type = protein
                        organism = Homo sapiens
SEQUENCE: 67
APTSSSTKKT QLQLEHLLLD LQMILNGINN YKNPKLTRML TFKFYMPKKA TELKHLQCLE    60
EELKPLEENL SLAQSKNFHL RPRDLISNIN VIVLELKGSE TTFMCEYADE TATIVEFLNR   120
WITFSQSIIS TLT                                                     133

SEQ ID NO: 68           moltype = AA  length = 133
FEATURE                 Location/Qualifiers
source                  1..133
                        mol_type = protein
                        organism = Homo sapiens
SEQUENCE: 68
APASSSTKKT QLQLEHLLLD LQMILNGINN YKNPKLTRML TFKFYMPKKA TELKHLQCLE    60
EELKPLEENL TLAQSKNFHL RPRDLISNIN VIVLELKGSE TTFMCEYADE TATIVEFLNR   120
WITFSQSIIS TLT                                                     133

SEQ ID NO: 69           moltype = AA  length = 133
FEATURE                 Location/Qualifiers
source                  1..133
                        mol_type = protein
                        organism = Homo sapiens
SEQUENCE: 69
APASSSTKKT QLQLEHLLLD LQMILNGINN YKNPKLTRML TFKFYMPKKA TELKHLQCLE    60
EELKPLEENL SLAQSKNFHL RPRDLISNIN VIVLELKGSE TTFMCEYADE TATIVEFLNR   120
WITFSQSIIS TLT                                                     133

SEQ ID NO: 70           moltype = AA  length = 133
FEATURE                 Location/Qualifiers
source                  1..133
                        mol_type = protein
                        organism = Homo sapiens
SEQUENCE: 70
APTSSSTKKT QLQLEHLLLD LQMILNGINN YKNPKLTRML TFKFYMPKKA TELKHLQCLE    60
EELKPLEEVL NLTQSKNFHL RPRDLISNIN VIVLELKGSE TTFMCEYADE TATIVEFLNR   120
WITFSQSIIS TLT                                                     133

SEQ ID NO: 71           moltype = AA  length = 133
FEATURE                 Location/Qualifiers
source                  1..133
                        mol_type = protein
                        organism = Homo sapiens
SEQUENCE: 71
APTSSSTKKT QLQLEHLLLD LQMILNGINN YKNPKLTRML TFKFYMPKKA TELKHLQCLE    60
EELKPLEEVL NLSQSKNFHL RPRDLISNIN VIVLELKGSE TTFMCEYADE TATIVEFLNR   120
WITFSQSIIS TLT                                                     133

SEQ ID NO: 72           moltype = AA  length = 133
FEATURE                 Location/Qualifiers
source                  1..133
                        mol_type = protein
                        organism = Homo sapiens
SEQUENCE: 72
APASSSTKKT QLQLEHLLLD LQMILNGINN YKNPKLTRML TFKFYMPKKA TELKHLQCLE    60
EELKPLEEVL NLTQSKNFHL RPRDLISNIN VIVLELKGSE TTFMCEYADE TATIVEFLNR   120
WITFSQSIIS TLT                                                     133

SEQ ID NO: 73           moltype = AA  length = 133
FEATURE                 Location/Qualifiers
source                  1..133
                        mol_type = protein
```

```
                        organism = Homo sapiens
SEQUENCE: 73
APASSSTKKT QLQLEHLLLD LQMILNGINN YKNPKLTRML TFKFYMPKKA TELKHLQCLE    60
EELKPLEEVL NLSQSKNFHL RPRDLISNIN VIVLELKGSE TTFMCEYADE TATIVEFLNR   120
WITFSQSIIS TLT                                                      133

SEQ ID NO: 74           moltype = AA  length = 133
FEATURE                 Location/Qualifiers
source                  1..133
                        mol_type = protein
                        organism = Homo sapiens
SEQUENCE: 74
APTSSSTKKT QLQLEHLLLD LQMILNGINN YKNPKLTRML TFKFYMPKKA TELKHLQCLE    60
EELKPLEEVL NNATSKNFHL RPRDLISNIN VIVLELKGSE TTFMCEYADE TATIVEFLNR   120
WITFSQSIIS TLT                                                      133

SEQ ID NO: 75           moltype = AA  length = 133
FEATURE                 Location/Qualifiers
source                  1..133
                        mol_type = protein
                        organism = Homo sapiens
SEQUENCE: 75
APTSSSTKKT QLQLEHLLLD LQMILNGINN YKNPKLTRML TFKFYMPKKA TELKHLQCLE    60
EELKPLEEVL NNASSKNFHL RPRDLISNIN VIVLELKGSE TTFMCEYADE TATIVEFLNR   120
WITFSQSIIS TLT                                                      133

SEQ ID NO: 76           moltype = AA  length = 133
FEATURE                 Location/Qualifiers
source                  1..133
                        mol_type = protein
                        organism = Homo sapiens
SEQUENCE: 76
APASSSTKKT QLQLEHLLLD LQMILNGINN YKNPKLTRML TFKFYMPKKA TELKHLQCLE    60
EELKPLEEVL NNATSKNFHL RPRDLISNIN VIVLELKGSE TTFMCEYADE TATIVEFLNR   120
WITFSQSIIS TLT                                                      133

SEQ ID NO: 77           moltype = AA  length = 133
FEATURE                 Location/Qualifiers
source                  1..133
                        mol_type = protein
                        organism = Homo sapiens
SEQUENCE: 77
APASSSTKKT QLQLEHLLLD LQMILNGINN YKNPKLTRML TFKFYMPKKA TELKHLQCLE    60
EELKPLEEVL NNASSKNFHL RPRDLISNIN VIVLELKGSE TTFMCEYADE TATIVEFLNR   120
WITFSQSIIS TLT                                                      133

SEQ ID NO: 78           moltype = AA  length = 133
FEATURE                 Location/Qualifiers
source                  1..133
                        mol_type = protein
                        organism = Homo sapiens
SEQUENCE: 78
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCENATE TATIVEFLNR   120
WITFSQSIIS TLT                                                      133

SEQ ID NO: 79           moltype = AA  length = 133
FEATURE                 Location/Qualifiers
source                  1..133
                        mol_type = protein
                        organism = Homo sapiens
SEQUENCE: 79
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCENASE TATIVEFLNR   120
WITFSQSIIS TLT                                                      133

SEQ ID NO: 80           moltype = AA  length = 133
FEATURE                 Location/Qualifiers
source                  1..133
                        mol_type = protein
                        organism = Homo sapiens
SEQUENCE: 80
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCENATE TATIVEFLNR   120
WITFSQSIIS TLT                                                      133

SEQ ID NO: 81           moltype = AA  length = 133
FEATURE                 Location/Qualifiers
source                  1..133
```

```
                        mol_type = protein
                        organism = Homo sapiens
SEQUENCE: 81
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCENASE TATIVEFLNR   120
WITFSQSIIS TLT                                                      133

SEQ ID NO: 82           moltype = AA  length = 133
FEATURE                 Location/Qualifiers
source                  1..133
                        mol_type = protein
                        organism = Homo sapiens
SEQUENCE: 82
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYANE TATIVEFLNR   120
WITFSQSIIS TLT                                                      133

SEQ ID NO: 83           moltype = AA  length = 133
FEATURE                 Location/Qualifiers
source                  1..133
                        mol_type = protein
                        organism = Homo sapiens
SEQUENCE: 83
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYANE SATIVEFLNR   120
WITFSQSIIS TLT                                                      133

SEQ ID NO: 84           moltype = AA  length = 133
FEATURE                 Location/Qualifiers
source                  1..133
                        mol_type = protein
                        organism = Homo sapiens
SEQUENCE: 84
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYANE TATIVEFLNR   120
WITFSQSIIS TLT                                                      133

SEQ ID NO: 85           moltype = AA  length = 133
FEATURE                 Location/Qualifiers
source                  1..133
                        mol_type = protein
                        organism = Homo sapiens
SEQUENCE: 85
APASSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYANE SATIVEFLNR   120
WITFSQSIIS TLT                                                      133

SEQ ID NO: 86           moltype = AA  length = 133
FEATURE                 Location/Qualifiers
source                  1..133
                        mol_type = protein
                        organism = Homo sapiens
SEQUENCE: 86
APTSSSTKKT QLQLEHLLLD LQMILNGINN YKNPKLTRNL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 87           moltype = AA  length = 133
FEATURE                 Location/Qualifiers
source                  1..133
                        mol_type = protein
                        organism = Homo sapiens
SEQUENCE: 87
APASSSTKKT QLQLEHLLLD LQMILNGINN YKNPKLTRNL TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 88           moltype = AA  length = 133
FEATURE                 Location/Qualifiers
source                  1..133
                        mol_type = protein
                        organism = Homo sapiens
SEQUENCE: 88
APTSSSTKKT QLQLEHLLLD LQMILNGINN YKNPKLTNMT TFNFTMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                      133

SEQ ID NO: 89           moltype = AA  length = 133
FEATURE                 Location/Qualifiers
```

```
source                     1..133
                           mol_type = protein
                           organism = Homo sapiens
SEQUENCE: 89
APASSSTKKT QLQLEHLLLD LQMILNGINN YKNPKLTNMT TFNFTMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 90              moltype = AA   length = 133
FEATURE                    Location/Qualifiers
source                     1..133
                           mol_type = protein
                           organism = Homo sapiens
SEQUENCE: 90
APTSSSTKKT QLQLEHLLLD LQMILNGINN YKNPKLTNMT TAKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 91              moltype = AA   length = 133
FEATURE                    Location/Qualifiers
source                     1..133
                           mol_type = protein
                           organism = Homo sapiens
SEQUENCE: 91
APASSSTKKT QLQLEHLLLD LQMILNGINN YKNPKLTNMT TAKFYMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 92              moltype = AA   length = 133
FEATURE                    Location/Qualifiers
source                     1..133
                           mol_type = protein
                           organism = Homo sapiens
SEQUENCE: 92
APTSSSTKKT QLQLEHLLLD LQMILNGINN YKNPKLTNMT TFKFAMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 93              moltype = AA   length = 133
FEATURE                    Location/Qualifiers
source                     1..133
                           mol_type = protein
                           organism = Homo sapiens
SEQUENCE: 93
APASSSTKKT QLQLEHLLLD LQMILNGINN YKNPKLTNMT TFKFAMPKKA TELKHLQCLE    60
EELKPLEEVL NLAQSKNFHL RPRDLISNIN VIVLELKGSE TTFMCEYADE TATIVEFLNR   120
WITFSQSIIS TLT                                                     133

SEQ ID NO: 94              moltype = AA   length = 133
FEATURE                    Location/Qualifiers
source                     1..133
                           mol_type = protein
                           organism = Homo sapiens
SEQUENCE: 94
APTSSSTKKT QLQLEHLLLD LQMILNGINN YKNPKLTNMT TFKFYMPKKA TELKHLQCLE    60
AELKPLEEVL NLAQSKNFHL RPRDLISNIN VIVLELKGSE TTFMCEYADE TATIVEFLNR   120
WITFSQSIIS TLT                                                     133

SEQ ID NO: 95              moltype = AA   length = 133
FEATURE                    Location/Qualifiers
source                     1..133
                           mol_type = protein
                           organism = Homo sapiens
SEQUENCE: 95
APASSSTKKT QLQLEHLLLD LQMILNGINN YKNPKLTNMT TFKFYMPKKA TELKHLQCLE    60
AELKPLEEVL NLAQSKNFHL RPRDLISNIN VIVLELKGSE TTFMCEYADE TATIVEFLNR   120
WITFSQSIIS TLT                                                     133

SEQ ID NO: 96              moltype = AA   length = 133
FEATURE                    Location/Qualifiers
source                     1..133
                           mol_type = protein
                           organism = Homo sapiens
SEQUENCE: 96
APTSSSTKKT QLQLEHLLLD LQMILNGINN YKNPKLTNMT TFKFYMPKKA TELKHLQCLE    60
EALKPLEEVL NLAQSKNFHL RPRDLISNIN VIVLELKGSE TTFMCEYADE TATIVEFLNR   120
WITFSQSIIS TLT                                                     133

SEQ ID NO: 97              moltype = AA   length = 133
```

```
FEATURE              Location/Qualifiers
source               1..133
                     mol_type = protein
                     organism = Homo sapiens
SEQUENCE: 97
APASSSTKKT QLQLEHLLLD LQMILNGINN YKNPKLTNMT TFKFYMPKKA TELKHLQCLE    60
EALKPLEEVL NLAQSKNFHL RPRDLISNIN VIVLELKGSE TTFMCEYADE TATIVEFLNR   120
WITFSQSIIS TLT                                                      133

SEQ ID NO: 98         moltype = AA   length = 153
FEATURE               Location/Qualifiers
source                1..153
                      mol_type = protein
                      organism = Homo sapiens
SEQUENCE: 98
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 99         moltype = AA   length = 551
FEATURE               Location/Qualifiers
source                1..551
                      mol_type = protein
                      organism = Homo sapiens
SEQUENCE: 99
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA   120
IQDFKPFENL RLMAPISLQV VHVETHRCNI SWEISQASHY FERHLEFEAR TLSPGHTWEE   180
APLLTLKQKQ EWICLETLTP DTQYEFQVRV KPLQGEFTTW SPWSQPLAFR TKPAALGKDT   240
IPWLGHLLVG LSGAFGFIIL VYLLINCRNT GPWLKKVLKC NTPDPSKFFS QLSSEHGGDV   300
QKWLSSPFPS SSFSPGGLAP EISPLEVLER DKVTQLLLQQ DKVPEPASLS SNHSLTSCFT   360
NQGYFFFHLP DALEIEACQV YFTYDPYSEE DPDEGVAGAP TGSSPQPLQP LSGEDDAYCT   420
FPSRDDLLLF SPSLLGGPSP PSTAPGGSGA GEERMPPSLQ ERVPRDWDPQ PLGPPTPGVP   480
DLVDFQPPPE LVLREAGEEV PDAGPREGVS FPWSRPPGQG EFRALNARLP LNTDAYLSLQ   540
ELQGQDPTHL V                                                        551

SEQ ID NO: 100        moltype = AA   length = 369
FEATURE               Location/Qualifiers
source                1..369
                      mol_type = protein
                      organism = Homo sapiens
SEQUENCE: 100
MLKPSLPFTS LLFLQLPLLG VGLNTTILTP NGNEDTTADF LTTMPTDSL SVSTLPLPEV     60
QCFVFNVEYM NCTWNSSSEP QPTNLTLHYW YKNSDNDKVQ KCSHYLFSEE ITSGCQLQKK   120
EIHLYQTFVV QLQDPREPRR QATQMLKLQN LVIPWAPENL TLHKLSESQL ELNWNNRFLN   180
HCLEHLVQYR TDWDHSWTEQ SVDYRHKFSL PSVDGQKRYT FRVRSRFNPL CGSAQHWSEW   240
SHPIHWGSNT SKENPLFAL EAVVISVGSM GLIISLLCVY FWLERTMPRI PTLKNLEDLV    300
TEYHGNFSAW SGVSKGLAES LQPDYSERLC LVSEIPPKGG ALGEGPGASP CNQHSPYWAP   360
PCYTLKPET                                                           369

SEQ ID NO: 101        moltype = AA   length = 8
FEATURE               Location/Qualifiers
REGION                1..8
                      note = Synthesized
source                1..8
                      mol_type = protein
                      organism = synthetic construct
SEQUENCE: 101
GSTWSINT                                                              8

SEQ ID NO: 102        moltype = AA   length = 7
FEATURE               Location/Qualifiers
REGION                1..7
                      note = Synthesized
source                1..7
                      mol_type = protein
                      organism = synthetic construct
SEQUENCE: 102
ISSGGST                                                               7

SEQ ID NO: 103        moltype = AA   length = 10
FEATURE               Location/Qualifiers
REGION                1..10
                      note = Synthesized
source                1..10
                      mol_type = protein
                      organism = synthetic construct
SEQUENCE: 103
YAQSTWYPPS                                                           10
```

```
SEQ ID NO: 104          moltype = AA   length = 25
FEATURE                 Location/Qualifiers
REGION                  1..25
                        note = Synthesized
source                  1..25
                        mol_type = protein
                        organism = synthetic construct
SEQUENCE: 104
EVQLVESGGG LVQPGGSLRL SCAAS                                           25

SEQ ID NO: 105          moltype = AA   length = 17
FEATURE                 Location/Qualifiers
REGION                  1..17
                        note = Synthesized
source                  1..17
                        mol_type = protein
                        organism = synthetic construct
SEQUENCE: 105
LAWYRQAPGK QRDLVAR                                                    17

SEQ ID NO: 106          moltype = AA   length = 38
FEATURE                 Location/Qualifiers
REGION                  1..38
                        note = Synthesized
source                  1..38
                        mol_type = protein
                        organism = synthetic construct
SEQUENCE: 106
YYADSVKGRF TISRDNSKNT LYLQMNSLRA EDTAVYYC                              38

SEQ ID NO: 107          moltype = AA   length = 11
FEATURE                 Location/Qualifiers
REGION                  1..11
                        note = Synthesized
source                  1..11
                        mol_type = protein
                        organism = synthetic construct
SEQUENCE: 107
SGQGTQVTVS S                                                          11

SEQ ID NO: 108          moltype = AA   length = 116
FEATURE                 Location/Qualifiers
REGION                  1..116
                        note = Synthesized
source                  1..116
                        mol_type = protein
                        organism = synthetic construct
SEQUENCE: 108
EVQLVESGGG LVQPGGSLRL SCAASGSTWS INTLAWYRQA PGKQRDLVAR ISSGGSTYYA      60
DSVKGRFTIS RDNSKNTLYL QMNSLRAEDT AVYYCYAQST WYPPSWGQGT LVTVSS         116

SEQ ID NO: 109          moltype = AA   length = 8
FEATURE                 Location/Qualifiers
REGION                  1..8
                        note = Synthesized
source                  1..8
                        mol_type = protein
                        organism = synthetic construct
SEQUENCE: 109
GFAFRGFG                                                               8

SEQ ID NO: 110          moltype = AA   length = 8
FEATURE                 Location/Qualifiers
REGION                  1..8
                        note = Synthesized
source                  1..8
                        mol_type = protein
                        organism = synthetic construct
SEQUENCE: 110
INNGGSDT                                                               8

SEQ ID NO: 111          moltype = AA   length = 9
FEATURE                 Location/Qualifiers
REGION                  1..9
                        note = Synthesized
source                  1..9
                        mol_type = protein
                        organism = synthetic construct
```

```
SEQUENCE: 111
AIGGPGASP                                                             9

SEQ ID NO: 112          moltype = AA  length = 25
FEATURE                 Location/Qualifiers
REGION                  1..25
                        note = Synthesized
source                  1..25
                        mol_type = protein
                        organism = synthetic construct
SEQUENCE: 112
QVQLVESGGG VVQPGGSLRL SCAAS                                           25

SEQ ID NO: 113          moltype = AA  length = 17
FEATURE                 Location/Qualifiers
REGION                  1..17
                        note = Synthesized
source                  1..17
                        mol_type = protein
                        organism = synthetic construct
SEQUENCE: 113
MSWVRQAPGK GLEWVSS                                                    17

SEQ ID NO: 114          moltype = AA  length = 11
FEATURE                 Location/Qualifiers
REGION                  1..11
                        note = Synthesized
source                  1..11
                        mol_type = protein
                        organism = synthetic construct
SEQUENCE: 114
SGQGTQVTVS S                                                          11

SEQ ID NO: 115          moltype = AA  length = 116
FEATURE                 Location/Qualifiers
REGION                  1..116
                        note = Synthesized
source                  1..116
                        mol_type = protein
                        organism = synthetic construct
SEQUENCE: 115
QVQLVESGGG VVQPGGSLRL SCAASGFAFR GFGMSWVRQA PGKGLEWVSS INNGGSDTYY      60
ADSVKGRFTI SRDNSKNTLY LQMNSLRAED TAVYYCAIGG PGASPSGQGT QVTVSS         116

SEQ ID NO: 116          moltype = AA  length = 227
FEATURE                 Location/Qualifiers
source                  1..227
                        mol_type = protein
                        organism = Homo sapiens
SEQUENCE: 116
DKTHTCPPCP APELLGGPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK    120
GQPREPQVYT LPPSREEMTK NQVSLTCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 117          moltype = AA  length = 227
FEATURE                 Location/Qualifiers
source                  1..227
                        mol_type = protein
                        organism = Homo sapiens
SEQUENCE: 117
DKTHTCPPCP APELLGGPSV FLFPPKPKDT LMISRTPEVT CVVVDVSHED PEVKFNWYVD      60
GVEVHNAKTK PREEQYASTY RVVSVLTVLH QDWLNGKEYK CKVSNKALPA PIEKTISKAK    120
GQPREPQVYT LPPSREEMTK NQVSLTCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 118          moltype = AA  length = 227
FEATURE                 Location/Qualifiers
source                  1..227
                        mol_type = protein
                        organism = Homo sapiens
SEQUENCE: 118
DKTHTCPPCP APELLGGPSV FLFPPKPKDT LMISRTPEVT CVVVDVSHED PEVKFNWYVD      60
GVEVHNAKTK PREEQYNSTY RVVSVLTVLH QDWLNGKEYK CKVSNKALPA PIEKTISKAK    120
GQPREPQVYT LPPCREEMTK NQVSLWCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 119          moltype = AA  length = 227
FEATURE                 Location/Qualifiers
```

```
                    source          1..227
                                    mol_type = protein
                                    organism = Homo sapiens
SEQUENCE: 119
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSREEMTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 120          moltype = AA  length = 227
FEATURE                 Location/Qualifiers
source                  1..227
                        mol_type = protein
                        organism = Homo sapiens
SEQUENCE: 120
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPCREEMTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 121          moltype = AA  length = 227
FEATURE                 Location/Qualifiers
source                  1..227
                        mol_type = protein
                        organism = Homo sapiens
SEQUENCE: 121
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVCT LPPSREEMTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 122          moltype = AA  length = 228
FEATURE                 Location/Qualifiers
source                  1..228
                        mol_type = protein
                        organism = Homo sapiens
SEQUENCE: 122
ERKCCVECPP CPAPPVAGPS VFLFPPKPKD TLMISRTPEV TCVVVDVSHE DPEVQFNWYV    60
DGVEVHNAKT KPREEQFNST FRVVSVLTVV HQDWLNGKEY KCKVSNKGLP APIEKTISKT   120
KGQPREPQVY TLPPSREEMT KNQVSLTCLV KGFYPSDIAV EWESNGQPEN NYKTTPPMLD   180
SDGSFFLYSK LTVDKSRWQQ GNVFSCSVMH EALHNHYTQK SLSLSPGK                228

SEQ ID NO: 123          moltype = AA  length = 229
FEATURE                 Location/Qualifiers
source                  1..229
                        mol_type = protein
                        organism = Homo sapiens
SEQUENCE: 123
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK               229

SEQ ID NO: 124          moltype = AA  length = 6
FEATURE                 Location/Qualifiers
REGION                  1..6
                        note = Synthesized
source                  1..6
                        mol_type = protein
                        organism = synthetic construct
SEQUENCE: 124
GSGGSG                                                                6

SEQ ID NO: 125          moltype = AA  length = 9
FEATURE                 Location/Qualifiers
REGION                  1..9
                        note = Synthesized
source                  1..9
                        mol_type = protein
                        organism = synthetic construct
SEQUENCE: 125
GSGGSGGSG                                                             9

SEQ ID NO: 126          moltype = AA  length = 12
FEATURE                 Location/Qualifiers
REGION                  1..12
                        note = Synthesized
source                  1..12
                        mol_type = protein
```

```
SEQUENCE: 126
GSGGSGGSGG SG                                                              12

SEQ ID NO: 127          moltype = AA  length = 4
FEATURE                 Location/Qualifiers
REGION                  1..4
                        note = Synthesized
source                  1..4
                        mol_type = protein
                        organism = synthetic construct
SEQUENCE: 127
GGGS                                                                        4

SEQ ID NO: 128          moltype = AA  length = 8
FEATURE                 Location/Qualifiers
REGION                  1..8
                        note = Synthesized
source                  1..8
                        mol_type = protein
                        organism = synthetic construct
SEQUENCE: 128
GGGSGGGS                                                                    8

SEQ ID NO: 129          moltype = AA  length = 12
FEATURE                 Location/Qualifiers
REGION                  1..12
                        note = Synthesized
source                  1..12
                        mol_type = protein
                        organism = synthetic construct
SEQUENCE: 129
GGGSGGGSGG GS                                                              12

SEQ ID NO: 130          moltype = AA  length = 16
FEATURE                 Location/Qualifiers
REGION                  1..16
                        note = Synthesized
source                  1..16
                        mol_type = protein
                        organism = synthetic construct
SEQUENCE: 130
GGGSGGGSGG GSGGGS                                                          16

SEQ ID NO: 131          moltype = AA  length = 5
FEATURE                 Location/Qualifiers
REGION                  1..5
                        note = Synthesized
source                  1..5
                        mol_type = protein
                        organism = synthetic construct
SEQUENCE: 131
GGGGS                                                                       5

SEQ ID NO: 132          moltype = AA  length = 10
FEATURE                 Location/Qualifiers
REGION                  1..10
                        note = Synthesized
source                  1..10
                        mol_type = protein
                        organism = synthetic construct
SEQUENCE: 132
GGGGSGGGGS                                                                 10

SEQ ID NO: 133          moltype = AA  length = 15
FEATURE                 Location/Qualifiers
REGION                  1..15
                        note = Synthesized
source                  1..15
                        mol_type = protein
                        organism = synthetic construct
SEQUENCE: 133
GGGGSGGGGS GGGGS                                                           15

SEQ ID NO: 134          moltype = AA  length = 20
FEATURE                 Location/Qualifiers
REGION                  1..20
                        note = Synthesized
source                  1..20
```

```
                            mol_type = protein
                            organism = synthetic construct
SEQUENCE: 134
GGGGSGGGGS GGGGSGGGGS                                                    20

SEQ ID NO: 135              moltype = AA  length = 4
FEATURE                     Location/Qualifiers
REGION                      1..4
                            note = Synthesized
source                      1..4
                            mol_type = protein
                            organism = synthetic construct
SEQUENCE: 135
SGSG                                                                      4

SEQ ID NO: 136              moltype = AA  length = 7
FEATURE                     Location/Qualifiers
REGION                      1..7
                            note = Synthesized
source                      1..7
                            mol_type = protein
                            organism = synthetic construct
SEQUENCE: 136
SGSGGSG                                                                   7

SEQ ID NO: 137              moltype = AA  length = 10
FEATURE                     Location/Qualifiers
REGION                      1..10
                            note = Synthesized
source                      1..10
                            mol_type = protein
                            organism = synthetic construct
SEQUENCE: 137
SGSGGSGGSG                                                               10

SEQ ID NO: 138              moltype = AA  length = 13
FEATURE                     Location/Qualifiers
REGION                      1..13
                            note = Synthesized
source                      1..13
                            mol_type = protein
                            organism = synthetic construct
SEQUENCE: 138
SGSGGSGGSG GSG                                                           13

SEQ ID NO: 139              moltype = AA  length = 5
FEATURE                     Location/Qualifiers
REGION                      1..5
                            note = Synthesized
source                      1..5
                            mol_type = protein
                            organism = synthetic construct
SEQUENCE: 139
SGGGS                                                                     5

SEQ ID NO: 140              moltype = AA  length = 9
FEATURE                     Location/Qualifiers
REGION                      1..9
                            note = Synthesized
source                      1..9
                            mol_type = protein
                            organism = synthetic construct
SEQUENCE: 140
SGGGSGGGS                                                                 9

SEQ ID NO: 141              moltype = AA  length = 13
FEATURE                     Location/Qualifiers
REGION                      1..13
                            note = Synthesized
source                      1..13
                            mol_type = protein
                            organism = synthetic construct
SEQUENCE: 141
SGGGSGGGSG GGS                                                           13

SEQ ID NO: 142              moltype = AA  length = 17
FEATURE                     Location/Qualifiers
REGION                      1..17
                            note = Synthesized
```

```
source                   1..17
                         mol_type = protein
                         organism = synthetic construct
SEQUENCE: 142
SGGGSGGGSG GGSGGGS                                                       17

SEQ ID NO: 143           moltype = AA   length = 6
FEATURE                  Location/Qualifiers
REGION                   1..6
                         note = Synthesized
source                   1..6
                         mol_type = protein
                         organism = synthetic construct
SEQUENCE: 143
SGGGGS                                                                    6

SEQ ID NO: 144           moltype = AA   length = 11
FEATURE                  Location/Qualifiers
REGION                   1..11
                         note = Synthesized
source                   1..11
                         mol_type = protein
                         organism = synthetic construct
SEQUENCE: 144
SGGGGSGGGG S                                                             11

SEQ ID NO: 145           moltype = AA   length = 16
FEATURE                  Location/Qualifiers
REGION                   1..16
                         note = Synthesized
source                   1..16
                         mol_type = protein
                         organism = synthetic construct
SEQUENCE: 145
SGGGGSGGGG SGGGGS                                                        16

SEQ ID NO: 146           moltype = AA   length = 21
FEATURE                  Location/Qualifiers
REGION                   1..21
                         note = Synthesized
source                   1..21
                         mol_type = protein
                         organism = synthetic construct
SEQUENCE: 146
SGGGGSGGGG SGGGGSGGGG S                                                  21

SEQ ID NO: 147           moltype = AA   length = 5
FEATURE                  Location/Qualifiers
REGION                   1..5
                         note = Synthesized
source                   1..5
                         mol_type = protein
                         organism = synthetic construct
SEQUENCE: 147
EAAAK                                                                     5

SEQ ID NO: 148           moltype = AA   length = 10
FEATURE                  Location/Qualifiers
REGION                   1..10
                         note = Synthesized
source                   1..10
                         mol_type = protein
                         organism = synthetic construct
SEQUENCE: 148
EAAAKEAAAK                                                               10

SEQ ID NO: 149           moltype = AA   length = 15
FEATURE                  Location/Qualifiers
REGION                   1..15
                         note = Synthesized
source                   1..15
                         mol_type = protein
                         organism = synthetic construct
SEQUENCE: 149
EAAAKEAAAK EAAAK                                                         15

SEQ ID NO: 150           moltype = AA   length = 20
FEATURE                  Location/Qualifiers
REGION                   1..20
```

```
                        note = Synthesized
source                  1..20
                        mol_type = protein
                        organism = synthetic construct
SEQUENCE: 150
EAAAKEAAAK EAAAKEAAAK                                              20

SEQ ID NO: 151          moltype = AA   length = 5
FEATURE                 Location/Qualifiers
REGION                  1..5
                        note = Synthesized
source                  1..5
                        mol_type = protein
                        organism = synthetic construct
SEQUENCE: 151
PAPAP                                                              5

SEQ ID NO: 152          moltype = AA   length = 10
FEATURE                 Location/Qualifiers
REGION                  1..10
                        note = Synthesized
source                  1..10
                        mol_type = protein
                        organism = synthetic construct
SEQUENCE: 152
PAPAPPAPAP                                                         10

SEQ ID NO: 153          moltype = AA   length = 15
FEATURE                 Location/Qualifiers
REGION                  1..15
                        note = Synthesized
source                  1..15
                        mol_type = protein
                        organism = synthetic construct
SEQUENCE: 153
PAPAPPAPAP PAPAP                                                   15

SEQ ID NO: 154          moltype = AA   length = 20
FEATURE                 Location/Qualifiers
REGION                  1..20
                        note = Synthesized
source                  1..20
                        mol_type = protein
                        organism = synthetic construct
SEQUENCE: 154
PAPAPPAPAP PAPAPPAPAP                                              20

SEQ ID NO: 155          moltype = AA   length = 8
FEATURE                 Location/Qualifiers
REGION                  1..8
                        note = Synthesized
source                  1..8
                        mol_type = protein
                        organism = synthetic construct
SEQUENCE: 155
IKRTVAAP                                                           8

SEQ ID NO: 156          moltype = AA   length = 133
FEATURE                 Location/Qualifiers
source                  1..133
                        mol_type = protein
                        organism = Homo sapiens
SEQUENCE: 156
QGQDRHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 157          moltype = AA   length = 133
FEATURE                 Location/Qualifiers
source                  1..133
                        mol_type = protein
                        organism = Homo sapiens
SEQUENCE: 157
QGQDEHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 158          moltype = AA   length = 123
FEATURE                 Location/Qualifiers
```

```
source                       1..123
                             mol_type = protein
                             organism = Homo sapiens
SEQUENCE: 158
QGQDRHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHL                                                                123

SEQ ID NO: 159               moltype = AA  length = 394
FEATURE                      Location/Qualifiers
source                       1..394
                             mol_type = protein
                             organism = Homo sapiens
SEQUENCE: 159
QGQDRHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDSEVQLVES GGGLVQPGGS LRLSCAASGS TWSINTLAWY RQAPGKQRDL   180
VARISSGGST YYADSVKGRF TISRDNSKNT LYLQMNSLRA EDTAVYYCYA QSTWYPPSWG   240
QGTLVTVSSG SGGSGGSGGS GAPTSSSTKK TQLQLEHLLL DLQMILNGIN NYKNPKLTRM   300
LTFKFYMPKK ATELKHLQCL EEELKPLEEV LNLAQSKNFH LRPRDLISNI NVIVLELKGS   360
ETTFMCEYAD ETATIVEFLN RWITFSQSII STLT                              394

SEQ ID NO: 160               moltype = AA  length = 394
FEATURE                      Location/Qualifiers
source                       1..394
                             mol_type = protein
                             organism = Homo sapiens
SEQUENCE: 160
APASSSTKKT QLQLEHLLLD LQMILNGINN YKNPKLTNMT TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTGSGGSGG SGGSGEVQLV ESGGGLVQPG GSLRLSCAAS GSTWSINTLA   180
WYRQAPGKQR DLVARISSGG STYYADSVKG RFTISRDNSK NTLYLQMNSL RAEDTAVYYC   240
YAQSTWYPPS WGQGTLVTVS SQGQDRHMIR MRQLIDIVDQ LKNYVNDLVP EFLPAPEDVE   300
TNCEWSAFSC FQKAQLKSAN TGNNERIINV SIKKLKRKPP STNAGRRQKH RLTCPSCDSY   360
EKKPPKEFLE RFKSLLQKMI HQHLSSRTHG SEDS                              394

SEQ ID NO: 161               moltype = AA  length = 394
FEATURE                      Location/Qualifiers
source                       1..394
                             mol_type = protein
                             organism = Homo sapiens
SEQUENCE: 161
QGQDRHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDSEVQLVES GGGLVQPGGS LRLSCAASGS TWSINTLAWY RQAPGKQRDL   180
VARISSGGST YYADSVKGRF TISRDNSKNT LYLQMNSLRA EDTAVYYCYA QSTWYPPSWG   240
QGTLVTVSSG SGGSGGSGGS GAPASSSTKK TQLQLEHLLL DLQMILNGIN NYKNPKLTNM   300
TTFKFYMPKK ATELKHLQCL EEELKPLEEV LNLAQSKNFH LRPRDLISNI NVIVLELKGS   360
ETTFMCEYAD ETATIVEFLN RWITFSQSII STLT                              394

SEQ ID NO: 162               moltype = AA  length = 394
FEATURE                      Location/Qualifiers
source                       1..394
                             mol_type = protein
                             organism = Homo sapiens
SEQUENCE: 162
APASSSTKKT QLQLEHLLLD LQMILNGINN YKNPKLTNMT TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTGSGGSGG SGGSGEVQLV ESGGGLVQPG GSLRLSCAAS GSTWSINTLA   180
WYRQAPGKQR DLVARISSGG STYYADSVKG RFTISRDNSK NTLYLQMNSL RAEDTAVYYC   240
YAQSTWYPPS WGQGTLVTVS SQGQDEHMIR MRQLIDIVDQ LKNYVNDLVP EFLPAPEDVE   300
TNCEWSAFSC FQKAQLKSAN TGNNERIINV SIKKLKRKPP STNAGRRQKH RLTCPSCDSY   360
EKKPPKEFLE RFKSLLQKMI HQHLSSRTHG SEDS                              394

SEQ ID NO: 163               moltype = AA  length = 394
FEATURE                      Location/Qualifiers
source                       1..394
                             mol_type = protein
                             organism = Homo sapiens
SEQUENCE: 163
QGQDEHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDSEVQLVES GGGLVQPGGS LRLSCAASGS TWSINTLAWY RQAPGKQRDL   180
VARISSGGST YYADSVKGRF TISRDNSKNT LYLQMNSLRA EDTAVYYCYA QSTWYPPSWG   240
QGTLVTVSSG SGGSGGSGGS GAPASSSTKK TQLQLEHLLL DLQMILNGIN NYKNPKLTNM   300
TTFKFYMPKK ATELKHLQCL EEELKPLEEV LNLAQSKNFH LRPRDLISNI NVIVLELKGS   360
ETTFMCEYAD ETATIVEFLN RWITFSQSII STLT                              394

SEQ ID NO: 164               moltype = AA  length = 413
```

```
FEATURE                 Location/Qualifiers
source                  1..413
                        mol_type = protein
                        organism = Homo sapiens
SEQUENCE: 164
DCDIEGKDGK QYESVLMVSI DQLLDSMKEI GSNCLNNEFN FFKRHICDAN KEGMFLFRAA   60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHGSGGSGGS GGSGEVQLVE SGGGLVQPGG  180
SLRLSCAASG STWSINTLAW YRQAPGKQRD LVARISSGGS TYYADSVKGR FTISRDNSKN  240
TLYLQMNSLR AEDTAVYYCY AQSTWYPPSW GQGTLVTVSS QGQDEHMIRM RQLIDIVDQL  300
KNYVNDLVPE FLPAPEDVET NCEWSAFSCF QKAQLKSANT GNNERIINVS IKKLKRKPPS  360
TNAGRRQKHR LTCPSCDSYE KKPPKEFLER FKSLLQKMIH QHLSSRTHGS EDS         413

SEQ ID NO: 165          moltype = AA  length = 413
FEATURE                 Location/Qualifiers
source                  1..413
                        mol_type = protein
                        organism = Homo sapiens
SEQUENCE: 165
QGQDEHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDSEVQLVES GGGLVQPGGS LRLSCAASGS TWSINTLAWY RQAPGKQRDL  180
VARISSGGST YYADSVKGRF TISRDNSKNT LYLQMNSLRA EDTAVYYCYA QSTWYPPSWG  240
QGTLVTVSSG SGGSGGSGGS GDCDIEGKDG KQYESVLMVS IDQLLDSMKE IGSNCLNNEF  300
NFFKRHICDA NKEGMFLFRA ARKLRQFLKM NSTGDFDLHL LKVSEGTTIL LNCTGQVKGR  360
KPAALGEAQP TKSLEENKSL KEQKKLNDLC FLKRLLQEIK TCWNKILMGT KEH         413

SEQ ID NO: 166          moltype = AA  length = 394
FEATURE                 Location/Qualifiers
source                  1..394
                        mol_type = protein
                        organism = Homo sapiens
SEQUENCE: 166
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLTGSGGSGG SGGSGQVQLV ESGGGVVQPG GSLRLSCAAS GFAFRGFGMS  180
WVRQAPGKGL EWVSSINNGG SDTYYADSVK GRFTISRDNS KNTLYLQMNS LRAEDTAVYY  240
CAIGGPGASP SGQGTQVTVS SQGQDRHMIR MRQLIDIVDQ LKNYVNDLVP EFLPAPEDVE  300
TNCEWSAFSC FQKAQLKSAN TGNNERIINV SIKKLKRKPP STNAGRRQKH RLTCPSCDSY  360
EKKPPKEFLE RFKSLLQKMI HQHLSSRTHG SEDS                              394

SEQ ID NO: 167          moltype = AA  length = 397
FEATURE                 Location/Qualifiers
source                  1..397
                        mol_type = protein
                        organism = Homo sapiens
SEQUENCE: 167
QGQDRHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDSQVQLVES GGGVVQPGGS LRLSCAASGF AFRGFGMSWV RQAPGKGLEW  180
VSSINNGGSD TYYADSVKGR FTISRDNSKN TLYLQMNSLR AEDTAVYYCA IGGPGASPSG  240
QGTQVTVSSG GGGSGGGGSG GGGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFSQ SIISTLT                           397

SEQ ID NO: 168          moltype = AA  length = 394
FEATURE                 Location/Qualifiers
source                  1..394
                        mol_type = protein
                        organism = Homo sapiens
SEQUENCE: 168
APASSSTKKT QLQLEHLLLD LQMILNGINN YKNPKLTNMT TFKFYMPKKA TELKHLQCLE   60
EELKPLEEVL NLAQSKNFHL RPRDLISNIN VIVLELKGSE TTFMCEYADE TATIVEFLNR  120
WITFSQSIIS TLTGSGGSGG SGGSGQVQLV ESGGGVVQPG GSLRLSCAAS GFAFRGFGMS  180
WVRQAPGKGL EWVSSINNGG SDTYYADSVK GRFTISRDNS KNTLYLQMNS LRAEDTAVYY  240
CAIGGPGASP SGQGTQVTVS SQGQDRHMIR MRQLIDIVDQ LKNYVNDLVP EFLPAPEDVE  300
TNCEWSAFSC FQKAQLKSAN TGNNERIINV SIKKLKRKPP STNAGRRQKH RLTCPSCDSY  360
EKKPPKEFLE RFKSLLQKMI HQHLSSRTHG SEDS                              394

SEQ ID NO: 169          moltype = AA  length = 397
FEATURE                 Location/Qualifiers
source                  1..397
                        mol_type = protein
                        organism = Homo sapiens
SEQUENCE: 169
QGQDRHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDSQVQLVES GGGVVQPGGS LRLSCAASGF AFRGFGMSWV RQAPGKGLEW  180
VSSINNGGSD TYYADSVKGR FTISRDNSKN TLYLQMNSLR AEDTAVYYCA IGGPGASPSG  240
```

```
QGTQVTVSSG GGGSGGGGSG GGGSAPASSS TKKTQLQLEH LLLDLQMILN GINNYKNPKL   300
TNMTTFKFYM PKKATELKHL QCLEEELKPL EEVLNLAQSK NFHLRPRDLI SNINVIVLEL   360
KGSETTFMCE YADETATIVE FLNRWITFSQ SIISTLT                           397

SEQ ID NO: 170              moltype = AA  length = 394
FEATURE                     Location/Qualifiers
source                      1..394
                            mol_type = protein
                            organism = Homo sapiens
SEQUENCE: 170
APASSSTKKT QLQLEHLLLD LQMILNGINN YKNPKLTNMT TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTGSGGSGG SGGSGQVQLV ESGGGVVQPG GSLRLSCAAS GFAFRGFGMS   180
WVRQAPGKGL EWVSSINNGG SDTYYADSVK GRFTISRDNS KNTLYLQMNS LRAEDTAVYY   240
CAIGGPGASP SGQGTQVTVS SQGQDEHMIR MRQLIDIVDQ LKNYVNDLVP EFLPAPEDVE   300
TNCEWSAFSC FQKAQLKSAN TGNNERIINV SIKKLKRKPP STNAGRRQKH RLTCPSCDSY   360
EKKPPKEFLE RFKSLLQKMI HQHLSSRTHG SEDS                              394

SEQ ID NO: 171              moltype = AA  length = 397
FEATURE                     Location/Qualifiers
source                      1..397
                            mol_type = protein
                            organism = Homo sapiens
SEQUENCE: 171
QGQDEHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDSQVQLVES GGGVVQPGGS LRLSCAASGF AFRGFGMSWV RQAPGKGLEW   180
VSSINNGGSD TYYADSVKGR FTISRDNSKN TLYLQMNSLR AEDTAVYYCA IGGPGASPSG   240
QGTQVTVSSG GGGSGGGGSG GGGSAPASSS TKKTQLQLEH LLLDLQMILN GINNYKNPKL   300
TNMTTFKFYM PKKATELKHL QCLEEELKPL EEVLNLAQSK NFHLRPRDLI SNINVIVLEL   360
KGSETTFMCE YADETATIVE FLNRWITFSQ SIISTLT                           397

SEQ ID NO: 172              moltype = AA  length = 114
FEATURE                     Location/Qualifiers
source                      1..114
                            mol_type = protein
                            organism = Homo sapiens
SEQUENCE: 172
NWVNVISDLK KIEDLIQSMH IDATLYTESD VHPSCKVTAM KCFLLELQVI SLESGDASIH    60
DTVENLIILA NNSLSSNGNV TESGCKECEE LEEKNIKEFL QSFVHIVQMF INTS         114
```